(12) United States Patent
Mizuki et al.

(10) Patent No.: US 9,203,036 B2
(45) Date of Patent: Dec. 1, 2015

(54) CARBAZOLE COMPOUND, MATERIAL FOR ORGANIC ELECTROLUMINESCENCE DEVICE AND ORGANIC ELECTROLUMINESCENCE DEVICE

(71) Applicant: IDEMITSU KOSAN CO., LTD., Chiyoda-ku (JP)

(72) Inventors: Yumiko Mizuki, Sodegaura (JP); Tetsuya Inoue, Sodegaura (JP); Nobuhiro Yabunouchi, Sodegaura (JP); Kumiko Hibino, Sodegaura (JP); Kazuki Nishimura, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 386 days.

(21) Appl. No.: 13/756,917

(22) Filed: Feb. 1, 2013

(65) Prior Publication Data

US 2013/0214258 A1 Aug. 22, 2013

Related U.S. Application Data

(60) Provisional application No. 61/598,537, filed on Feb. 14, 2012.

(30) Foreign Application Priority Data

Feb. 3, 2012 (JP) .................. 2012-022534

(51) Int. Cl.
*C08G 73/06* (2006.01)
*H01L 51/00* (2006.01)
(Continued)

(52) U.S. Cl.
CPC .......... *H01L 51/0072* (2013.01); *C07D 403/04* (2013.01); *C07D 403/10* (2013.01);
(Continued)

(58) Field of Classification Search
CPC ............ H01L 51/0072; H01L 51/5012; C07D 403/04; C07D 403/10

USPC ........................................................ 528/423
See application file for complete search history.

(56) References Cited

U.S. PATENT DOCUMENTS 4,356,429 A 10/1982 Tang
6,534,199 B1 3/2003 Hosokawa et al.
(Continued)

FOREIGN PATENT DOCUMENTS

EP 2 138 551 A2 12/2009
EP 2 141 214 A2 1/2010
(Continued)

OTHER PUBLICATIONS

U.S. Appl. No. 13/900,939, filed May 23, 2013, Mizuki, et al.
(Continued)

*Primary Examiner* — Shane Fang
(74) *Attorney, Agent, or Firm* — Oblon, McClelland, Maier & Neustadt, L.L.P.

(57) ABSTRACT

A compound of the invention is represented by a formula (1) below. In the formula (1), at least one of $A_1$ and $A_2$ represents a substituted or unsubstituted nitrogen-containing aromatic heterocyclic group. A material for an organic electroluminescence device contains the compound represented by the formula (1). The material for an organic electroluminescence device includes an organic thin-film layer between an anode and a cathode, in which the organic thin-film layer contains the compound represented by the formula (1).

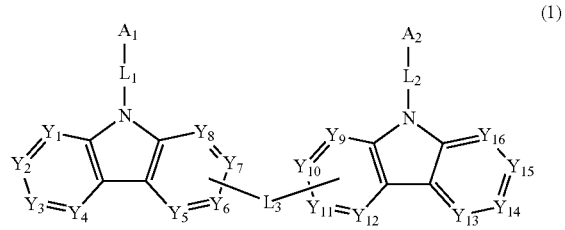

(1)

20 Claims, 3 Drawing Sheets

(51) Int. Cl.
  *C07D 403/04* (2006.01)
  *C07D 403/10* (2006.01)
  *H01L 51/50* (2006.01)
  *C07D 403/14* (2006.01)

(52) U.S. Cl.
  CPC .......... *C07D403/14* (2013.01); *H01L 51/5012* (2013.01); *H01L 51/0059* (2013.01); *H01L 51/0061* (2013.01); *H01L 51/0067* (2013.01); *H01L 51/0085* (2013.01); *H01L 51/5016* (2013.01)

(56) References Cited

U.S. PATENT DOCUMENTS

| | | |
|---|---|---|
| 2008/0145699 A1 | 6/2008 | Yabe et al. |
| 2009/0091253 A1 | 4/2009 | Yasukawa et al. |
| 2009/0302743 A1 | 12/2009 | Kato et al. |
| 2009/0309488 A1 | 12/2009 | Kato et al. |
| 2010/0012931 A1 | 1/2010 | Kato et al. |
| 2010/0039026 A1 | 2/2010 | Yang et al. |
| 2010/0141126 A1 | 6/2010 | Otsu et al. |
| 2010/0301313 A1 | 12/2010 | Ito et al. |
| 2011/0278552 A1 | 11/2011 | Numata et al. |
| 2011/0297924 A1 | 12/2011 | Yabunouchi et al. |
| 2012/0138915 A1 | 6/2012 | Nishimura et al. |
| 2012/0181524 A1 | 7/2012 | Kato et al. |
| 2012/0238105 A1 | 9/2012 | Anémian et al. |
| 2012/0273766 A1 | 11/2012 | Kato et al. |
| 2012/0319052 A1 | 12/2012 | Brocke et al. |
| 2012/0319095 A1 * | 12/2012 | Tada et al. .................. 257/40 |
| 2013/0020565 A1 | 1/2013 | Numata et al. |
| 2013/0075716 A1 | 3/2013 | Nishimura et al. |
| 2013/0092913 A1 | 4/2013 | Nishimura et al. |
| 2013/0214258 A1 | 8/2013 | Mizuki et al. |
| 2013/0234119 A1 | 9/2013 | Mizuki et al. |
| 2013/0270540 A1 | 10/2013 | Masaki Numata |

FOREIGN PATENT DOCUMENTS

| | | |
|---|---|---|
| EP | 2 161 319 A2 | 3/2010 |
| EP | 2 256 176 A1 | 12/2010 |
| EP | 2 281 862 A2 | 2/2011 |
| EP | 2 281 863 A2 | 2/2011 |
| EP | 2 562 229 A1 | 2/2013 |
| JP | 57-51781 | 3/1982 |
| JP | 9-3448 | 1/1997 |
| JP | 2000-173774 | 6/2000 |
| JP | 2004-71500 A | 3/2004 |
| JP | 2004-217557 | 8/2004 |
| JP | 2004-217557 A | 8/2004 |
| JP | 2004-273128 | 9/2004 |
| JP | 2004-311404 A | 11/2004 |
| JP | 2004-342391 | 12/2004 |
| JP | 2006-199679 | 8/2006 |
| JP | 2009-57307 | 3/2009 |
| JP | 2009-221442 | 10/2009 |
| JP | 2009-267255 A | 11/2009 |
| JP | 2010-40830 A | 2/2010 |
| JP | 2013-108015 A | 6/2013 |
| KR | 10-2011-0011578 | 2/2011 |
| WO | WO 2004/055129 A1 | 7/2004 |
| WO | WO 2006/013739 A1 | 2/2006 |
| WO | WO 2006/067976 A1 | 6/2006 |
| WO | WO 2007/108327 A1 | 9/2007 |
| WO | WO 2009/060742 A1 | 5/2009 |
| WO | WO 2009/060757 A1 | 5/2009 |
| WO | WO 2010/064871 A1 | 6/2010 |
| WO | WO 2011/105161 A1 | 9/2011 |
| WO | WO 2011/162162 A1 | 12/2011 |
| WO | WO 2012/099038 A1 | 7/2012 |
| WO | WO 2012/105310 A1 | 8/2012 |
| WO | WO 2012/121101 A1 | 9/2012 |
| WO | WO 2012/128298 A1 | 9/2012 |
| WO | WO 2012/140863 A1 | 10/2012 |
| WO | WO 2012/157211 A1 | 11/2012 |
| WO | WO 2012/165256 A1 | 12/2012 |
| WO | WO 2013/046635 A1 | 4/2013 |
| WO | WO 2013/057908 A1 | 4/2013 |
| WO | WO 2013/057922 A1 | 4/2013 |
| WO | WO 2013/069242 A1 | 5/2013 |
| WO | WO 2013/073356 A1 | 5/2013 |
| WO | WO 2013/084885 A1 | 6/2013 |
| WO | WO 2013/105206 A1 | 7/2013 |

OTHER PUBLICATIONS

U.S. Appl. No. 13/778,629, filed Feb. 27, 2013, Mizuki, et al.
U.S. Appl. No. 13/983,687, filed Oct. 2, 2013, Inoue, et al.
International Search Report issued Mar. 19, 2013, in patent application No. PCT/JP2013/052277 (with English translation).
James Lindley, "Copper Assisted Nucleophilic Substitution of Aryl Halogen", Tetrahedron vol. 40, No. 9, (Tetrahedron Report No. 163), 1984, pp. 1433-1456.
Artis Klapars, et al., "A General and Efficient Copper Catalyst for the Amidation of Aryl Halides and the N-Arylation of Nitrogen Heterocycles", J. Am. Chem. Soc. 2001, 123, pp. 7727-7729.

* cited by examiner

COMPOUND A

COMPOUND B

CARBAZOLE COMPOUND, MATERIAL FOR ORGANIC ELECTROLUMINESCENCE DEVICE AND ORGANIC ELECTROLUMINESCENCE DEVICE

THE ENTIRE DISCLOSURE OF JAPANESE PATENT APPLICATION NO. 2012-022534, FILED Feb. 3, 2012, AND U.S. PROVISIONAL APPLICATION No. 61/598,537, FILED Feb. 14, 2012, ARE EXPRESSLY INCORPORATED BY REFERENCE HEREIN.

FIELD

Embodiments described herein relates to a carbazole compound, a material for an organic electroluminescence device, and an organic electroluminescence device.

BACKGROUND

When a voltage is applied on an organic electroluminescence device (hereinafter, occasionally referred to as an organic EL device), holes and electrons are respectively injected into an emitting layer from an anode and a cathode. In the emitting layer, the injected holes and electrons are recombined to form excitons. Herein, singlet excitons and triplet excitons are formed at a ratio of 25%:75% according to electron spins statistics. In a classification according to emission principle, in a fluorescent organic EL device which uses emission caused by singlet excitons, the limit value of an internal quantum efficiency is believed to be 25%. On the other hand, in a phosphorescent EL device which uses emission caused by triplet excitons, it has been known that the internal quantum efficiency can be improved up to 100% when intersystem crossing efficiently occurs from the singlet excitons.

In a typical organic EL device, the most suitable device design has been made depending on fluorescent and phosphorescent emission mechanism. Particularly, when a fluorescent device technique is simply used for designing the phosphorescent organic EL device, it has been known that a highly efficient phosphorescent organic EL device cannot be obtained because of a luminescence property of the phosphorescent organic EL device. The reasons are generally considered as follows.

First of all, since the phosphorescent emission is generated using triplet excitons, an energy gap of a compound for the emitting layer must be large. This is because a value of singlet energy (i.e., an energy gap between energy in the lowest singlet state and energy in the ground state) of a compound is typically larger than a value of triplet energy (i.e., an energy gap between energy in the lowest triplet state and energy in the ground state) of the compound.

Accordingly, in order to efficiently trap triplet energy of a phosphorescent dopant material in the device, a host material having larger triplet energy than that of the phosphorescent dopant material needs to be used in the emitting layer. Moreover, when an electron transporting layer and a hole transporting layer are provided adjacent to the emitting layer, a compound used as the electron transporting layer and the hole transporting layer need to have a larger triplet energy than that of the phosphorescent dopant material. Thus, according to the designing idea of the typical organic EL device, a compound having a larger energy gap than that of a compound used as a fluorescent organic EL device is used for producing a phosphorescent organic EL device. As a result, a drive voltage of the overall phosphorescent organic EL device increases.

Although a hydrocarbon compound exhibiting a high oxidation resistance and a high reduction resistance is useful for the fluorescent device, the hydrocarbon compound has a broad $\pi$ electron cloud to render the energy gap small. For this reason, such a hydrocarbon compound is unlikely to be selected as the phosphorescent organic EL device but an organic compound containing a hetero atom such as oxygen and nitrogen is selected. However, the phosphorescent organic EL device in which the organic compound containing a hetero atom is used in an emitting layer exhibits a shorter lifetime than that of the fluorescent organic EL device.

Moreover, device performance of the phosphorescent organic EL device is greatly affected by an exciton relaxation rate of triplet excitons much longer than that of singlet excitons in the phosphorescent dopant material.

In other words, with respect to emission from the singlet excitons, since a relaxation rate leading to emission is so fast that the singlet excitons are unlikely to diffuse to the neighboring layers of the emitting layer (e.g., the hole transporting layer and the electron transporting layer), efficient emission is expected.

On the other hand, emission from the triplet excitons is based on forbidden spin transition and a relaxation rate is slow. Accordingly, the triplet excitons are likely to diffuse to the neighboring layers, so that the triplet excitons are thermally energy-deactivated unless the phosphorescent dopant material is a specific phosphorescent compound. In short, in the phosphorescent organic EL device, control of the recombination region of the electrons and the holes is more important as compared with control thereof in the fluorescent organic EL device.

For the above reasons, advancement of the phosphorescent organic EL device requires material selection and device design different from those of the fluorescent organic EL device.

A carbazole derivative is typically known as a compound used for the phosphorescent organic EL device. The carbazole derivative exhibits a high triplet energy and has a carbazole skeleton known as a main skeleton of a hole transporting material. The carbazole derivative is used as a useful phosphorescent host material.

Patent Literature 1 (JP-A-2004-217557) and Patent Literature 2 disclose that a compound obtained by bonding two carbazole rings through a linking group is used as a material for an organic EL device. Patent Literature 3 (JP-A-2006-199679) discloses that an N,N-carbazole compound in which two carbazole rings are bonded to each other at respective ninth positions (N position) through a linking group Z into which a nitrogen-containing heterocyclic group is introduced is used as a material for an organic EL device.

However, improvement in a luminous efficiency of the organic EL device is still demanded and development of a compound capable of improving a luminous efficiency and a material for an organic EL device containing the compound is desired.

SUMMARY OF THE INVENTION

An object of an embodiment of the invention is to provide a novel compound capable of improving a luminous efficiency of an organic electroluminescence device and a material for an organic electroluminescence device containing the compound. Further, an object of another embodiment of the invention is to improve a luminous efficiency of an organic electroluminescence device by using the compound or the material for an organic electroluminescence device.

After vigorous study to achieve the above object, inventors found that, in a biscarbazole derivative in which two carbazoles or azacarbazoles (hereinafter, collectively referred to as a carbazole derivative) are bonded to each other, the two carbazole derivatives are bonded to each other through a specific linking group, and further, at least one of the bonded two carbazole derivative is bonded at a ninth position thereof to a substituted or unsubstituted nitrogen-containing aromatic heterocyclic group directly or through another linking group, thereby improving a luminous efficiency of an organic electroluminescence device using the biscarbazole derivative.

The inventors have achieved the invention on the above findings.

A compound according to an exemplary embodiment is represented by a formula (1) below.

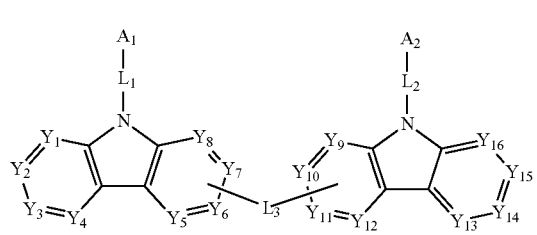

(1)

In the formula (1), $A_1$ and $A_2$ each independently represent a substituted or unsubstituted aromatic hydrocarbon group having 6 to 30 ring carbon atoms, or substituted or unsubstituted aromatic heterocyclic group having 1 to 30 ring carbon atoms. At least one of $A_1$ and $A_2$ represents a substituted or unsubstituted nitrogen-containing aromatic heterocyclic group.

$Y_1$ to $Y_{16}$ each independently represent CR or a nitrogen atom. Among $Y_5$ to $Y_{12}$, ones bonded to $L_3$ represent a carbon atom. In CR, R each independently represents a hydrogen atom, a substituted or unsubstituted aromatic hydrocarbon group having 6 to 30 ring carbon atoms, a substituted or unsubstituted aromatic heterocyclic group having 1 to 30 ring carbon atoms, a substituted or unsubstituted linear, branched or cyclic alkyl group having 1 to 30 carbon atoms, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a substituted or unsubstituted haloalkyl group having 1 to 30 carbon atoms, a substituted or unsubstituted haloalkoxy group having 1 to 30 carbon atoms, a substituted or unsubstituted alkylsilyl group having 3 to 30 carbon atoms, a substituted or unsubstituted dialkylarylsilyl group having 8 to 40 carbon atoms, a substituted or unsubstituted alkyldiarylsilyl group having 13 to 50 carbon atoms, a substituted or unsubstituted triarylsilyl group having 18 to 60 carbon atoms, a substituted or unsubstituted alkenyl group having 2 to 30 carbon atoms, a substituted or unsubstituted alkynyl group having 2 to 30 carbon atoms, a halogen atom, a cyano group, a hydroxyl group, a nitro group or a carboxy group. When a plurality of R are present, the plurality of R are the same or different. When adjacent two of $Y_1$ to $Y_{16}$ are CR, in the adjacent CR, a part of R is optionally bonded to a part of R to form a cyclic structure.

In the formula (1), $L_1$ and $L_2$ each independently represent a single bond or a linking group.

In the formula (1), $L_3$ represents a linking group represented by any one of the following formulae (2) to (4) or a composite linking group in which the linking groups represented by the formulae (2) to (4) are combined.

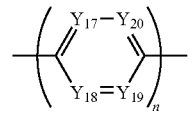

(2)

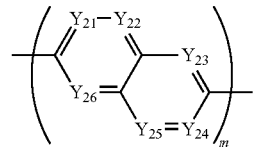

(3)

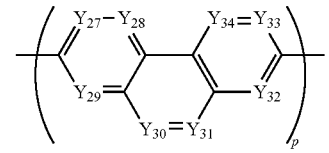

(4)

In the formulae (2) to (4), $Y_{17}$ to $Y_{34}$ each independently represent CH or a nitrogen atom.

In the formulae (2) to (4), n, m and p each independently represent an integer of 1 to 5. When $L_3$ is a composite linking group in which the linking groups represented by the formulae (2) to (4) are combined, n+m+p is an inter of 1 to 5.

In the compound according to the exemplary embodiment, at least one of $A_1$ and $A_2$ in the formula (1) is preferably represented by a formula (5) below.

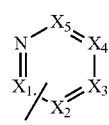

(5)

In the formula (5), $X_1$ to $X_5$ each independently represent $CR^b$ or a nitrogen atom. At least one of $X_1$ to $X_5$ is a nitrogen atom and $X_1$ to $X_5$ bonded to $L_1$ or $L_2$ is a carbon atom.

In $CR^b$, $R^b$ represents a hydrogen atom or a substituent. When adjacent two of $X_1$ to $X_5$ are $CR^b$, in the adjacent $CR^b$, a part of $R^b$ is optionally bonded to a part of $R^b$ to form a cyclic structure.

When a plurality of $R^b$ are present, the plurality of $R^b$ are the same or different.

In the compound according to the exemplary embodiment, $Y_{17}$ to $Y_{34}$ in the formulae (2) to (4) are preferably CH.

In the compound according to the exemplary embodiment, at least one of $A_1$ and $A_2$ in the formula (1) is preferably a substituted or unsubstituted pyrimidinyl group or substituted or unsubstituted triazinyl group.

In the compound according to the exemplary embodiment, n in the formula (2), m in the formula (3) and p in the formula (4) preferably independently represent an integer of 1 to 3.

In the compound according to the exemplary embodiment, $L_3$ in the formula (1) is preferably a linking group represented by the formula (2).

In the compound according to the exemplary embodiment, the compound represented by the formula (1) is preferably represented by any one of the following formulae (6) to (8).

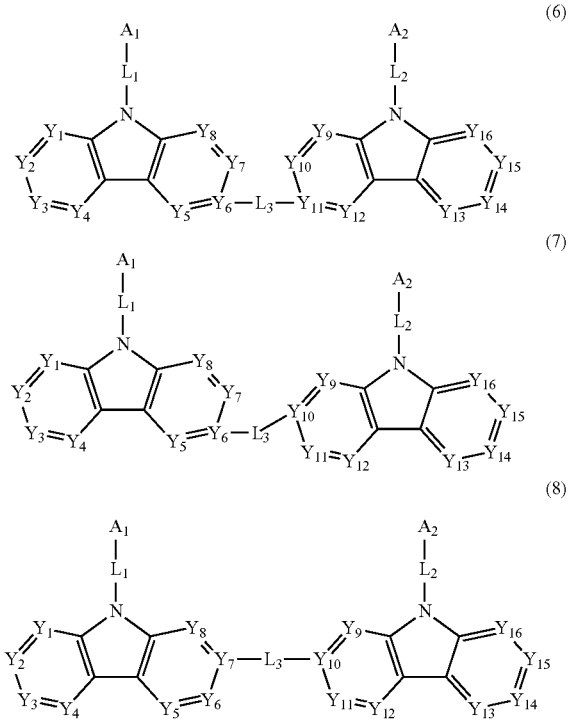

In the formula (6), $A_1$, $A_2$, $Y_1$ to $Y_5$, $Y_7$ to $Y_{10}$, $Y_{12}$ to $Y_{16}$, $L_1$, $L_2$ and $L_3$ represent the same as those in the formula (1) and $Y_6$ and $Y_{11}$ represent a carbon atom.

In the formula (7), $A_1$, $A_2$, $Y_1$ to $Y_5$, $Y_7$ to $Y_9$, $Y_{11}$ to $Y_{16}$, $L_1$, $L_2$ and $L_3$ represent the same as those in the formula (1), and $Y_6$ and $Y_{10}$ represent a carbon atom.

In the formula (8), $A_1$, $A_2$, $Y_1$ to $Y_6$, $Y_8$ to $Y_9$, $Y_{11}$ to $Y_{16}$, $L_1$, $L_2$ and $L_3$ represent the same as those in the formula (1), and $Y_7$ and $Y_{10}$ represent a carbon atom.

In the compound according to the exemplary embodiment, among $Y_5$ to $Y_{12}$ in the formula (1), $Y_5$ to $Y_{12}$ bonded to $L_3$ are a carbon atom and the rest of $Y_5$ to $Y_{12}$ are CH.

In the compound according to the exemplary embodiment, one of $A_1$ and $A_2$ in the formula (1) is preferably a substituted or unsubstituted aromatic heterocyclic group having 1 to 30 ring carbon atoms, and the other of $A_1$ and $A_2$ is preferably a substituted or unsubstituted aromatic hydrocarbon group having 6 to 30 ring carbon atoms.

A material for an organic electroluminescence device according to another exemplary embodiment contains the compound according to the above exemplary embodiment.

An organic electroluminescence device according to still another exemplary embodiment includes: a cathode; an anode; and an organic thin-film layer disposed between the cathode and the anode, the organic thin-film layer having one or more layers including an emitting layer, in which at least one of the organic thin-film layer includes the compound according to the above exemplary embodiment.

In the organic electroluminescence device according to the exemplary embodiment, the emitting layer preferably contains any one of the compound according to the above exemplary embodiment.

In the organic electroluminescence device according to the exemplary embodiment, the emitting layer preferably includes a phosphorescent material.

In the organic electroluminescence device according to the exemplary embodiment, the phosphorescent material is an ortho-metalated complex of a metal atom selected from iridium (Ir), osmium (Os) and platinum (Pt).

According to the embodiments, a novel compound capable of improving a luminous efficiency of an organic electroluminescence device and a material for an organic electroluminescence device containing the compound can be provided. Further, according to the embodiments, a luminous efficiency of an organic electroluminescence device can be improved by using the compound and the material for an organic electroluminescence device.

DESCRIPTION OF EMBODIMENTS

Figure 1:
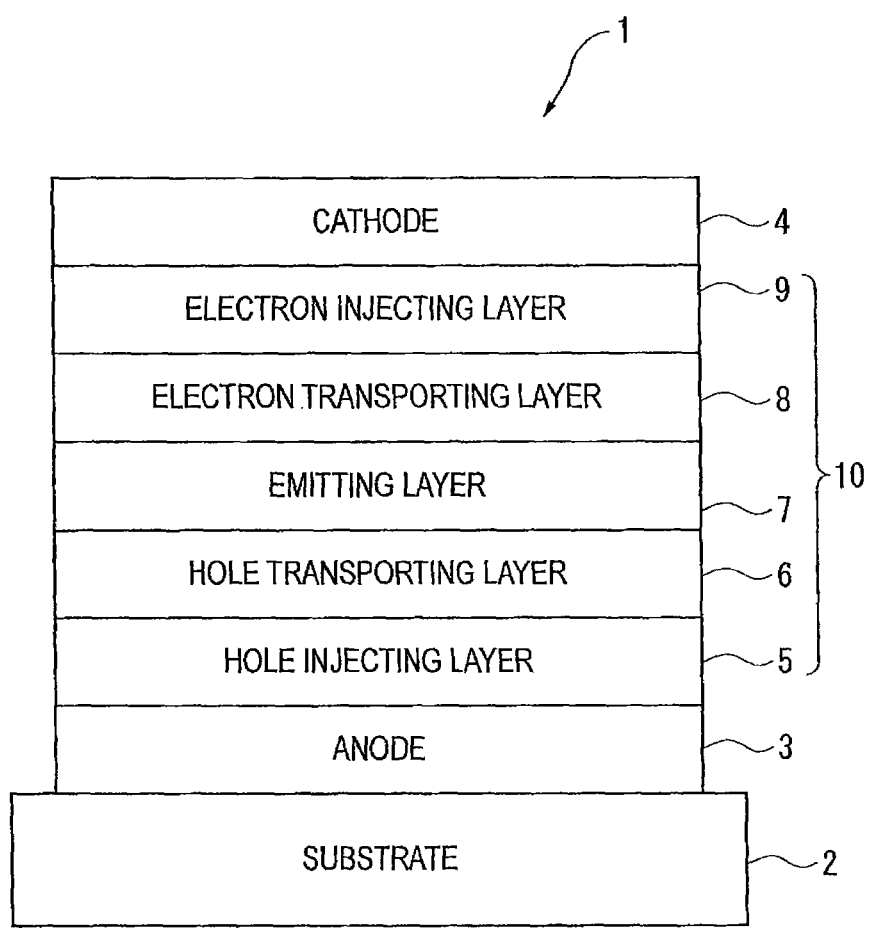
FIG. 1 schematically shows an exemplary arrangement of an organic EL device according to an exemplary embodiment of the invention.

The invention will be described below in detail.
Compound
A compound according to an exemplary embodiment is represented by a formula (1) below.

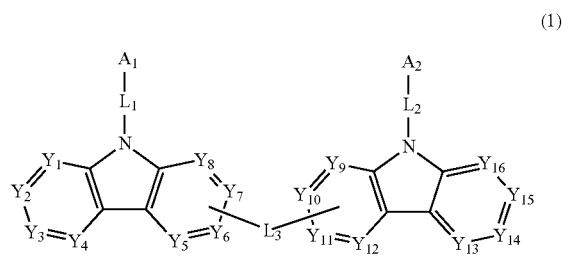

In the formula (1), $A_1$ and $A_2$ each independently represent a substituted or unsubstituted aromatic hydrocarbon group having 6 to 30 ring carbon atoms, or substituted or unsubstituted aromatic heterocyclic group having 1 to 30 ring carbon atoms. At least one of $A_1$ and $A_2$ represents a substituted or unsubstituted nitrogen-containing aromatic heterocyclic group.

In the formula (1), $Y_1$ to $Y_{16}$ each independently represent CR or a nitrogen atom. Among $Y_5$ to $Y_{12}$, ones bonded to $L_3$ represent a carbon atom.

CR represents R bonded to a carbon atom (C).

In CR, R independently represents a hydrogen atom, substituted or unsubstituted aromatic hydrocarbon group having 6 to 30 ring carbon atoms, substituted or unsubstituted aromatic heterocyclic group having 1 to 30 ring carbon atoms, substituted or unsubstituted linear, branched or cyclic alkyl group having 1 to 30 carbon atoms, substituted or unsubstituted alkoxy group having 1 to 30 carbon atoms, substituted or unsubstituted aryloxy group having 6 to 30 ring carbon atoms, substituted or unsubstituted aralkyl having 7 to 30 carbon atoms, substituted or unsubstituted haloalkyl group having 1 to 30 carbon atoms, substituted or unsubstituted haloalkoxy group having 1 to 30 carbon atoms, substituted or unsubstituted alkylsilyl group having 3 to 30 carbon atoms, substituted or unsubstituted dialkyl arylsilyl group having 8 to 40 carbon atoms, substituted or unsubstituted alkyl diarylsilyl group having 13 to 50 carbon atoms, substituted or unsubstituted triarylsilyl group having 18 to 60 carbon atoms, halogen atom, cyano group, hydroxyl group, nitro group or carboxy group. When a plurality of R are present, the plurality of R are the same or different. When adjacent two of $Y_1$ to $Y_{16}$ are CR, in the adjacent CR, a part of R is optionally bonded to a part of R to form a cyclic structure.

In the compound according to the exemplary embodiment, at least one of $A_1$ and $A_2$ in the formula (1) is preferably represented by a formula (5) below.

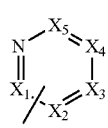

(5)

In the formula (5), $X_1$ to $X_5$ each independently represent $CR^b$ or a nitrogen atom. $CR^b$ represents $R^b$ bonded to a carbon atom (C).

At least one of $X_1$ to $X_5$ is a nitrogen atom. $X_1$ to $X_5$ bonded to $L_1$ or $L_2$ is a carbon atom.

In $CR^b$, $R^b$ represents a hydrogen atom or a substituent. When adjacent two of $X_1$ to $X_5$ are $CR^b$, in the adjacent $CR^b$, a part of $R^b$ may be bonded to a part of $R^b$ to form a cyclic structure.

When a plurality of $R^b$ are present, the plurality of $R^b$ are the same or different.

In $CR^b$, a substituent of $R^b$ is exemplified by the groups for R in CR, which excludes a hydrogen atom.

In the formula (5), $R^b$ in $CR^b$ is preferably hydrogen, a substituted or unsubstituted aromatic hydrocarbon group having 6 to 30 ring carbon atoms, or substituted or unsubstituted aromatic heterocyclic group having 1 to 30 ring carbon atoms.

The nitrogen-containing aromatic heterocyclic group represented by the formula (5) is preferably a heterocyclic group having a pyrimidine skeleton or a heterocyclic group having a triazine skeleton.

The heterocyclic group having the pyrimidine skeleton is exemplified by a substituted or unsubstituted pyrimidinyl group. Examples of the pyrimidinyl group are a 2-pyrimidinyl group, 4-pyrimidinyl group, 5-pyrimidinyl group and 6-pyrimidinyl group.

The heterocyclic group having the triazine skeleton is exemplified by a substituted or unsubstituted triazinyl group. The triazinyl group is a group formed from a triazine ring and has three kinds of 1,2,3-triazine, 1,2,4-triazine and 1,3,5-triazine. Examples of the triazinyl group are a 1,2,3-triazine-4-yl group, 1,2,4-triazine-3-yl group and 1,3,5-triazine-2-yl group.

In the compound according to the exemplary embodiment, at least one of $A_1$ and $A_2$ in the formula (1) is preferably a substituted or unsubstituted pyrimidinyl group or substituted or unsubstituted triazinyl group.

It is speculated that, as compared with bonding of other nitrogen-containing aromatic heterocyclic group such as an imidazopyridinyl group, bonding of a pyrimidinyl group or triazinyl group at $A_1$ or $A_2$ improves resistance of the biscarbazole derivative against holes and electrons.

$L_1$ to $L_2$ each independently represent a single bond or a linking group.

In the formula (1), a linking group at $L_1$ and $L_2$ is preferably a divalent group induced from a substituted or unsubstituted aromatic hydrocarbon compound having 6 to 30 ring carbon atoms, or a divalent group induced from a substituted or unsubstituted aromatic heterocyclic compound having 1 to 30 ring carbon atoms.

When at least one of $L_1$ and $L_2$ is a single bond, hole transporting capability is improved.

When at least one of $L_1$ and $L_2$ is a divalent group induced from a substituted or unsubstituted aromatic hydrocarbon compound having 6 to 30 ring carbon atoms, or a divalent group induced from a substituted or unsubstituted aromatic heterocyclic compound having 1 to 30 ring carbon atoms, electron transporting capability tends to be improved.

Accordingly, it is desirable to appropriately select $L_1$ and $L_2$ in order to adjust balance of carrier transporting capability of the compound according to the exemplary embodiment. Thus, it is also effective to appropriately select $L_1$ and $L_2$ when the compound according to the exemplary embodiment is used as a host material of an emitting layer in an organic EL device.

When $L_1$ and $L_2$ have a substituent, the substituent is exemplified by the groups for R in CR, which excludes a hydrogen atom.

$L_3$ represents a linking group represented by any one of the following formulae (2) to (4) or a composite linking group in which the linking groups represented by the formulae (2) to (4) are combined.

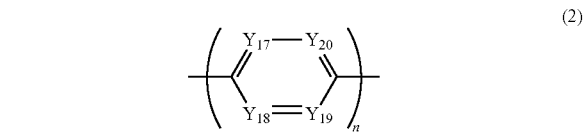

(2)

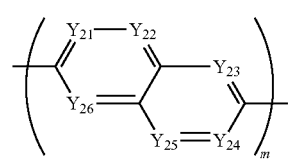

(3)

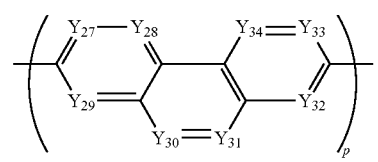

(4)

In the formulae (2) to (4), $Y_{17}$ to $Y_{34}$ each independently represent CH or a nitrogen atom. CH represents a hydrogen atom (H) bonded to a carbon atom (C).

In the formulae (2) to (4), n, m and p each independently represent an integer of 1 to 5. When $L_3$ is a composite linking group in which the linking groups represented by the formulae (2) to (4) are combined, n+m+p is an integer of 1 to 5, preferably an integer of 2 to 5, more preferably an integer of 2 to 4, further preferably 2 or 3. The composite linking group may be formed by any combination of the linking groups represented by the formulae (2) to (4). The composite linking group is preferably exemplified by the following combination.

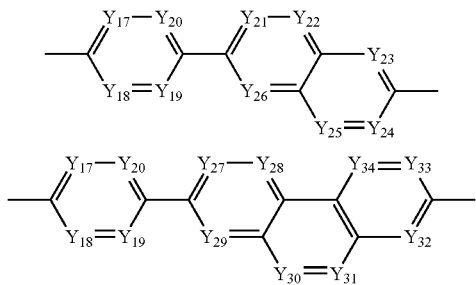

In the compound according to the exemplary embodiment, the compound represented by the formula (1) is preferably represented by any one of the following formulae (6) to (8).

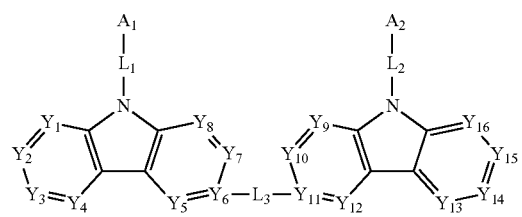

(6)

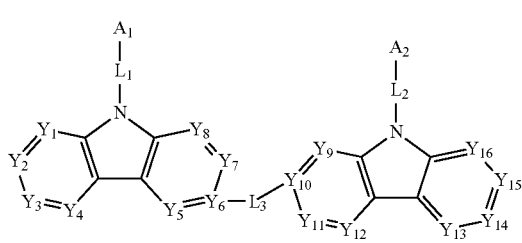

(7)

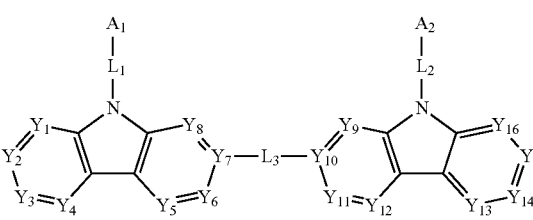

(8)

In the formula (6), $A_1$, $A_2$, $Y_1$ to $Y_5$, $Y_7$ to $Y_{10}$, $Y_{12}$ to $Y_{16}$, $L_1$, $L_2$ and $L_3$ represent the same as those in the formula (1). $Y_6$ and $Y_{11}$ represent a carbon atom.

In the formula (7), $A_1$, $A_2$, $Y_1$ to $Y_5$, $Y_7$ to $Y_9$, $Y_{11}$ to $Y_{16}$, $L_1$, $L_2$ and $L_3$ represent the same as those in the formula (1), and $Y_6$ and $Y_{10}$ represent a carbon atom.

In the formula (8), $A_1$, $A_2$, $Y_1$ to $Y_6$, $Y_8$ to $Y_9$, $Y_{11}$ to $Y_{16}$, $L_1$, $L_2$ and $L_3$ represent the same as those in the formula (1), and $Y_7$ and $Y_{10}$ represent a carbon atom.

In the compound according to the exemplary embodiment, among $Y_5$ to $Y_{12}$ in the formula (1), $Y_5$ to $Y_{12}$ bonded to $L_3$ are a carbon atom and the rest of $Y_5$ to $Y_{12}$ are CH. In this case, for instance, the formulae (6) to (8) are represented by the following formulae (6A) to (9A).

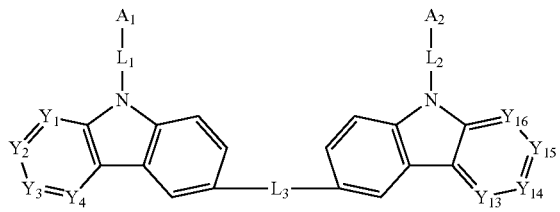

(6A)

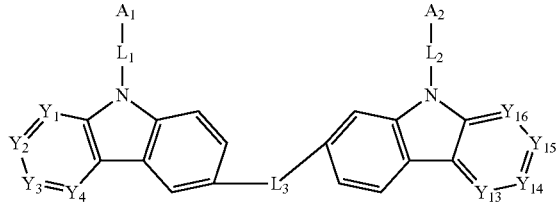

(7A)

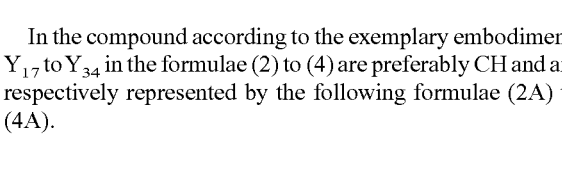

(8A)

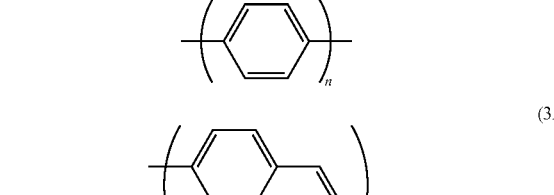

In the compound according to the exemplary embodiment, $Y_{17}$ to $Y_{34}$ in the formulae (2) to (4) are preferably CH and are respectively represented by the following formulae (2A) to (4A).

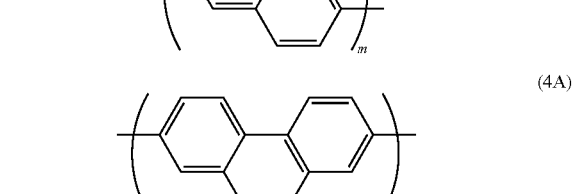

(2A)

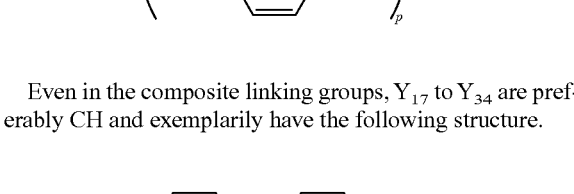

(3A)

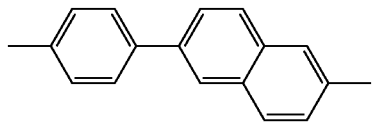

(4A)

Even in the composite linking groups, $Y_{17}$ to $Y_{34}$ are preferably CH and exemplarily have the following structure.

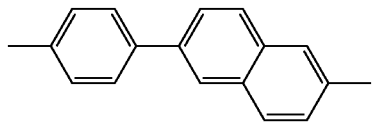

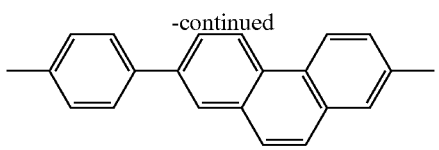

In the compound according to the exemplary embodiment, n in the formula (2), m in the formula (3) and p in the formula (4) preferably independently represent an integer of 1 to 3.

In the compound according to the exemplary embodiment, $L_3$ in the formula (1) is preferably the linking group represented by the formula (2), more preferably the linking group represented by the formula (2A). In the formula (2A), n is more preferably 1 or 2, particularly preferably 1.

Examples of the aromatic hydrocarbon group having 6 to 30 ring carbon atoms in the formulae (1) and (6) to (8) are a phenyl group, 1-naphthyl group, 2-naphthyl group, 1-anthryl group, 2-anthryl group, 9-anthryl group, benzanthryl group, 1-phenanthryl group, 2-phenanthryl group, 3-phenanthryl group, 4-phenanthryl group, 9-phenanthryl group, naphthacenyl group, pyrenyl group, 1-chrysenyl group, 2-chrysenyl group, 3-chrysenyl group, 4-chrysenyl group, 5-chrysenyl group, 6-chrysenyl group, benzo[c]phenanthryl group, benzo[g]chrysenyl group, 1-triphenylenyl group, 2-triphenylenyl group, 3-triphenylenyl group, 4-triphenylenyl group, 1-fluorenyl group, 2-fluorenyl group, 3-fluorenyl group, 4-fluorenyl group, 9-fluorenyl group, 2-spirobifluorenyl group, 3-spirobifluorenyl group, benzofluorenyl group, dibenzofluorenyl group, 2-biphenylyl group, 3-biphenylyl group, 4-biphenylyl group, o-terphenyl group, m-terphenyl-4-yl group, m-terphenyl-3-yl group, m-terphenyl-2-yl group, p-terphenyl-4-yl group, p-terphenyl-3-yl group, p-terphenyl-2-yl group, m-quarterphenyl group, 3-fluoranthenyl group, 4-fluoranthenyl group, 8-fluoranthenyl group, 9-fluoranthenyl group, benzofluoranthenyl group, o-tolyl group, m-tolyl group, p-tolyl group, 2,3-xylyl group, 3,4-xylyl group, 2,5-xylyl group, mesityl group, o-cumenyl group, m-cumenyl group, p-cumenyl group, p-t-butylphenyl group, p-(2-phenylpropyl)phenyl group, 4'-methylbiphenylyl group and 4"-t-butyl-p-terphenyl-4-yl group.

The aromatic hydrocarbon group in the formulae (1) and (6) to (8) preferably has 6 to 20 ring carbon atoms, more preferably 6 to 12 ring carbon atoms. Among the aromatic hydrocarbon group, a phenyl group, biphenyl group, naphthyl group, phenanthryl group, terphenyl group, fluorenyl group and triphenylenyl group are particularly preferable. In a 1-fluorenyl group, 2-fluorenyl group, 3-fluorenyl group and 4-fluorenyl group, a carbon atom at the ninth position is preferably substituted by a substituted or unsubstituted alkyl group having 1 to 30 carbon atoms or an aromatic hydrocarbon group having 6 to 30 ring carbon atoms in the formulae (1) and (6) to (8).

Examples of an aromatic heterocyclic group having 1 to 30 ring carbon atoms in the formulae (1) and (6) to (8) are a pyroryl group, pyrazinyl group, pyridinyl group, indolyl group, isoindolyl group, imidazolyl group, furyl group, benzofuranyl group, isobenzofuranyl group, dibenzofuranyl group, dibenzothiophenyl group, quinolyl group, isoquinolyl group, quinoxalinyl group, carbazolyl group, phenantridinyl group, acridinyl group, phenanthrolinyl group, phenazinyl group, phenothiazinyl group, phenoxazinyl group, oxazolyl group, oxadiazoyl group, furazanyl group, thienyl group, benzothiophenyl group and a group formed from a pyridine ring, pyrazine ring, pyrimidine ring, pyridazine ring, triazine ring, indole ring, quinoline ring, acridine ring, pirrolidine ring, dioxane ring, piperidine ring, morpholine ring, piperadine ring, carbazole ring, furan ring, thiophene ring, oxazole ring, oxadiazole ring, benzooxazole ring, thiazole ring, thiadiazole ring, benzothiazole ring, triazole ring, imidazole ring, benzoimidazole ring, pyrane ring and dibenzofuran ring.

Further specifically, examples of the above group are a 1-pyroryl group, 2-pyroryl group, 3-pyroryl group, pyrazinyl group, 2-pyridinyl group, 2-pyrimidinyl group, 4-pyrimidinyl group, 5-pyrimidinyl group, 6-pyrimidinyl group, 1,2,3-triazine-4-yl group, 1,2,4-triazine-3-yl group, 1,3,5-triazine-2-yl group, 1-imidazolyl group, 2-imidazolyl group, 1-pyrazolyl group, 1-indolidinyl group, 2-indolidinyl group, 3-indolidinyl group, 5-indolidinyl group, 6-indolidinyl group, 7-indolidinyl group, 8-indolidinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, azacarbazolyl-1-yl group, azacarbazolyl-2-yl group, azacarbazolyl-3-yl group, azacarbazolyl-4-yl group, azacarbazolyl-5-yl group, azacarbazolyl-6-yl group, azacarbazolyl-7-yl group, azacarbazolyl-8-yl group, azacarbazolyl-9-yl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-silafluorenyl group, 2-silafluorenyl group, 3-silafluorenyl group, 4-silafluorenyl group, 1-germafluorenyl group, 2-germafluorenyl group, 3-germafluorenyl group and 4-germafluorenyl group.

The heterocyclic group in the formulae (1) and (6) to (8) preferably has 1 to 20 ring carbon atoms, more preferably 1 to 14 ring carbon atoms. Preferable examples of the heterocyclic group are a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 2-pyridinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl group, 4-pyridinyl group, 1-imidazolyl group, 2-imidazolyl group, 2-quinolyl group, 3-quinolyl group, 4-quinolyl group, 5-quinolyl group, 6-quinolyl group, 7-quinolyl group, 8-quinolyl group, phenanthrolinyl group and a group formed from a triazine ring or a benzoimidazole ring.

The alkyl group in the formulae (1) and (6) to (8) may be linear, branched or cyclic. Examples of the linear or branched alkyl group are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 1,2-dinitroethyl group, 2,3-dinitro-t-butyl group and 1,2,3-trinitropropyl group.

Examples of the cyclic alkyl group (cycloalkyl group) are a cyclopropyl group, cyclobutyl group, cyclopentyl group, cyclohexyl group, 4-methylcyclohexyl group, 1-adamantyl group, 2-adamantyl group, 1-norbornyl group and 2-norbornyl group.

The linear or branched alkyl group in the formulae (1) and (6) to (8) preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group and n-hexyl group are preferable.

The cycloalkyl group in the formulae (1) and (6) to (8) preferably has 3 to 10 ring carbon atoms, more preferably 5 to 8 ring carbon atoms. Among the cycloalkyl group, a cyclopentyl group and a cyclohexyl group are preferable.

The haloalkyl group having 1 to 30 carbon atoms in the formulae (1) and (6) to (8) is exemplified by a haloalkyl group provided by substituting the alkyl group having 1 to 30 carbon atoms with one or more halogen groups. Specific examples of the haloalkyl group are a fluoromethyl group, difluoromethyl group, trifluoromethyl group, fluoroethyl group and trifluoromethylmethyl group.

The alkenyl group having 2 to 30 carbon atoms in the formulae (1) and (6) to (8) may be linear, branched or cyclic. Examples of the alkenyl group are vinyl, propenyl, butenyl, oleyl, eicosapentaenyl, docosahexaenyl, styryl, 2,2-diphenylvinyl, 1,2,2-triphenylvinyl and 2-phenyl-2-propenyl, among which a vinyl group is preferable.

The alkynyl group in the formulae (1) and (6) to (8) may be linear, branched or cyclic. Examples of the alkynyl group are ethynyl, propynyl and 2-phenylethynyl, among which an ethynyl group is preferable.

The alkylsilyl group having 3 to 30 carbon atoms in the formulae (1) and (6) to (8) is exemplified by a trialkylsilyl group having the examples of the alkyl group having 1 to 30 carbon atoms. Specific examples of the alkylsilyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyldimethylsilyl group, propyldimethylsilyl group and triisopropylsilyl group. Three alkyl groups in the trialkylsilyl group may be the same or different.

The dialkylarylsilyl group having 8 to 40 carbon atoms in the formulae (1) and (6) to (8) is exemplified by a dialkylarylsilyl group having two of the examples of the alkyl group having 1 to 30 carbon atoms and one of the aromatic hydrocarbon group having 6 to 30 ring carbon atoms. The dialkylarylsilyl group preferably has 8 to 30 carbon atoms. Two alkyl groups in the dialkylarylsilyl group may be the same or different.

The alkyldiarylsilyl group having 13 to 50 carbon atoms in the formulae (1) and (6) to (8) is exemplified by an alkyldiarylsilyl group having one of the examples of the alkyl group having 1 to 30 carbon atoms and two of the aromatic hydrocarbon group having 6 to 30 ring carbon atoms. The dialkylarylsilyl group preferably has 13 to 30 carbon atoms. Two aryl groups in the alkyldiarylsilyl group may be the same or different.

The triarylsilyl group having 18 to 60 carbon atoms in the formulae (1) and (6) to (8) is exemplified by a triarylsilyl group having three of the aromatic hydrocarbon group having 6 to 30 ring carbon atoms. The triarylsilyl group preferably has 18 to 30 carbon atoms. Three aromatic hydrocarbon groups in the triarylsilyl group may be the same or different.

The alkoxy group having 1 to 30 carbon atoms in the formulae (1) and (6) to (8) is represented by —$OY^1$. $Y^1$ is exemplified by the alkyl group having 1 to 30 carbon atoms. Examples of the alkoxy group are a methoxy group, ethoxy group, propoxy group, butoxy group, pentyloxy group and hexyloxy group.

The haloalkoxy group having 1 to 30 carbon atoms in the formulae (1) and (6) to (8) is exemplified by a haloalkoxy group provided by substituting the alkoxy group having 1 to 30 carbon atoms with one or more halogen groups.

The aralkyl group having 7 to 30 carbon atoms in the formulae (1) and (6) to (8) is represented by —$Y^2$—$Z^2$. $Y^2$ is exemplified by an alkylene group corresponding to the alkyl group having 1 to 30 carbon atoms. $Z^2$ is exemplified by the examples of the aromatic hydrocarbon group having 6 to 30 ring carbon atoms. In the aralkyl group, an aromatic hydrocarbon group moiety has 6 to 30 carbon atoms, preferably 6 to 20 carbon atoms, more preferably 6 to 12 carbon atoms. In the aralkyl group, an alkyl group moiety has 1 to 30 carbon atoms, preferably 1 to 20 carbon atoms, more preferably 1 to 10 carbon atoms, further preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrorylmethyl group, 2-(1-pyroryl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group.

The aryloxy group having 6 to 30 ring carbon atoms in the formulae (1) and (6) to (8) is represented by —$OZ^3$. $Z^3$ is exemplified by the aromatic hydrocarbon group having 6 to 30 ring carbon atoms or the following monocyclic group and fused cyclic group. The aryloxy group is exemplified by a phenoxy group.

Examples of the halogen atom in the formulae (1) and (6) to (8) are fluorine, chlorine, bromine and iodine, among which fluorine is preferable.

In the invention, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a hetero ring including a saturated ring, unsaturated ring, or aromatic ring.

A "hydrogen atom" means isotopes having different neutron numbers and specifically encompasses protium, deuterium and tritium.

Examples of the substituent meant by "substituted or unsubstituted" are the above-described aromatic hydrocarbon group, aromatic heterocyclic group, alkyl group (linear or branched alkyl group, cycloalkyl group and haloalkyl group), alkoxy group, aryloxy group, aralkyl group, haloalkoxy group, alkylsilyl group, dialkylarylsilyl group, alkyldiarylsilyl group, triarylsilyl group, halogen atom, cyano group, hydroxyl group, nitro group and carboxy group. In addition, the alkenyl group and alkynyl group are also usable.

In the above-described substituents, the aromatic hydrocarbon group, aromatic heterocyclic group, alkyl group, halogen atom, alkylsilyl group, arylsilyl group and cyano group are preferable. Preferable ones of the specific examples of each substituent are further preferable.

"Unsubstituted" in "substituted or unsubstituted" means that a group is not substituted by the above-described substituents but bonded with a hydrogen atom. In the invention, "a to b carbon atoms" in the description of "substituted or unsubstituted X group having a to b carbon atoms" represent carbon atoms of an unsubstituted X group and does not include carbon atoms of a substituted X group.

In a later-described compound or a partial structure thereof, the same applies to the description of "substituted or unsubstituted."

The compound according to the exemplary embodiment is provided by two carbazole derivatives (carbazoles or azacarbazoles) (hereinafter, occasionally abbreviated by Cz) respectively bonded to specific positions of the unsubstituted linking group or composite linking group represented by $L_3$. Accordingly, in the biscarbazole derivative of the compound according to the exemplary embodiment, a steric hindrance between $L_3$ and Cz is small, flatness therebetween is kept, and a π conjugated system in a moiety of Cz-$L_3$-Cz is extendible. By the extension of the π conjugated system, a HOMO (highest occupied molecular orbital) is extended over the moiety of Cz-$L_3$-Cz. Accordingly, when the biscarbazole derivative of the compound according to the exemplary embodiment forms films in a laminate in the organic thin-film layer of the organic EL device, overlapping of π electrons between molecules of the biscarbazole derivative is increased to improve the hole transporting capability of the organic thin-film layer.

Figure 2A:
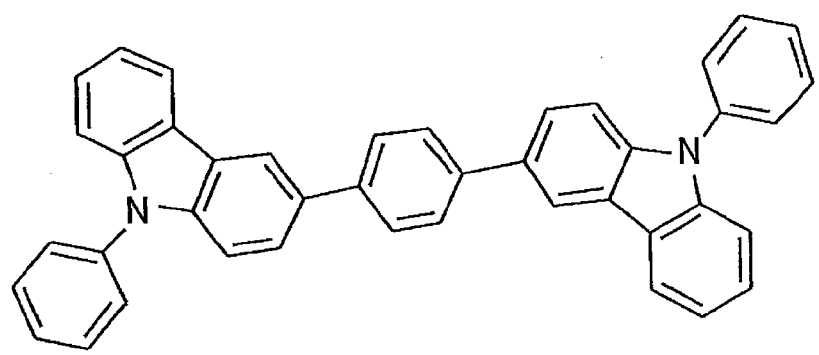
FIG. 2A shows a chemical formula of a compound A.
Figure 2B:
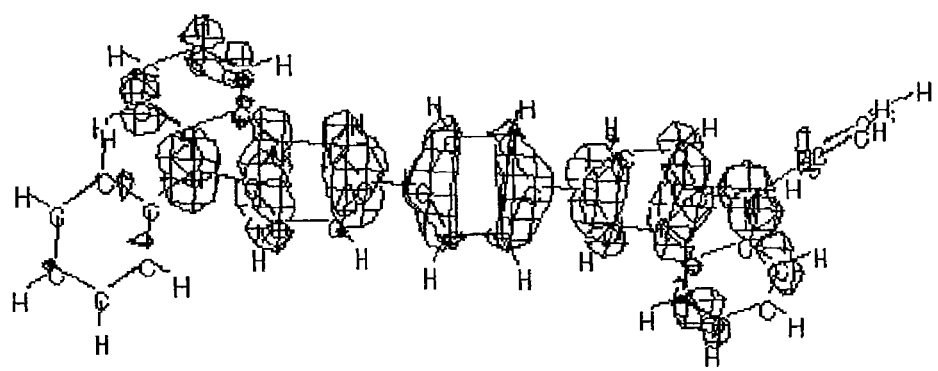
FIG. 2B shows a molecular orbital view of the compound A.
Figure 3A:
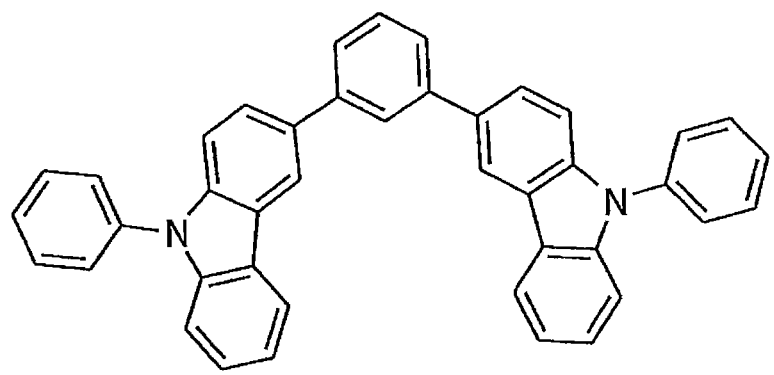
FIG. 3A shows a chemical formula of a compound B.
Figure 3B:
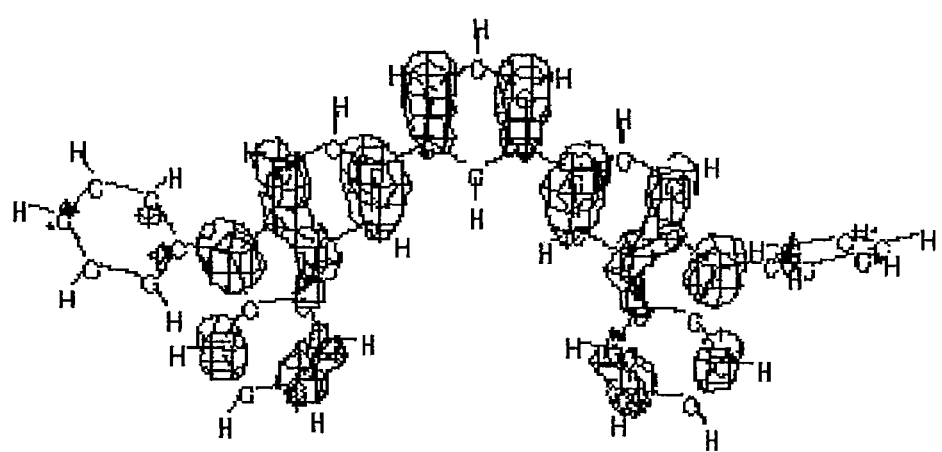
FIG. 3B shows a molecular orbital view of the compound B.

In the compound according to the exemplary embodiment, for instance, when $L_3$ is a phenylene group, one of Cz is bonded to a p-position (para-position) of $L_3$ bonded to the other Cz. Accordingly, as compared with bonding of Cz at m-positions (meta-positions) or o-positions (ortho-positions), conjugation of π electrons is less likely to be broken in bonding of Cz at the p-position, so that the π conjugated system is extendible. This will be described with reference to FIGS. 2A, 2B, 3A and 3B. FIG. 2A shows a compound A. In the compound A, one of Cz is bonded to a p-position (para-position) of a phenylene group bonded to the other Cz. FIG. 2B shows a molecular orbital view of the compound A. FIG. 3A shows a compound B. In the compound B, one of Cz is bonded to an m-position (meta-position) of the phenylene group bonded to the other Cz. FIG. 3B shows a molecular orbital view of the compound B. In comparison between the molecular orbital views of the compounds A and B, in the compound B, conjugation of the π electrons is broken at positions of carbon atoms at second and fifth positions of the phenylene group as shown in FIG. 3B. On the other hand, in the compound A, conjugation of the π electrons is extended over the phenylene group as shown in FIG. 2B.

The biscarbazole derivative of the compound according to the exemplary embodiment has a suitable triplet energy as a phosphorescent host material by being bonded through $L_3$ having a specific structure and represented by any one of the formulae (2) to (4). Accordingly, the biscarbazole derivative of the compound according to the exemplary embodiment is suitable for the phosphorescent host material, which is particularly suitable for a phosphorescent dopant material exhibiting red, yellow and green emissions.

The compound according to the exemplary embodiment has a substituted or unsubstituted nitrogen-containing aromatic heterocyclic group for at least one of $A_1$ and $A_2$. Accordingly, when the organic thin-film layer of the organic EL device contains the compound according to the exemplary embodiment, electron injection capability of the organic thin-film layer is improved. Thus, when the emitting layer of the organic EL device contains the compound according to the exemplary embodiment, carrier balance in the emitting layer is improved, whereby a luminous efficiency of the organic EL device is improvable.

Moreover, by introducing a substituted or unsubstituted nitrogen-containing aromatic heterocyclic group at an N position (9th position) of carbazole or azacarbazole, a LUMO (lowest unoccupied molecular orbital) is distributed in the nitrogen-containing aromatic heterocyclic group. As a result, the HOMO in the moiety of Cz-$L_3$-Cz and the LUMO of the nitrogen-containing aromatic heterocyclic group can be separated from each other. Consequently, the biscarbazole derivative of the compound according to the exemplary embodiment is considered to exhibit an excellent resistance to holes and electrons.

Furthermore, in the compound according to the exemplary embodiment, one of $A_1$ and $A_2$ in the formula (1) is preferably a substituted or unsubstituted aromatic heterocyclic group having 1 to 30 ring carbon atoms, and the other of $A_1$ and $A_2$ is preferably a substituted or unsubstituted aromatic hydrocarbon group having 6 to 30 ring carbon atoms. Specifically, (a) $A_1$ in the formula (1) is preferably a substituted or unsubstituted aromatic heterocyclic group having 1 to 30 ring carbon atoms, and $A_2$ in the formula (1) is preferably a substituted or unsubstituted aromatic hydrocarbon group having 6 to 30 ring carbon atoms.

Alternatively, (b) $A_2$ in the formula (1) is preferably a substituted or unsubstituted aromatic heterocyclic group having 1 to 30 ring carbon atoms, and $A_1$ in the formula (1) is preferably a substituted or unsubstituted aromatic hydrocarbon group having 6 to 30 ring carbon atoms.

Examples of specific structures of the compounds according to this exemplary embodiment represented by the formulae (1) and (6) to (8) are as follows. However, the invention is not limited to the compounds having these structures.

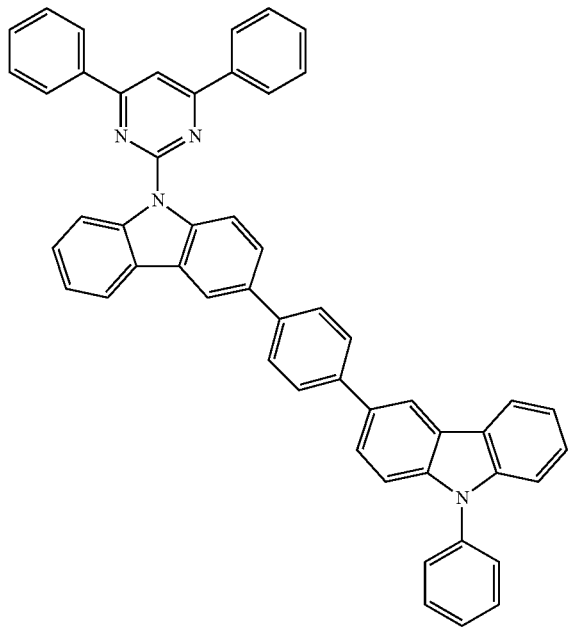
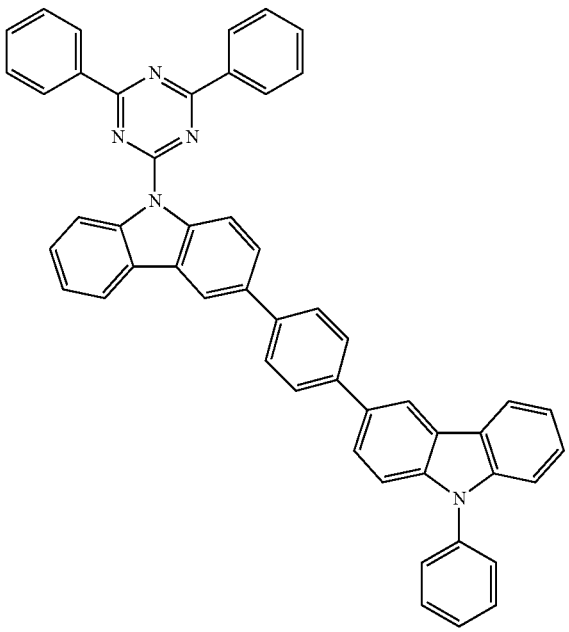

-continued
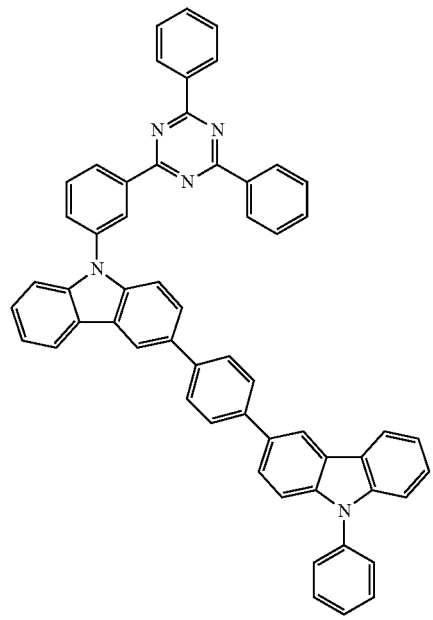
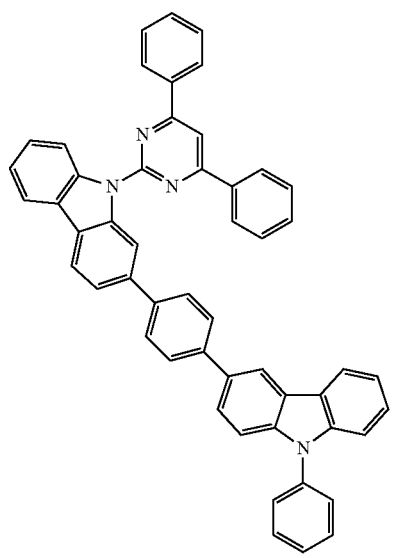
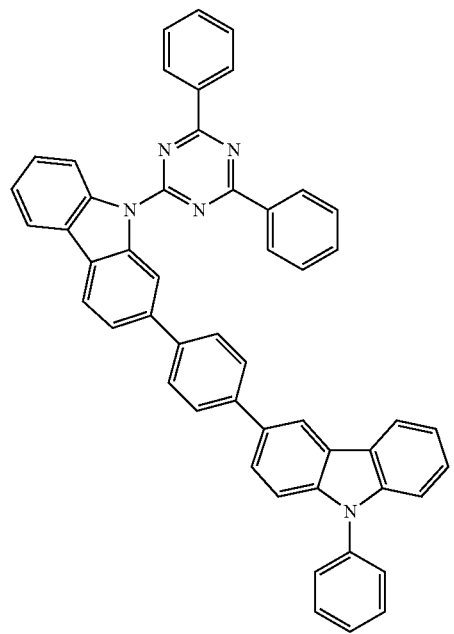
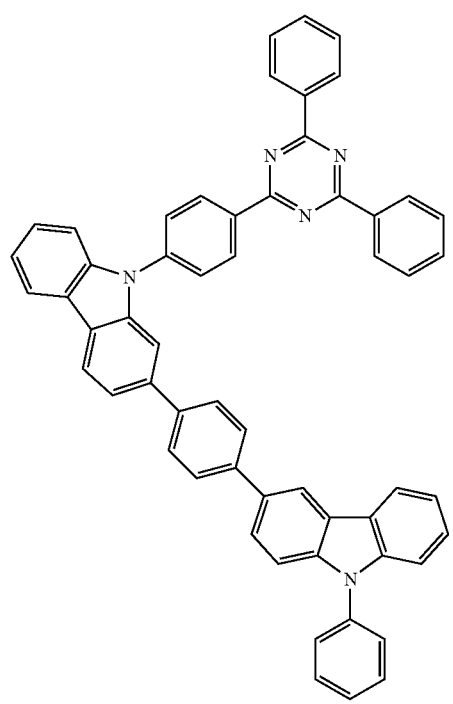

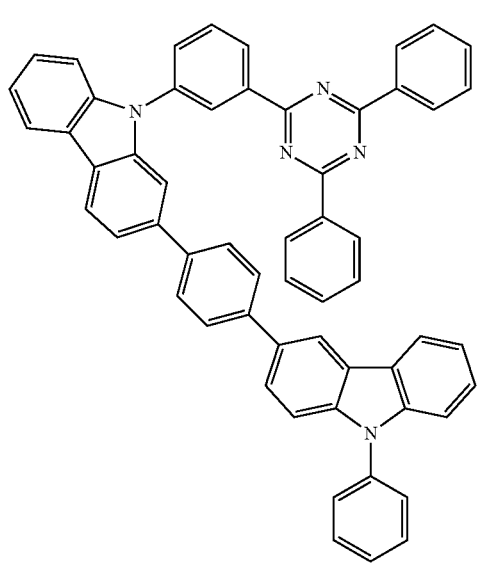
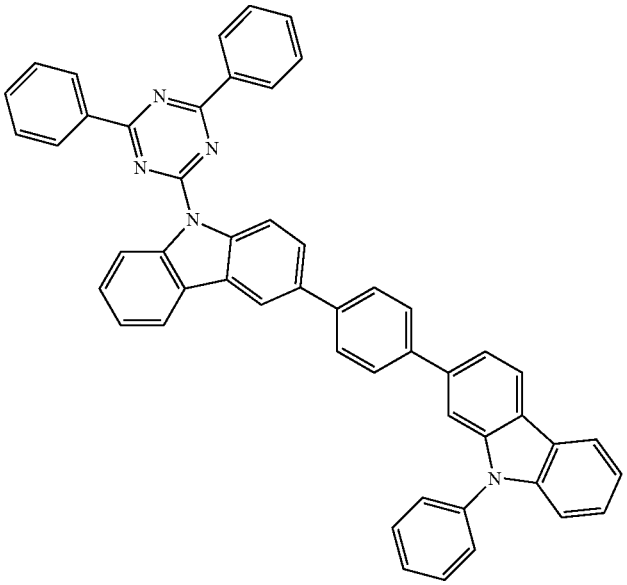
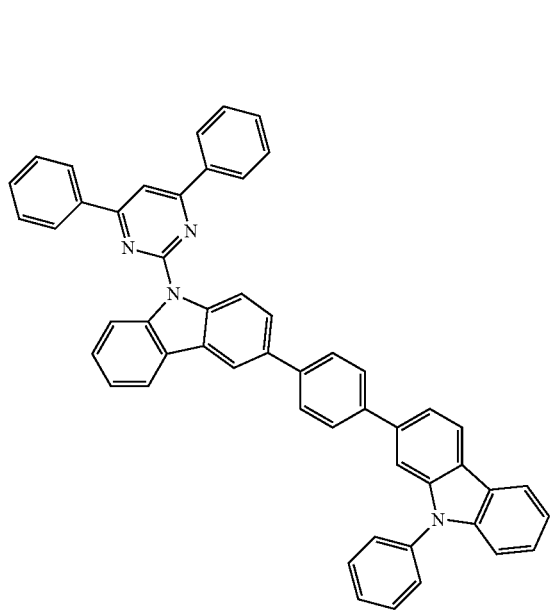
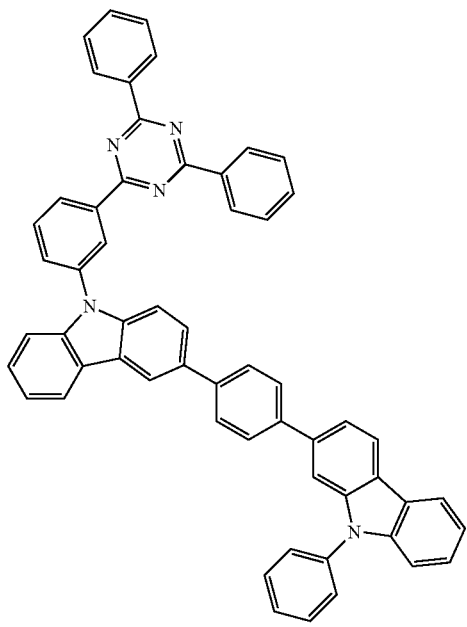

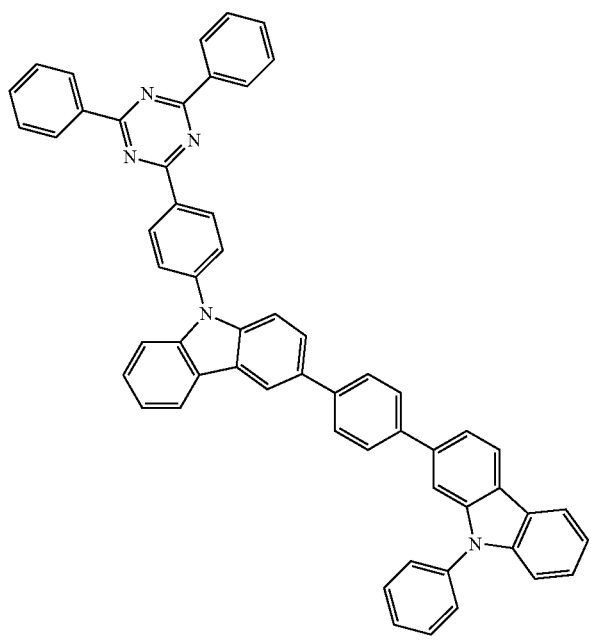
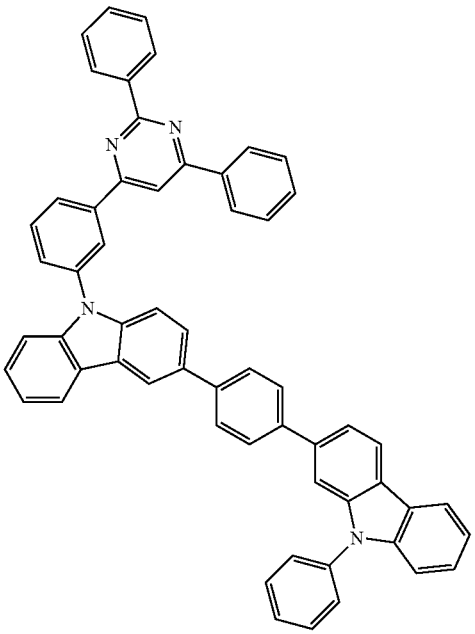
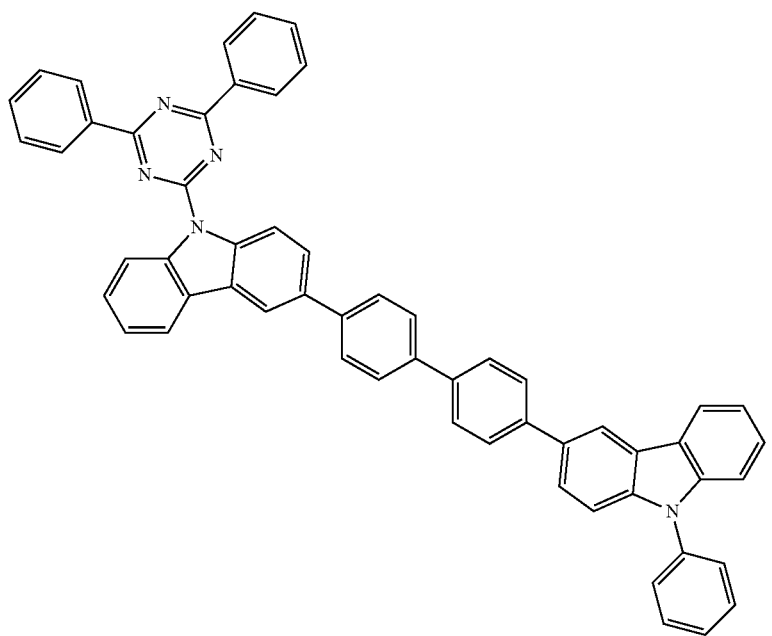

-continued
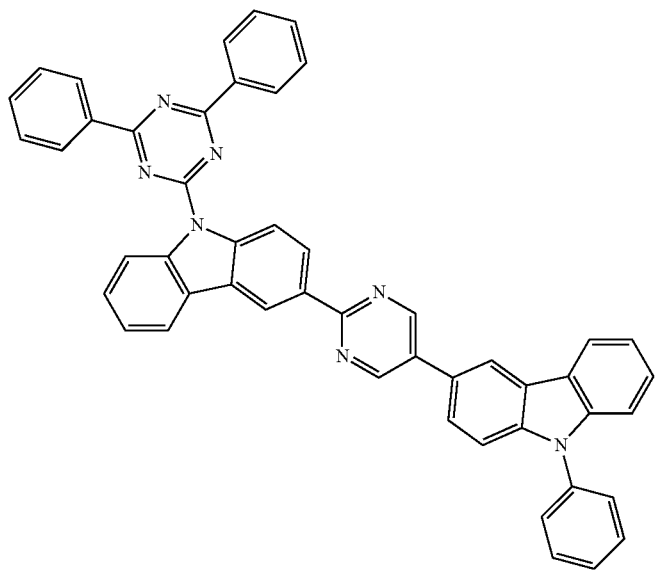

-continued
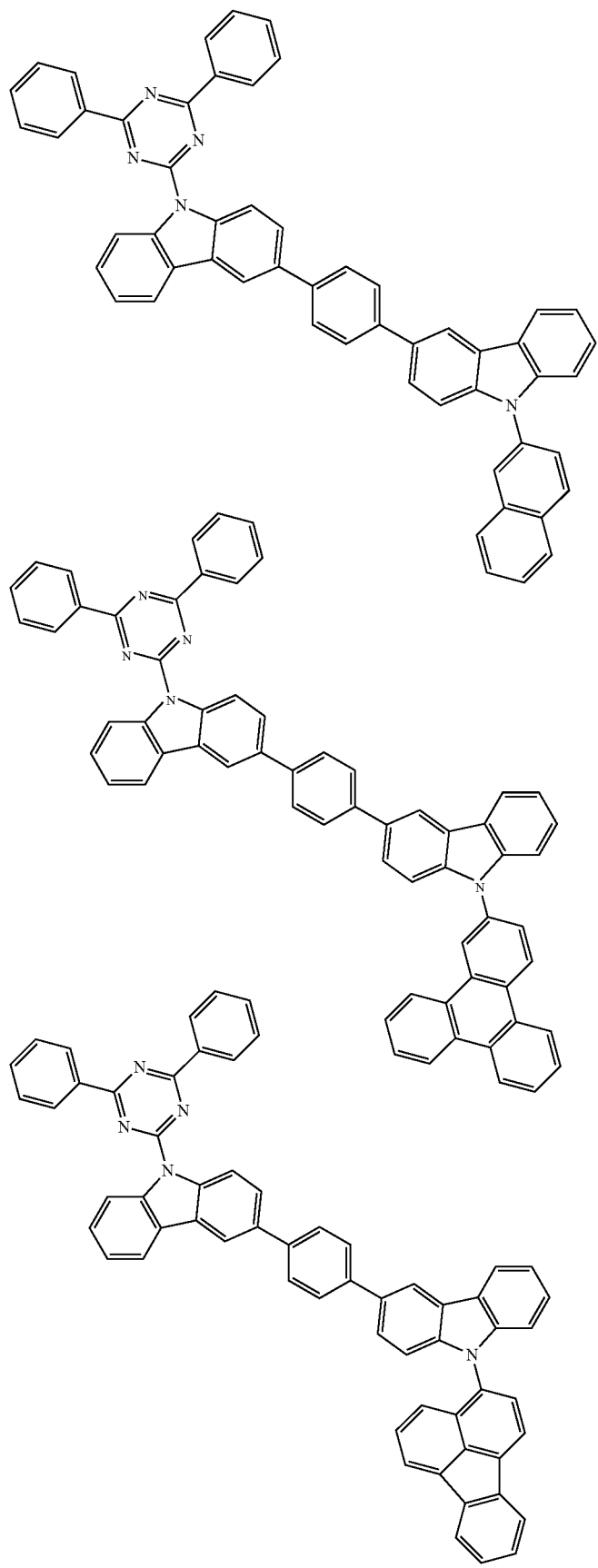

-continued
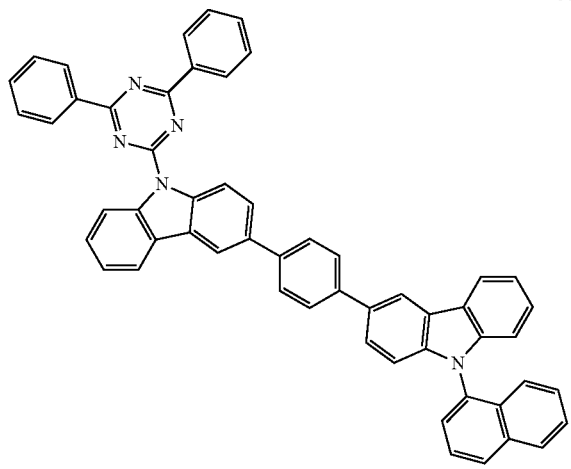
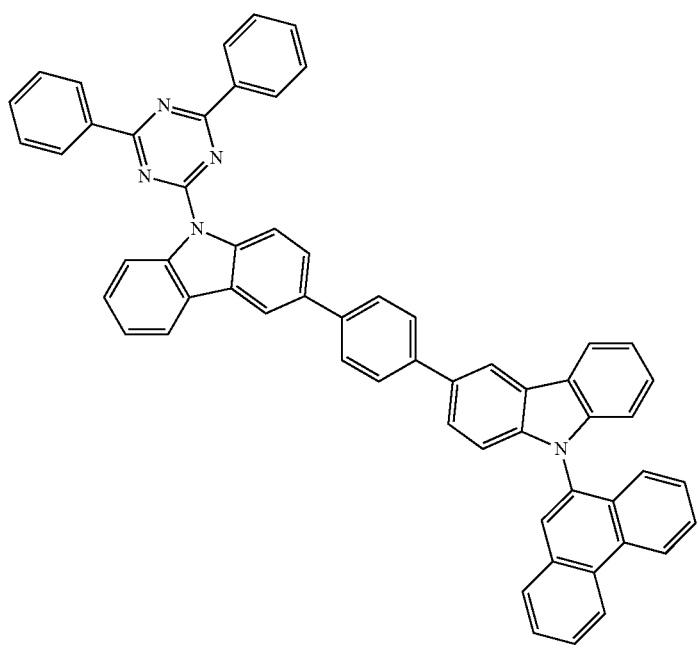
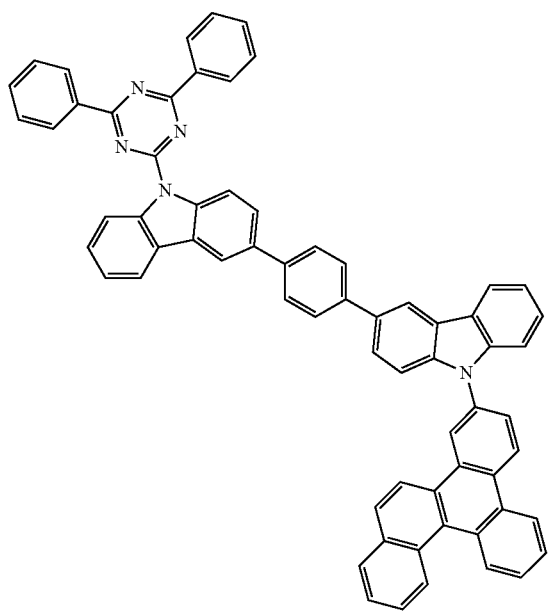

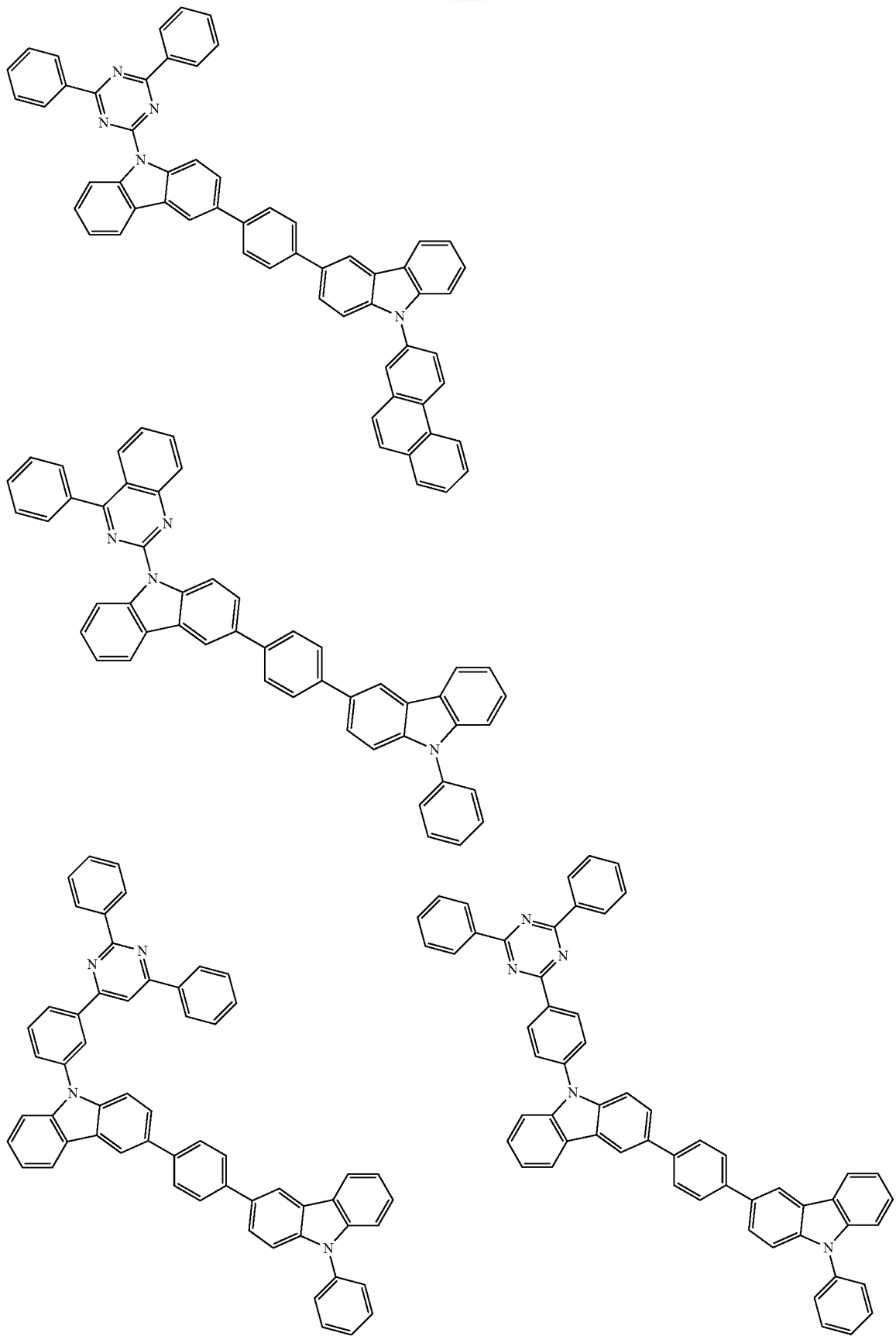

-continued
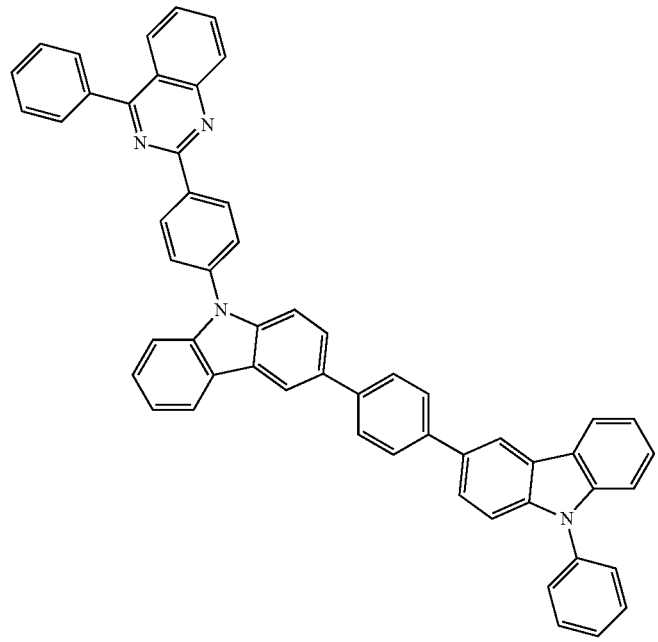
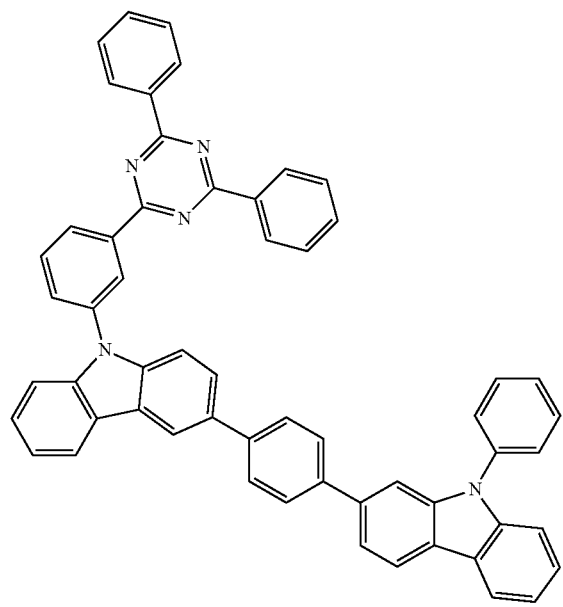
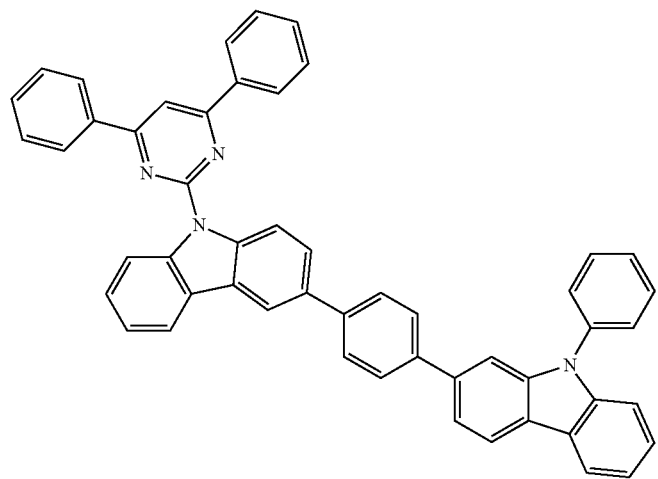

-continued
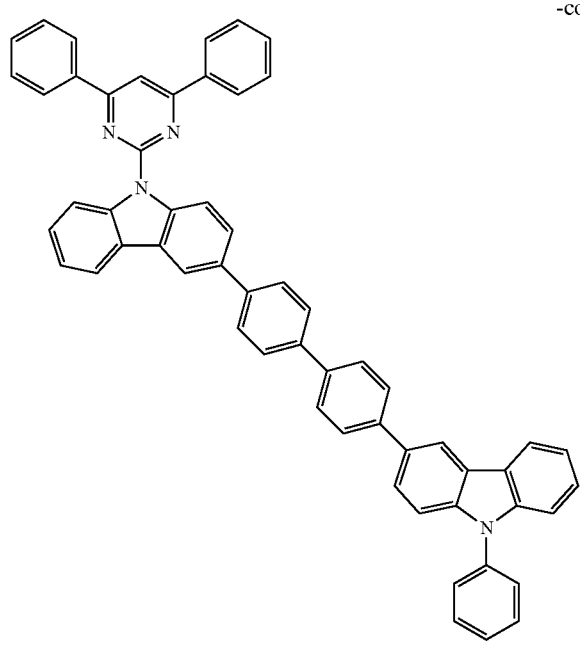
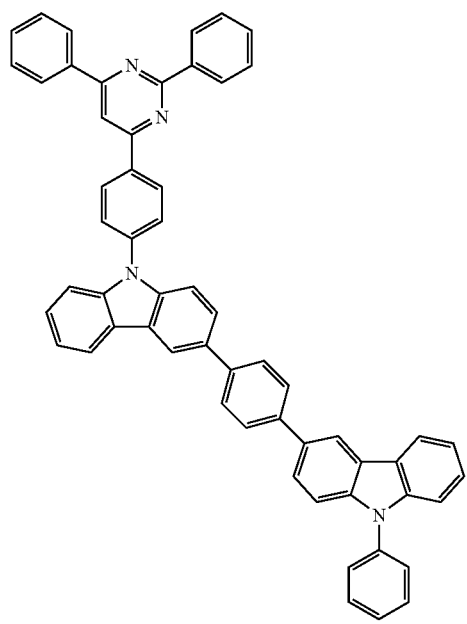
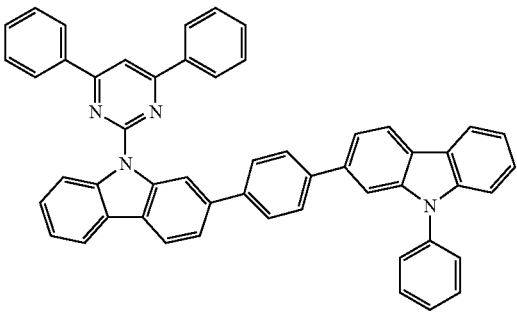
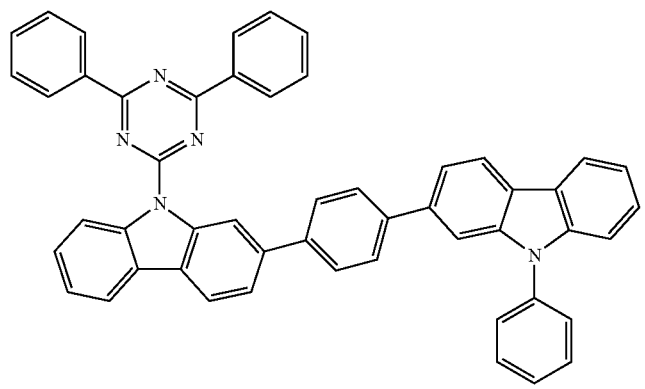

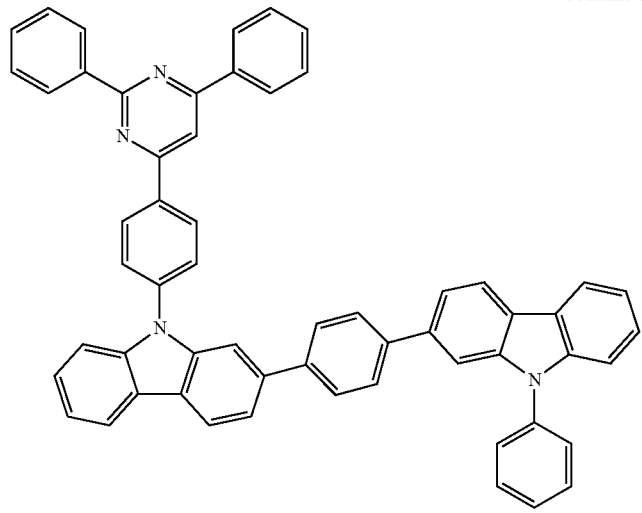
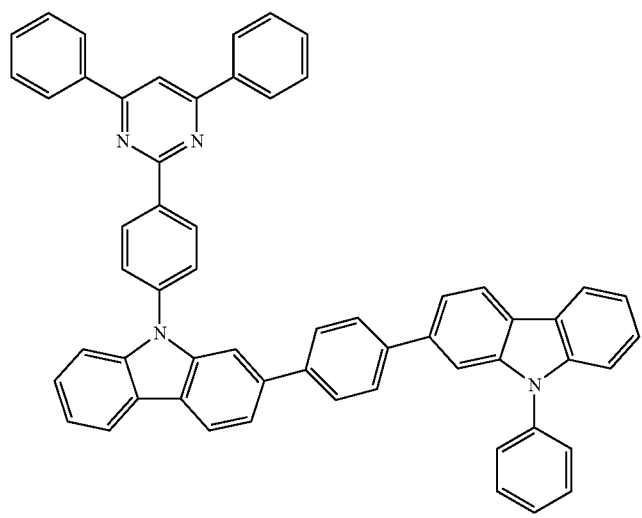
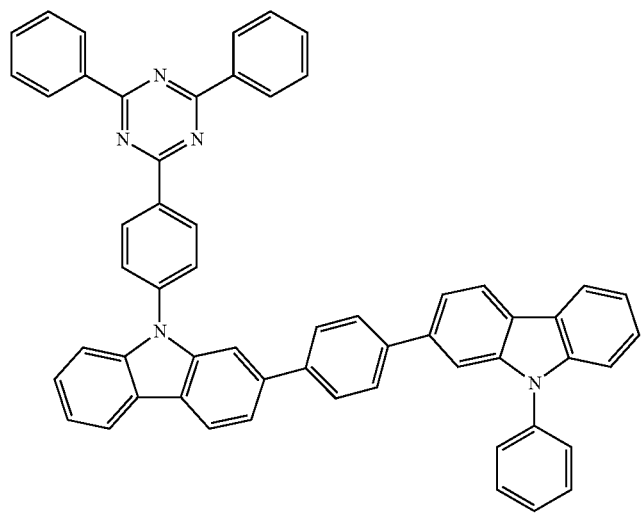

-continued
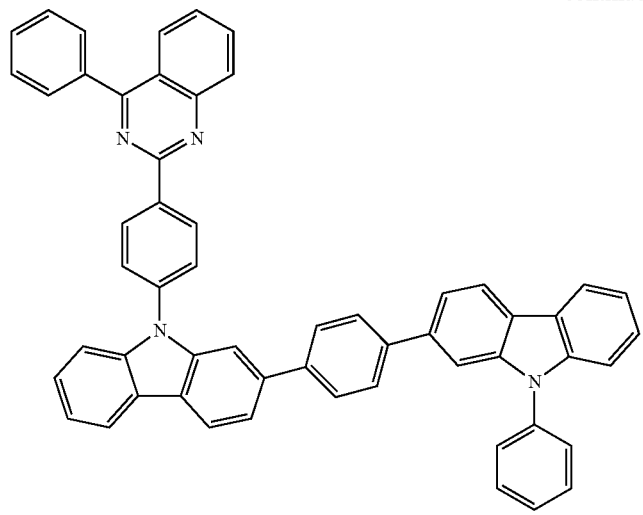
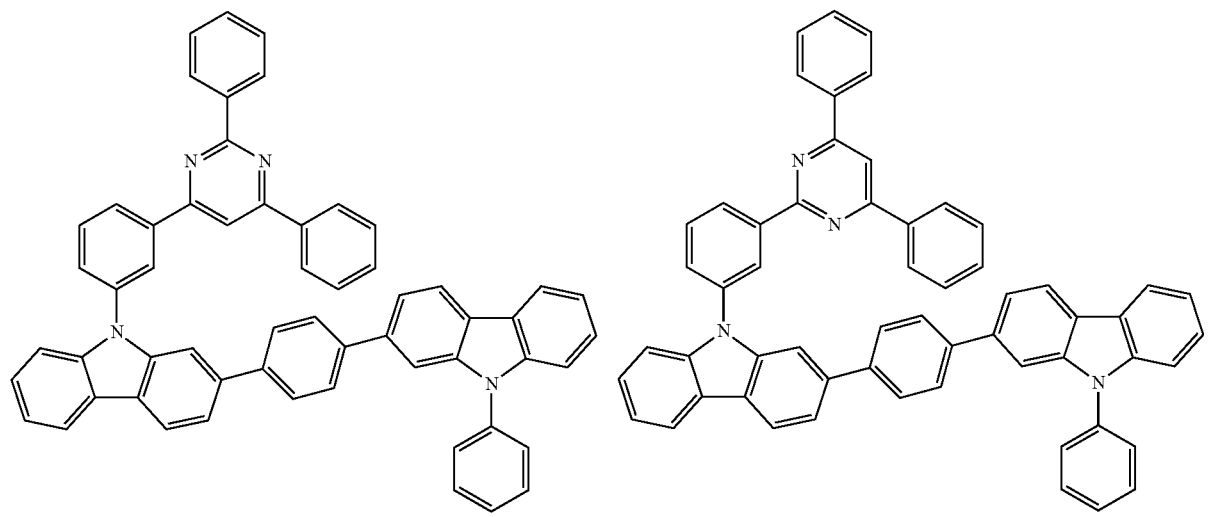
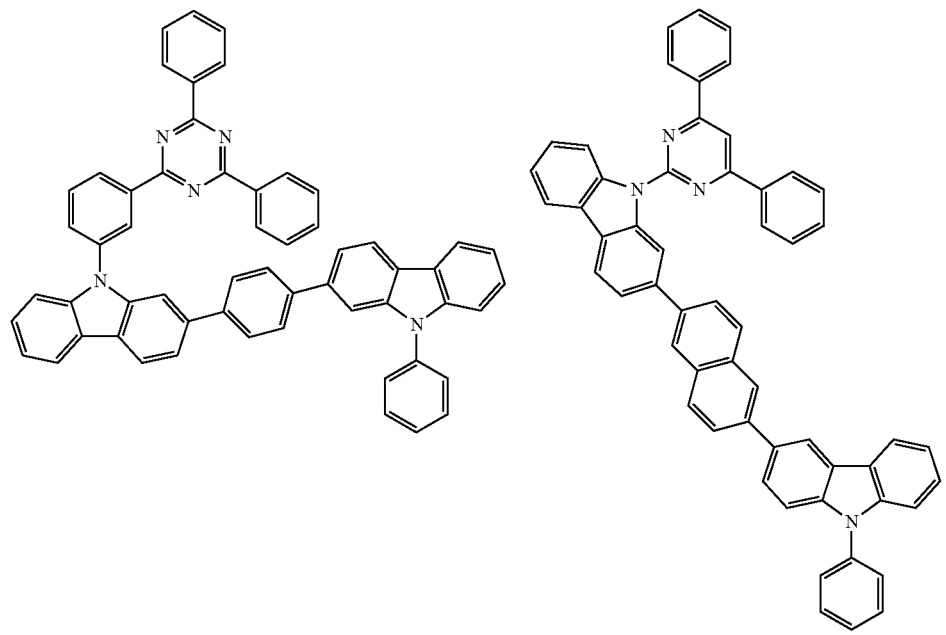

-continued
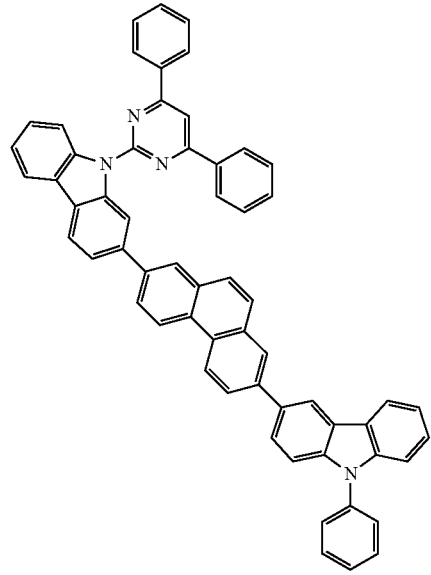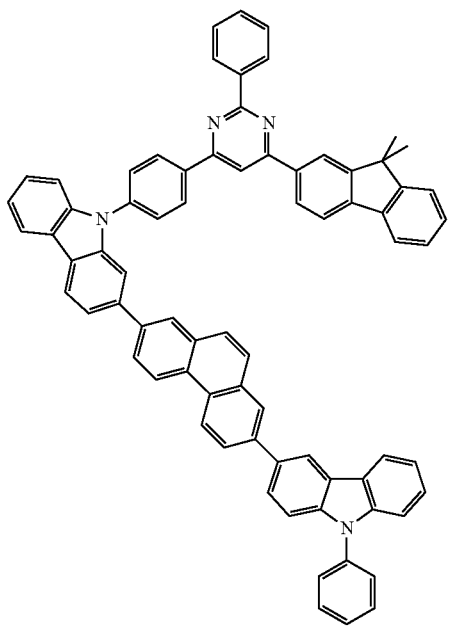
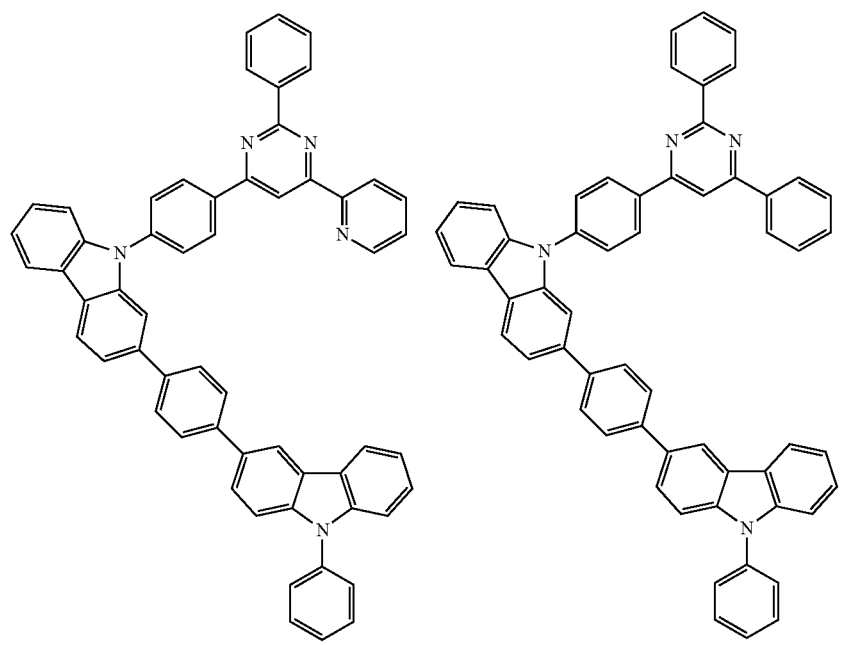

-continued
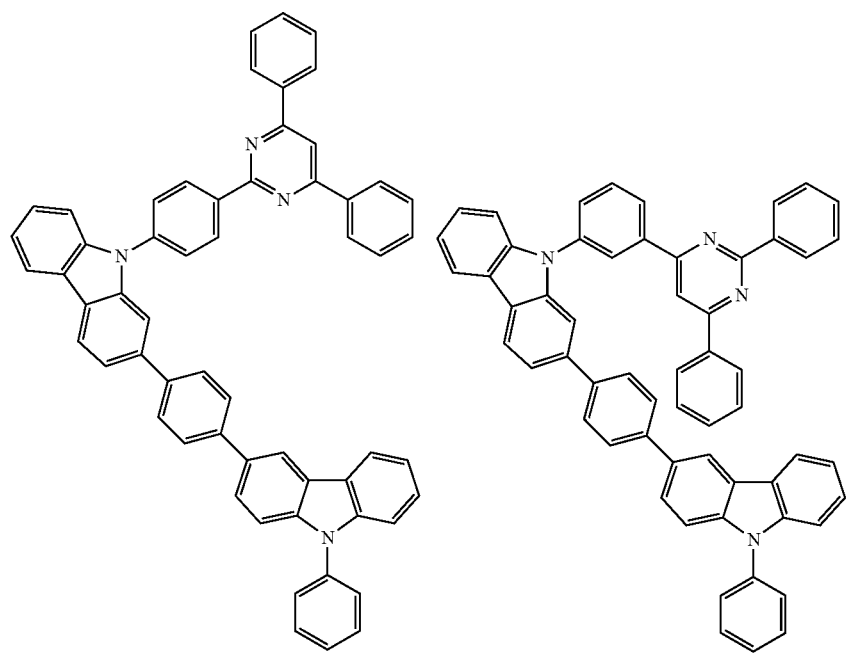
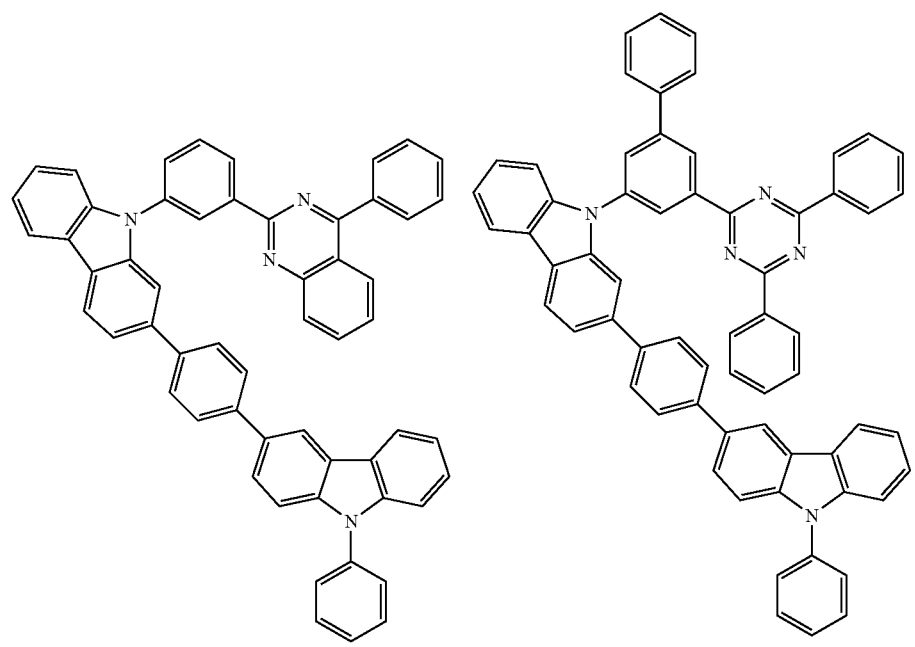

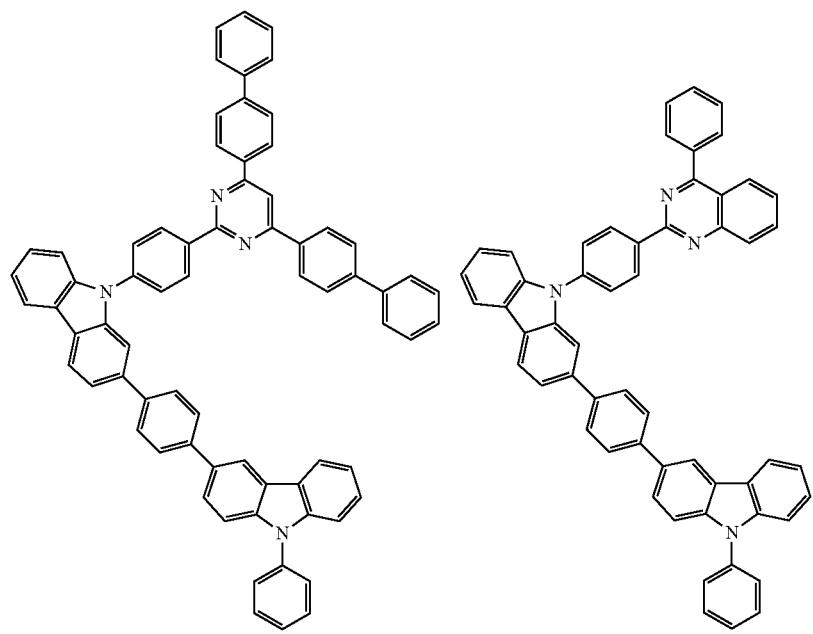
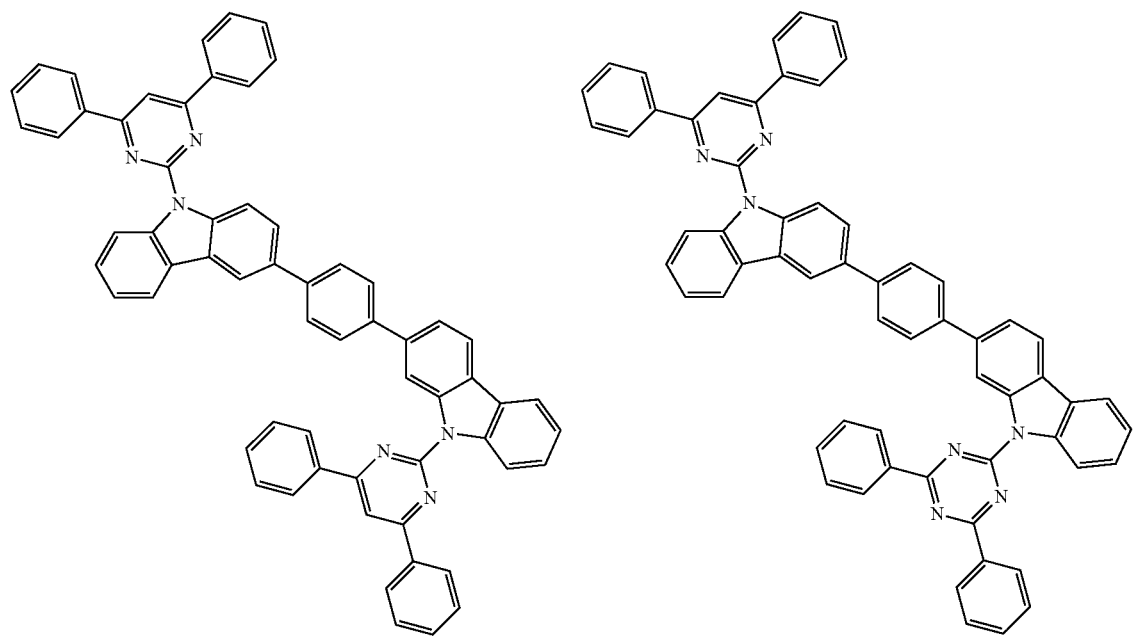

-continued
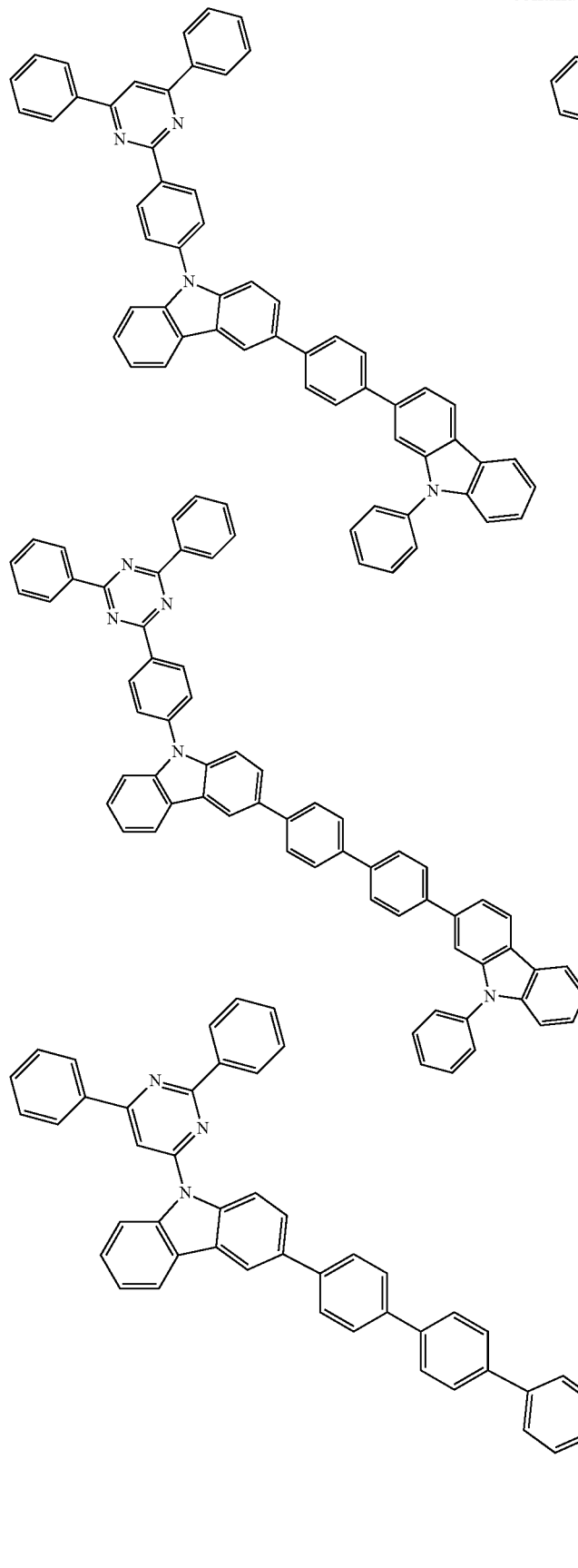
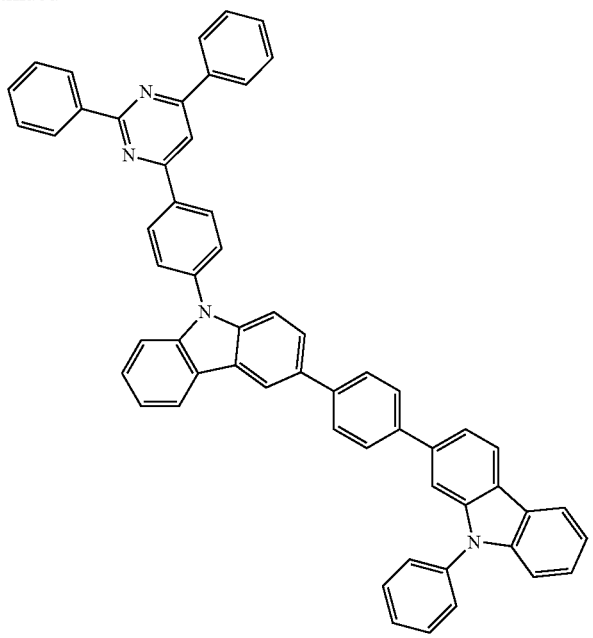

-continued
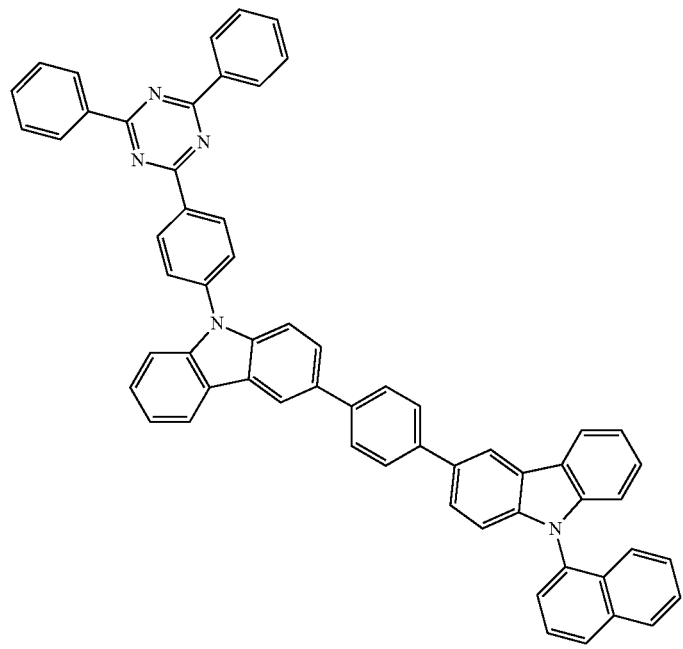
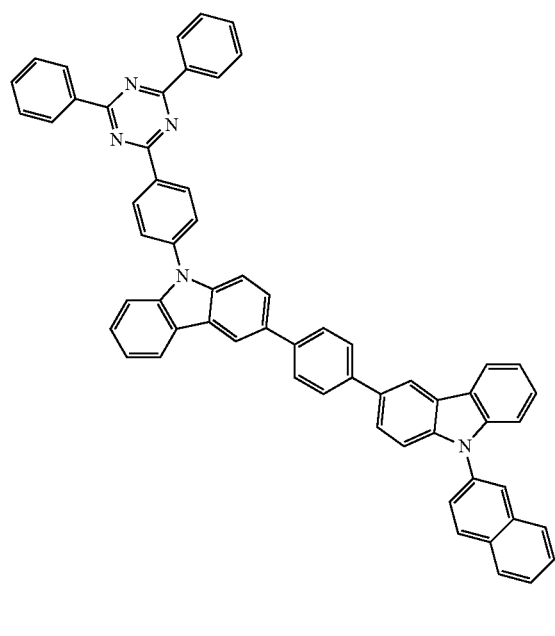

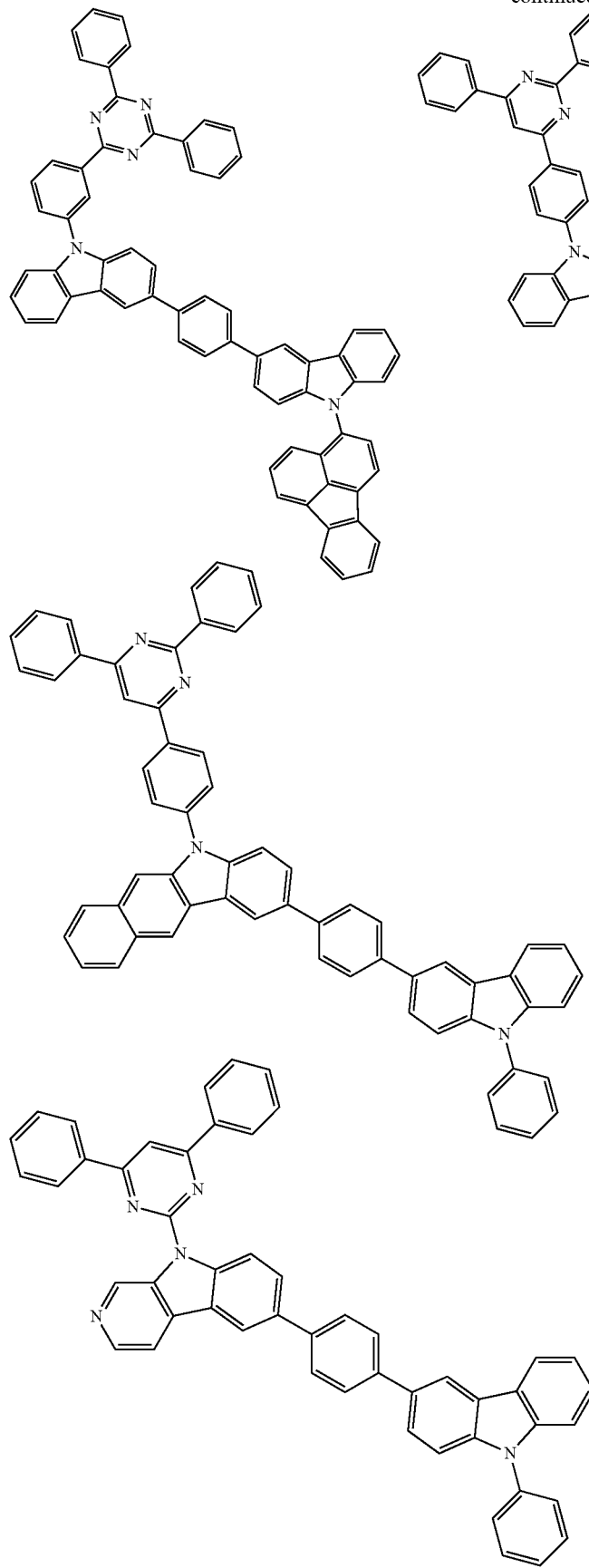
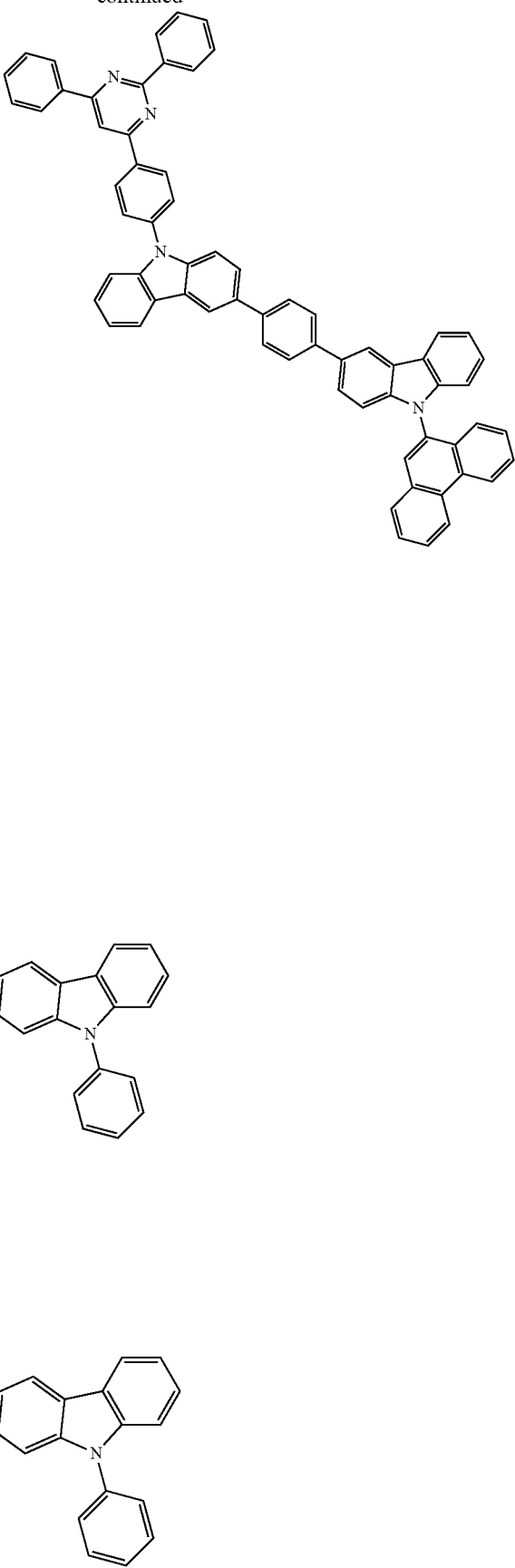

-continued
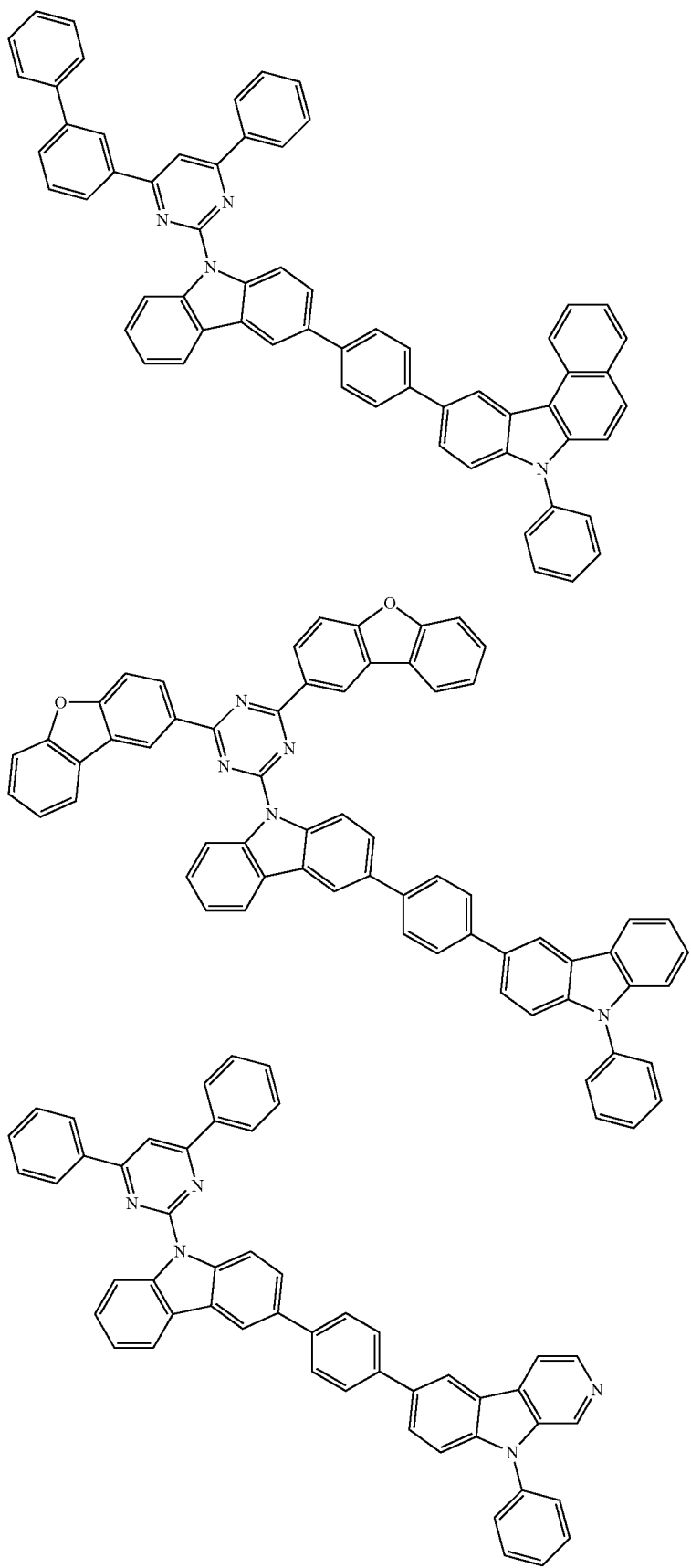

-continued
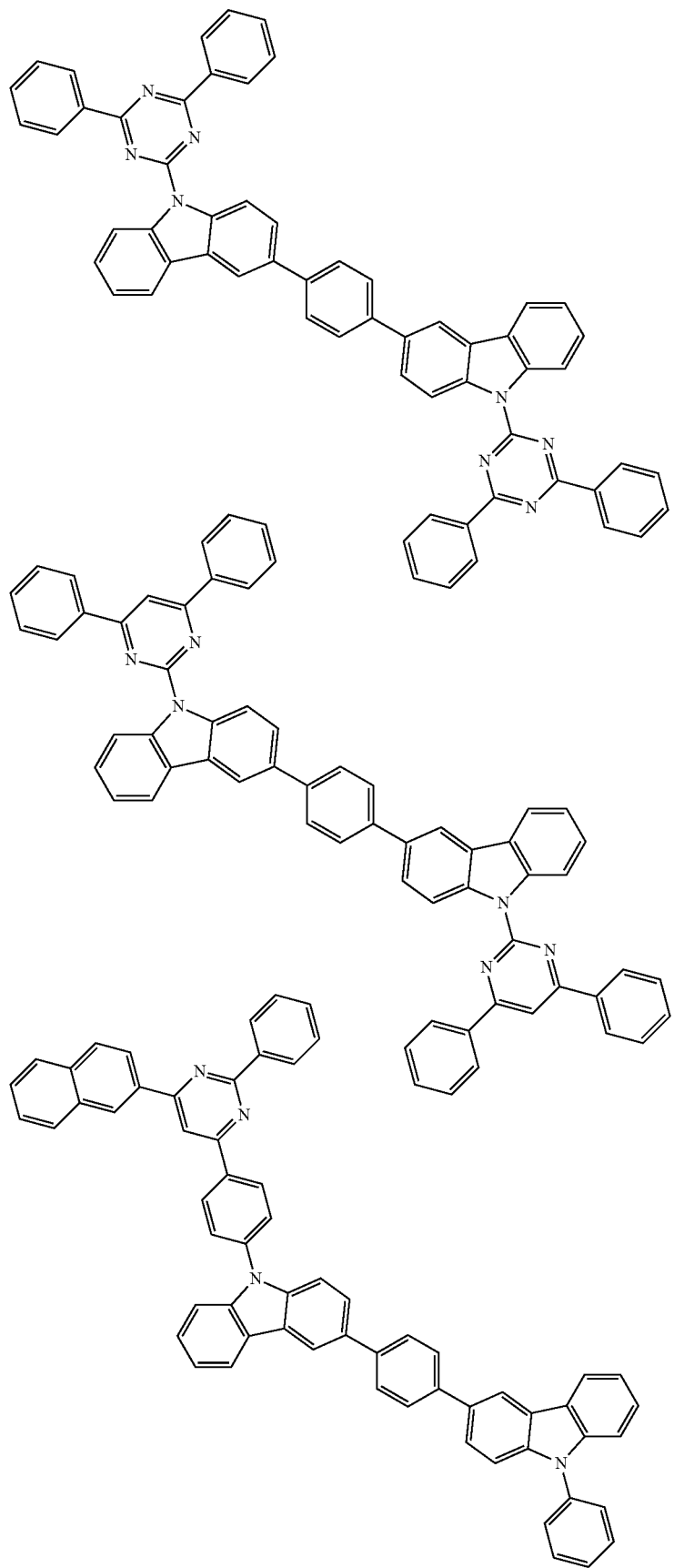

-continued
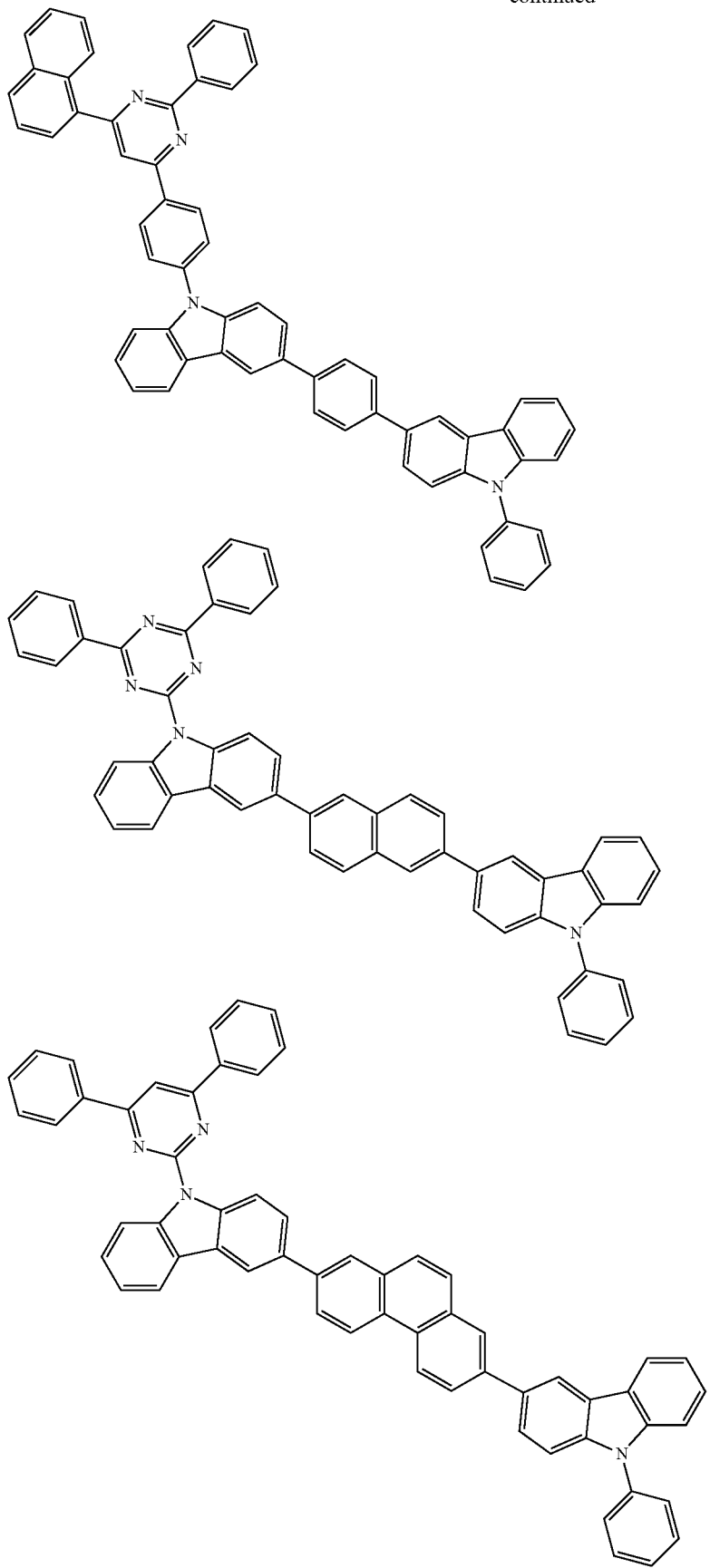

-continued
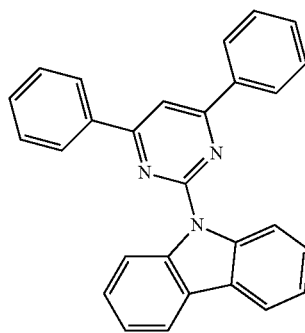
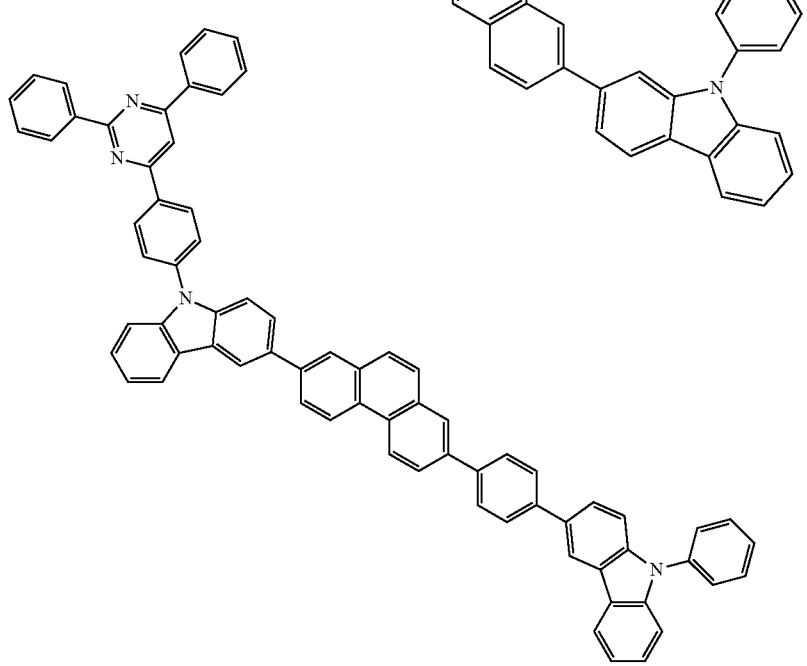
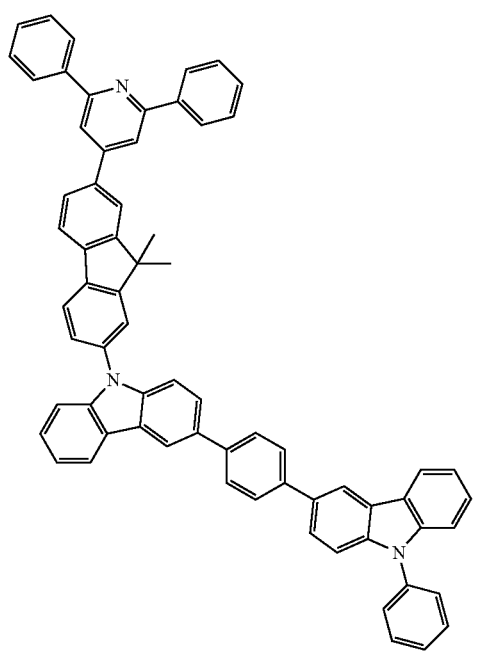
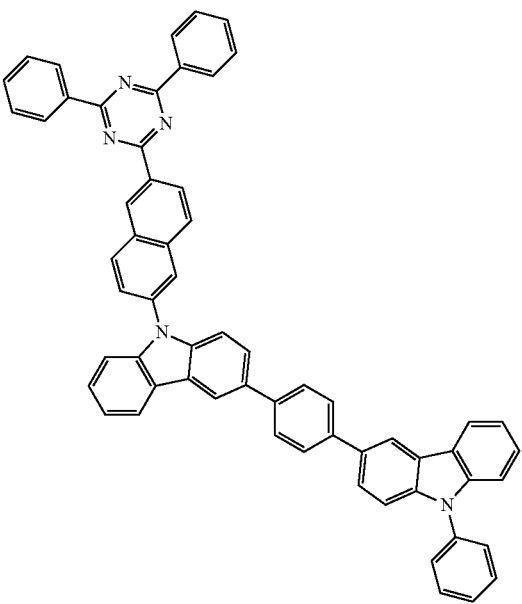

-continued
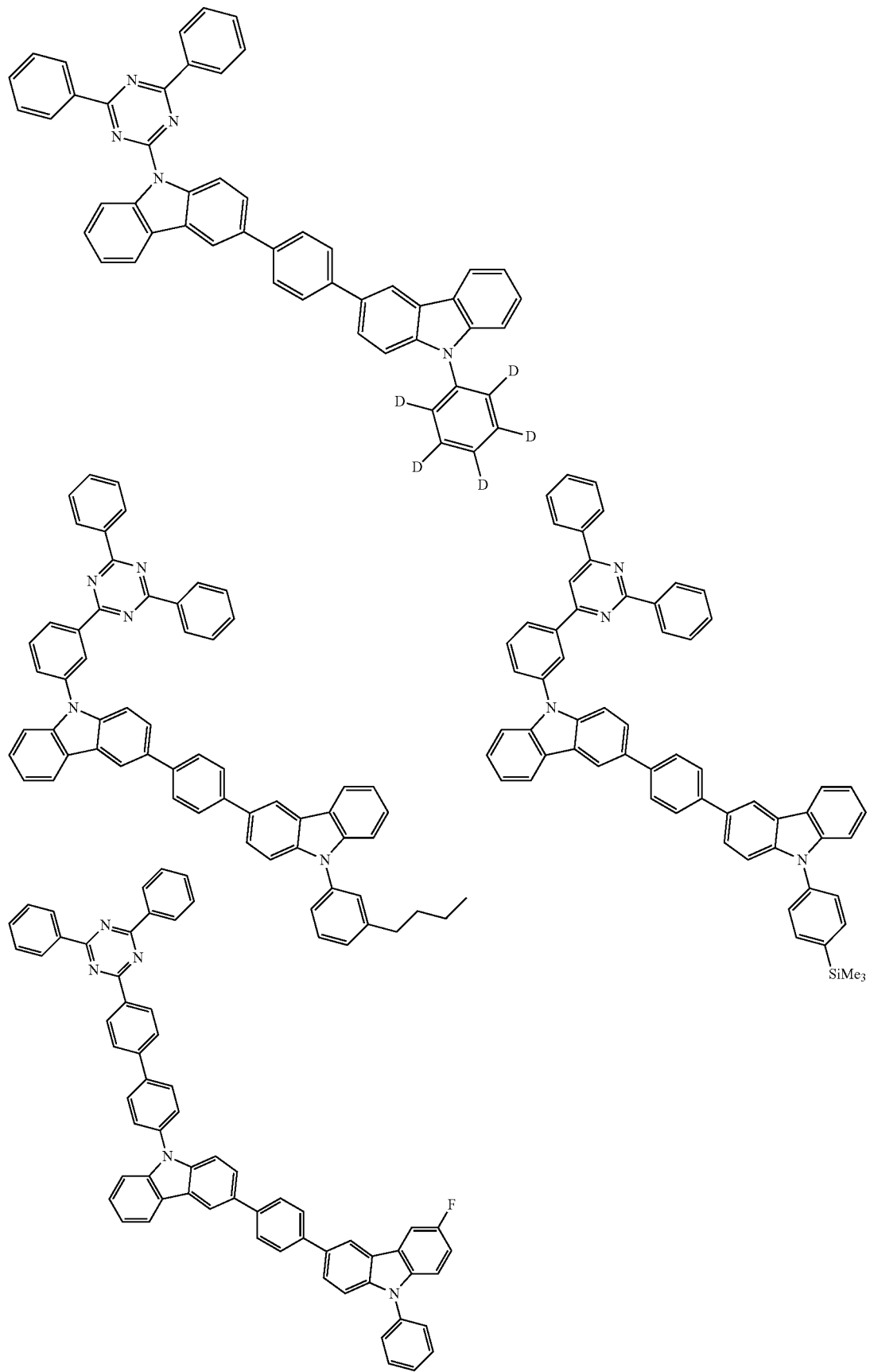

-continued
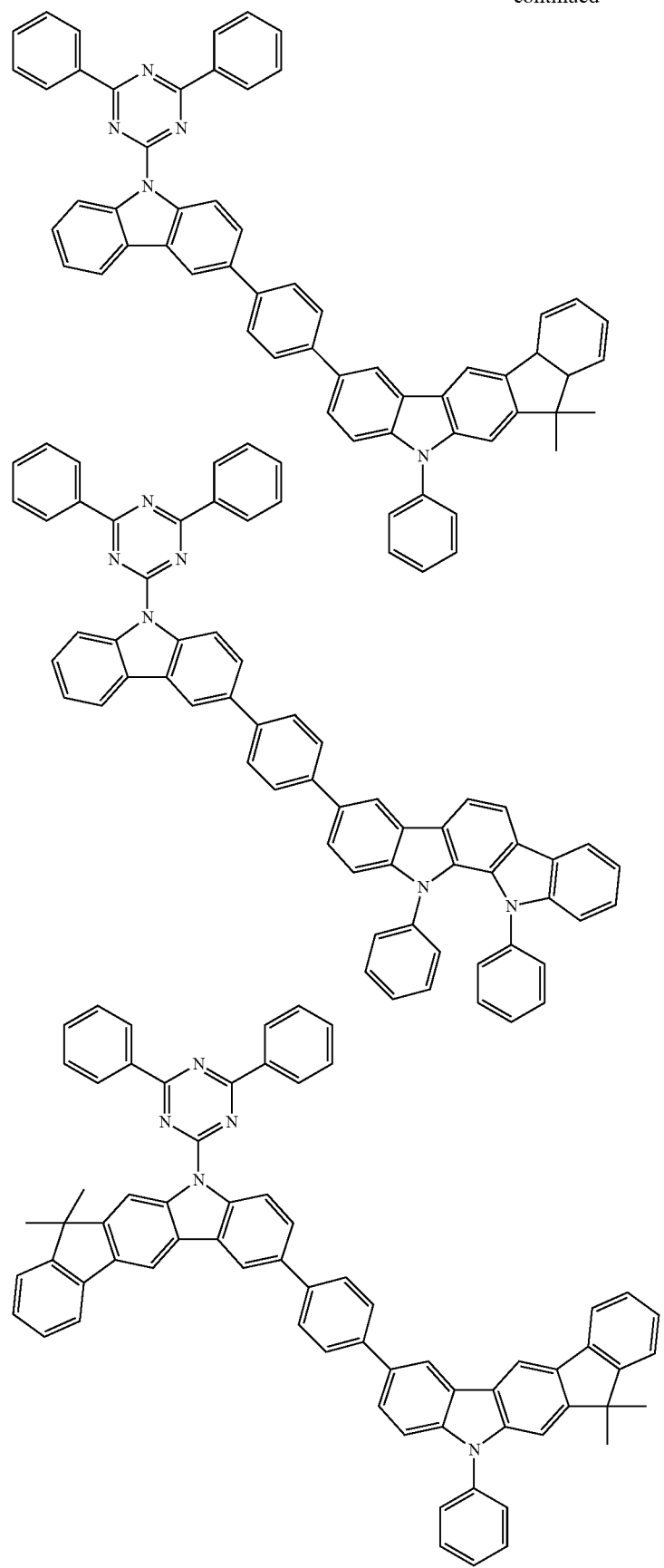

-continued
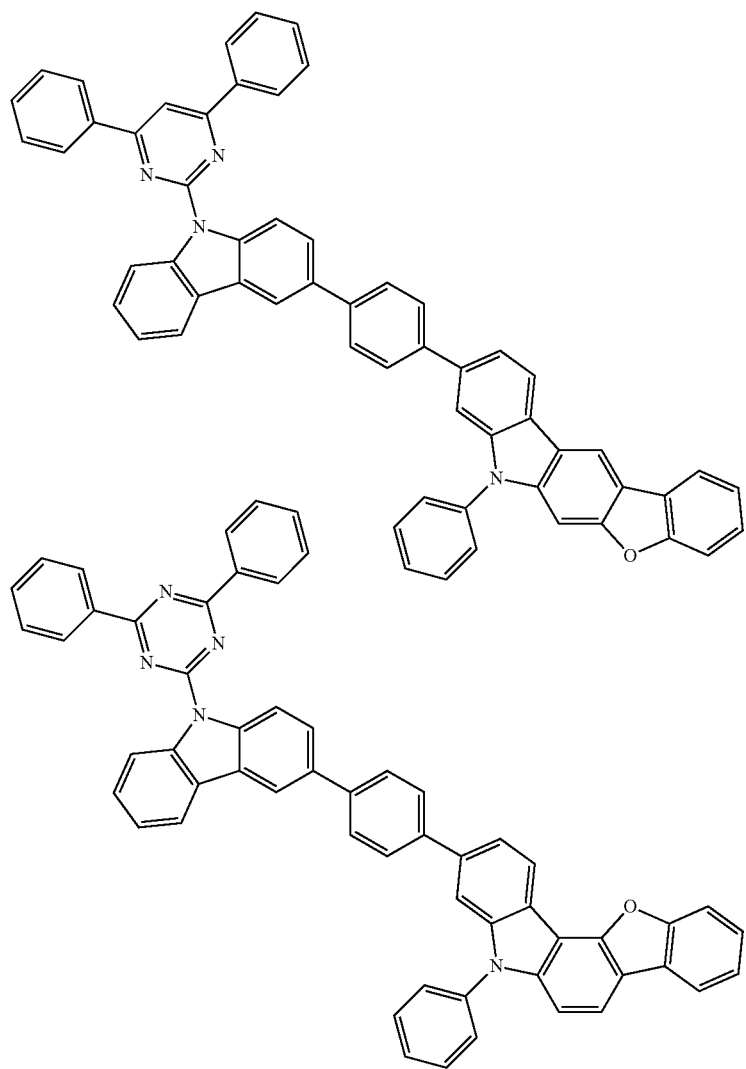
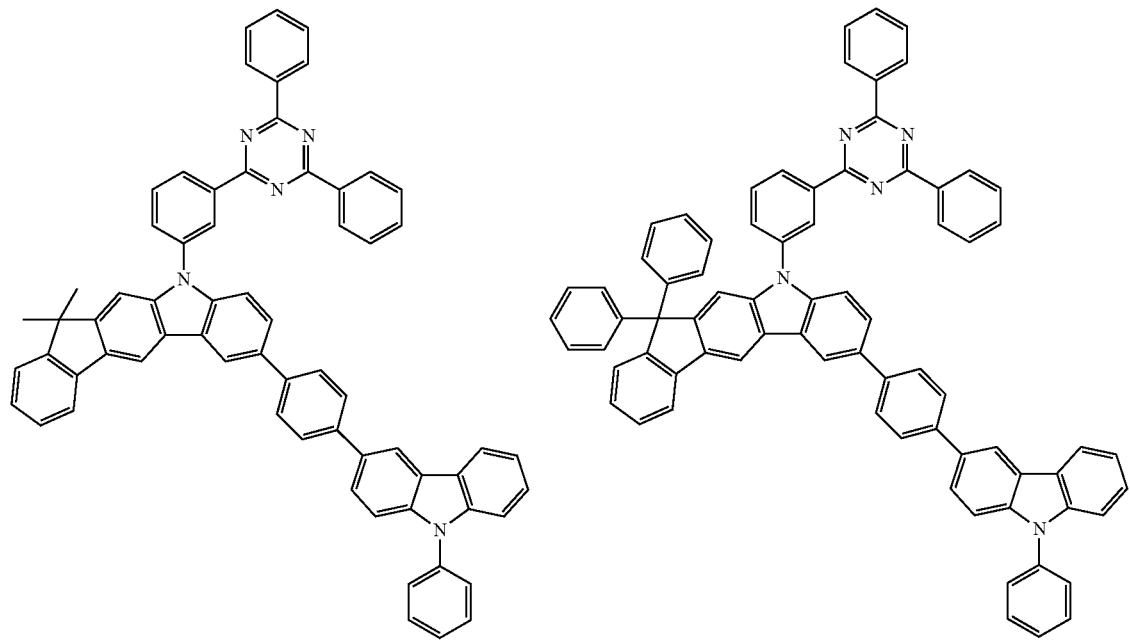

-continued
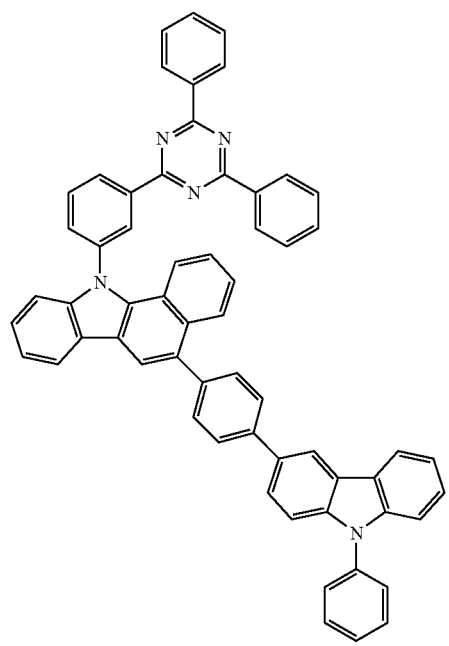
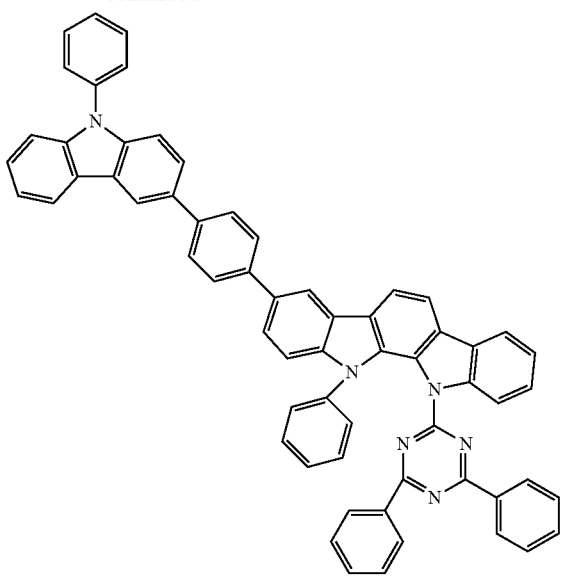
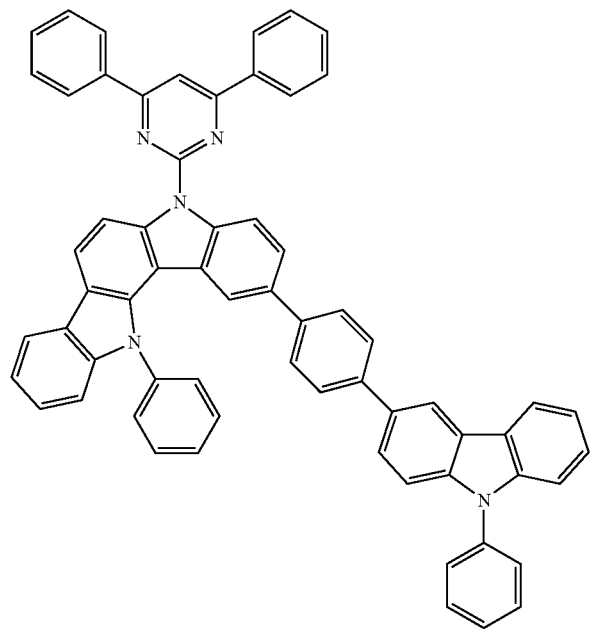

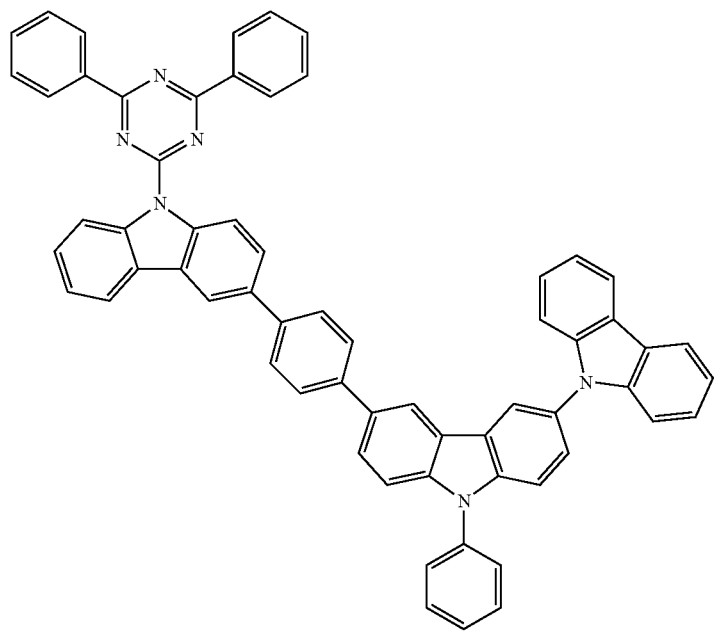
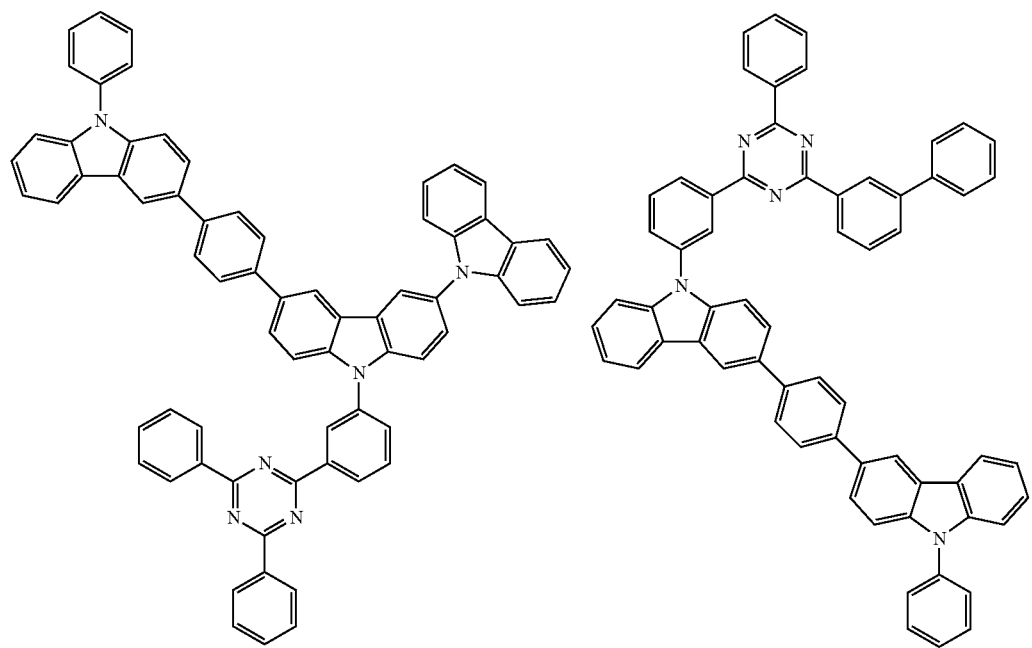

71
-continued
72
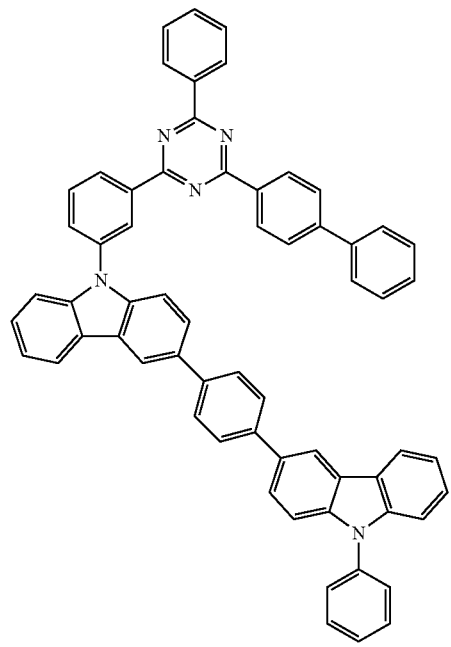
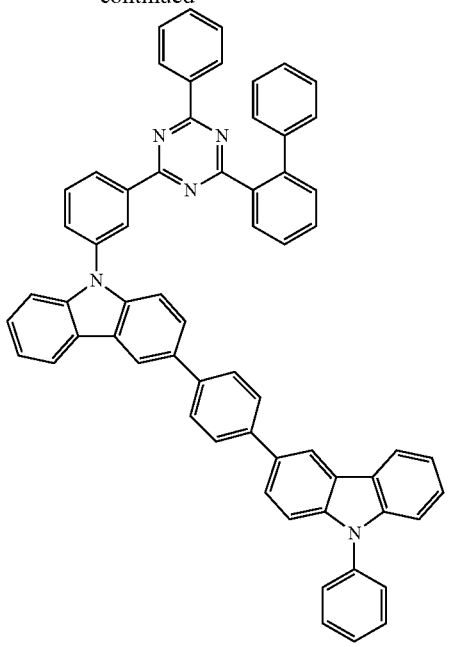
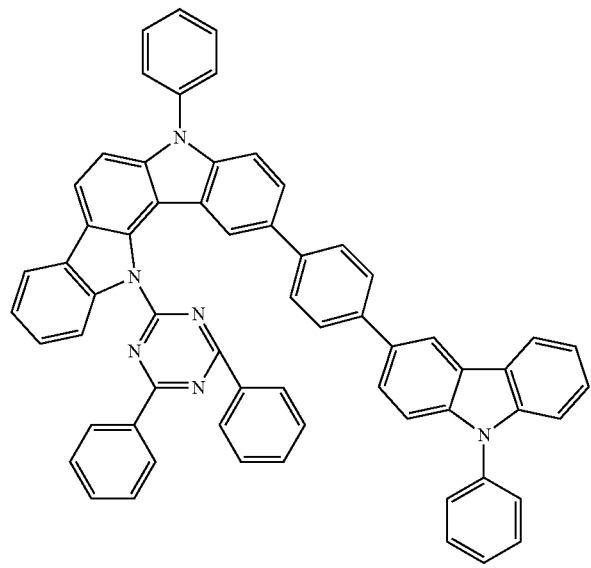
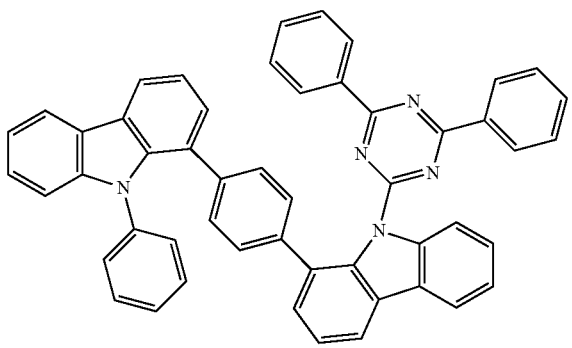
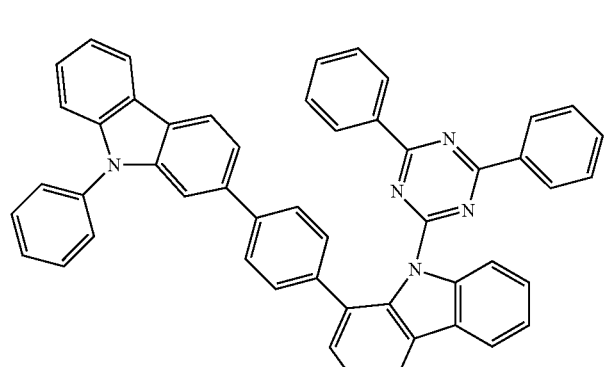
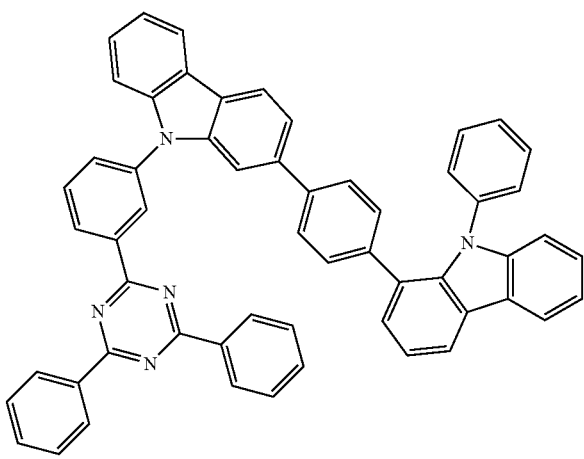

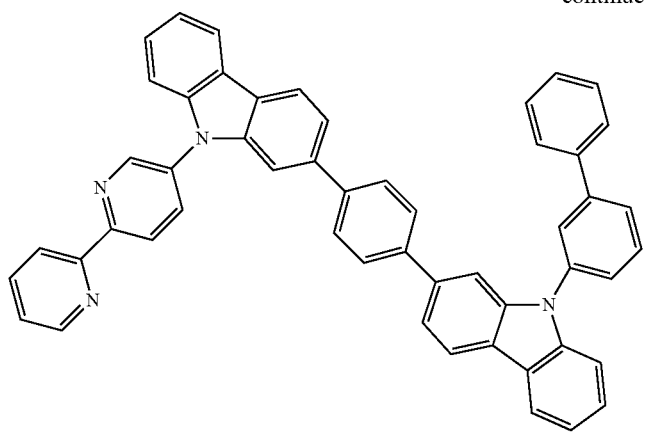
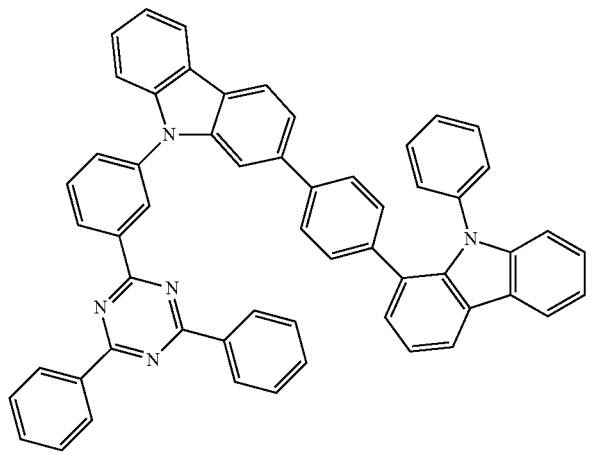
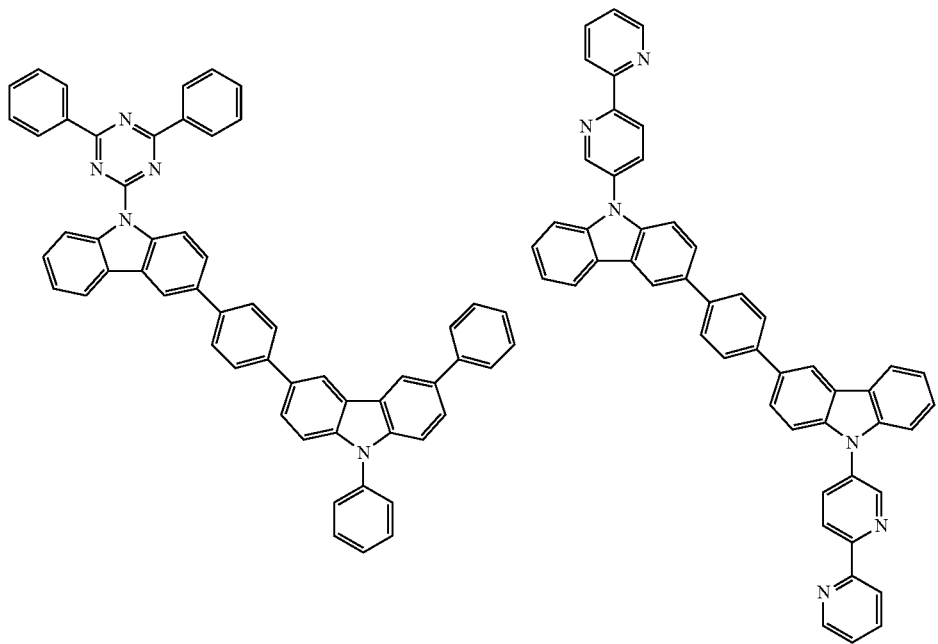

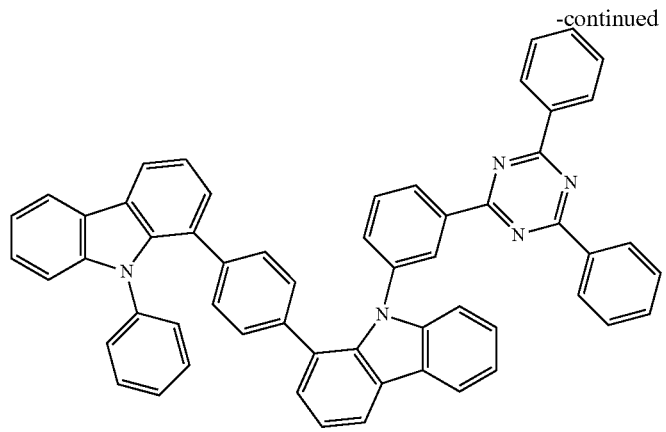

A manufacturing method of the biscarbazole derivative of the compound according to the exemplary embodiment is not particularly limited, but known methods are usable. For instance, a carbazole derivative and a nitrogen-containing six-membered ring compound are subjected to a coupling reaction using a copper catalyst described in "Tetrahedron, 40th volume (1984), p. 1435-1456" or a paradium catalyst described in "Journal of the American Chemical Society, 123 (2001), p. 7727-7729" to manufacture the biscarbazole derivative.

Material for Organic EL Device

The compound according to the exemplary embodiment is usable as a material for an organic EL device.

The material for an organic EL device according to another exemplary embodiment contains the compound according to the above exemplary embodiment. The material for an organic EL device according to the exemplary embodiment may only contain the compound according to the above exemplary embodiment, or alternatively, may contain another compound in addition to the compound according to the above exemplary embodiment. The material for an organic EL device according to the exemplary embodiment is usable for forming the organic thin-film layer of the organic EL device.

Organic EL Device

An organic EL device according to still another exemplary embodiment includes a cathode, an anode, and an organic thin-film layer disposed between the cathode and the anode. The organic thin-film layer has a single-layered or multi-layered structure.

In the organic EL device according to the exemplary embodiment, at least one layer of the organic thin-film layer is the emitting layer. Accordingly, the organic thin-film layer may be provided by a single emitting layer. Alternatively, the organic thin-film layer may be provided by layers applied in a known organic EL device such as a hole injecting layer, a hole transporting layer, an electron injecting layer, an electron transporting layer, a hole blocking layer, an electron blocking layer. The organic thin-film layer may contain an inorganic compound.

The compound according to the above exemplary embodiment is contained in the organic thin-film layer. When the organic thin-film layer is provided by plural layers, the compound according to the above exemplary embodiment is contained singularly or as a component of a mixture in at least one of the layers. The emitting layer preferably contains the compound according to the above exemplary embodiment. Herein, it is preferable that the emitting layer contains the compound according to the above exemplary embodiment as a host material and further contains a dopant material.

The organic EL device may be formed using the material for an organic EL device containing the compound according to the above exemplary embodiment.

Typical device configurations of an organic EL device include, for instance, the following structures (a) to (e) and the like.

(a) anode/emitting layer/cathode;

(b) anode/hole injecting transporting layer/emitting layer/cathode;

(c) anode/emitting layer/electron injecting-transporting layer/cathode;

(d) anode/hole injecting-transporting layer/emitting layer/electron injecting-transporting layer/cathode; and (e) anode/hole injecting-transporting layer/emitting layer/blocking layer/electron injecting-transporting layer/cathode.

While the arrangement (d) is preferably used among the above arrangements, the arrangement of the invention is not limited to the above arrangements.

It should be noted that the aforementioned "emitting layer" is an organic layer having an emission function, the organic layer including a host material and a dopant material when employing a doping system. Herein, the host material mainly has a function to promote recombination of electrons and holes and to confine excitons in the emitting layer while the dopant material has a function to efficiently emit the excitons obtained by the recombination. When the organic EL device is a phosphorescent device, the host material mainly has a function to confine excitons generated in the dopant within the emitting layer.

The "hole injecting/transporting layer means "at least one of a hole injecting layer and a hole transporting layer" while the "electron injecting/transporting layer" means "at least one of an electron injecting layer and an electron transporting layer." Herein, when the hole injecting layer and the hole transporting layer are provided, the hole injecting layer is preferably close to the anode. When the electron injecting layer and the electron transporting layer are provided, the electron injecting layer is preferably close to the cathode.

In the invention, the electron transporting layer means an organic layer having the highest electron mobility among organic layer(s) providing an electron transporting zone existing between the emitting layer and the cathode. When the electron transporting zone is provided by a single layer, the single layer is the electron transporting layer. Moreover, in the phosphorescent organic EL device, a blocking layer having an electron mobility that is not always high may be provided as shown in the arrangement (e) between the emitting layer and the electron transporting layer in order to prevent diffusion of exciton energy generated in the emitting layer. Thus, the organic layer adjacent to the emitting layer does not always correspond to the electron transporting layer.

FIG. 1 schematically shows an exemplary arrangement of an organic EL device according to an exemplary embodiment of the invention.

The organic EL device 1 shown in FIG. 1 includes a transparent substrate 2, an anode 3, a cathode 4 and an organic thin-film layer 10 positioned between the anode 3 and the cathode 4.

The organic thin-film layer 10 sequentially includes a hole injecting layer 5, a hole transporting layer 6, an emitting layer 7, an electron transporting layer 8 and an electron injection layer 9 on the anode 3.

Substrate

The organic EL device in the exemplary embodiment is prepared on a light-transmissive substrate. The light-transmissive plate, which supports the organic EL device, is preferably a flat and smooth substrate that transmits 50% or more of light in a visible region of 400 nm to 700 nm.

Specifically, the light-transmissive substrate is provided by a glass plate, a polymer plate and the like.

For the glass plate, materials such as soda-lime glass, barium/strontium-containing glass, lead glass, aluminosilicate glass, borosilicate glass, barium borosilicate glass and quartz can be used.

For the polymer plate, materials such as polycarbonate, acryl, polyethylene terephthalate, polyether sulfide and polysulfone can be used.

Anode and Cathode

The anode of the organic EL device is used for injecting holes into the hole injecting layer, the hole transporting layer or the emitting layer. It is effective that the anode has a work function of 4.5 eV or more.

Exemplary materials for the anode are alloys of indium-tin oxide (ITO), tin oxide (NESA), indium zinc oxide, gold, silver, platinum and copper.

The anode may be made by forming a thin film from these electrode materials through a method such as vapor deposition or sputtering.

When light from the emitting layer is to be emitted through the anode as in this embodiment, the anode preferably transmits more than 10% of the light in the visible region. Sheet resistance of the anode is preferably several hundreds Ω/square or lower. Although depending on the material of the anode, thickness of the anode is typically in a range of 10 nm to 1 μm, and preferably in a range of 10 nm to 200 nm.

The cathode is preferably formed of a material with smaller work function in order to inject electrons into the electron injecting layer, the electron transporting layer and the emitting layer.

Although a material for the cathode is subject to no specific limitation, examples of the material are indium, aluminum, magnesium, alloy of magnesium and indium, alloy of magnesium and aluminum, alloy of aluminum and lithium, alloy of aluminum, scandium and lithium, alloy of magnesium and silver and the like.

Like the anode, the cathode may be made by forming a thin film from the above materials through a method such as vapor deposition or sputtering. In addition, the light may be emitted through the cathode.

Emitting Layer

The emitting layer of the organic EL device has a function for providing conditions for recombination of the electrons and the holes to emit light.

The emitting layer is preferably a molecular deposit film.

The molecular deposit film means a thin film formed by depositing a material compound in gas phase or a film formed by solidifying a material compound in a solution state or in liquid phase. The molecular deposit film is typically distinguished from a thin film formed by the LB (Langmuir Blodgett) method (i.e., molecular accumulation film) by differences in aggregation structures and higher order structures and functional differences arising therefrom.

As disclosed in JP-A-57-51781, the emitting layer can be formed from a thin film formed by spin coating or the like, the thin film being formed from a solution prepared by dissolving a binder (e.g. a resin) and a material compound in a solvent.

Host Material

A host material is preferably the compound according to the above exemplary embodiment or the material for an organic EL device of the above exemplary embodiment containing the compound according to the above exemplary embodiment.

As described above, when the biscarbazole derivative of the compound according to the exemplary embodiment forms films in a laminate in the organic thin-film layer of the organic EL device, overlapping of π electrons between molecules of the biscarbazole derivative is increased to improve the transporting capability of the organic thin-film layer. The compound according to the exemplary embodiment has a substituted or unsubstituted nitrogen-containing aromatic heterocyclic group for at least one of $A_1$ and $A_2$. Accordingly, the organic thin-film layer containing the compound according to the exemplary embodiment exhibits an improved electron injecting capability. Thus, when the emitting layer of the organic EL device contains the compound according to the exemplary embodiment, carrier balance in the emitting layer is improved, whereby a luminous efficiency of the organic EL device is improvable.

Moreover, with the compound according to the exemplary embodiment, since the HOMO in the moiety of $Cz-L_3-Cz$ and the LUMO of the nitrogen-containing aromatic heterocyclic ring are separable, the compound according to the exemplary embodiment is considered to exhibit an excellent resistance to holes and electrons. Consequently, when the organic thin-film layer contains the compound according to the exemplary embodiment, a lifetime of the organic thin-film layer is improvable.

Note that the emitting layer may contain a known host material as the host material in addition to the compound according to the exemplary embodiment or the material for an organic EL device according to the exemplary embodiment.

Dopant Material

The dopant material is selected from a known fluorescent material that emits fluorescence or a known phosphorescent material that emits phosphorescence.

The fluorescent material used as the dopant material (hereinafter, referred to as a fluorescent dopant material) is selected from a fluoranthene derivative, pyrene derivative, arylacetylene derivative, fluorene derivative, boron complex, perylene derivative, oxadiazole derivative, anthracene derivative and chrysene derivative. The fluoranthene derivative, pyrene derivative and boron complex are preferable.

The phosphorescent material is preferable as the dopant material of the organic EL device according to the exemplary embodiment. The phosphorescent material used as the dopant material (hereinafter, referred to as a phosphorescent dopant material) preferably contains a metal complex. The metal complex preferably contains: a metal atom selected from iridium (Ir), platinum (Pt), osmium (Os), gold (Au), rhenium (Re) and ruthenium (Ru); and a ligand. Particularly, an ortho-metalated complex in which the ligand and the metal atom form an ortho-metal bond is preferable. As the phosphorescent dopant material, an ortho-metalated complex containing a metal selected from the group consisting of iridium (Ir), osmium (Os) and platinum (Pt) is preferable since a phosphorescent quantum yield is high and an external quantum efficiency of an emitting device is improvable. In terms of the luminous efficiency, a metal complex including the ligand selected from phenyl quinoline, phenyl isoquinoline, phenyl pyridine, phenyl pyrimidine, phenyl pyrazine and phenyl imidazole is preferable.

A content of the dopant material in the emitting layer is not particularly limited. Although the content thereof can be selected according to the need, for instance, the content thereof is preferably in a range of 0.1 mass % to 70 mass %, more preferably of 1 mass % to 30 mass %. When the content of the dopant material is 0.1 mass % or more, a sufficient emission is obtained. When the content of the dopant material is 70 mass % or less, concentration quenching is avoidable.

Examples of the phosphorescent dopant material are shown below.

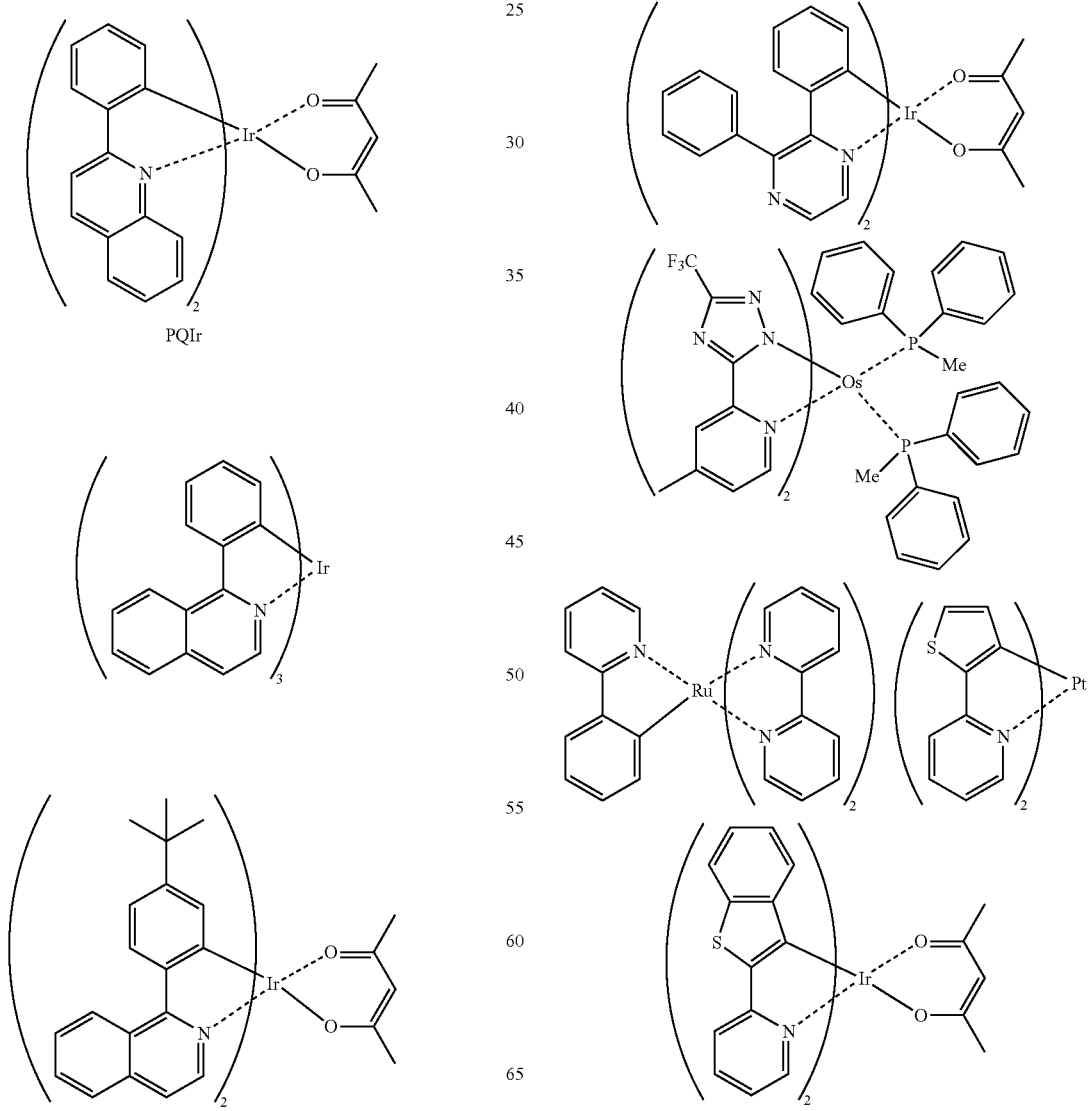

81
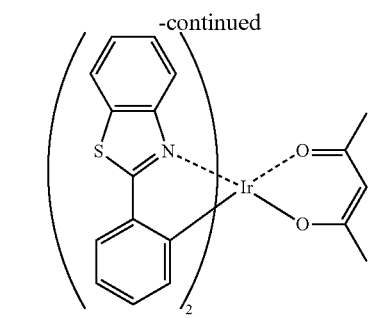
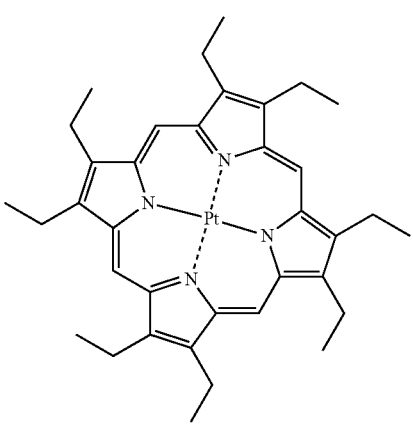
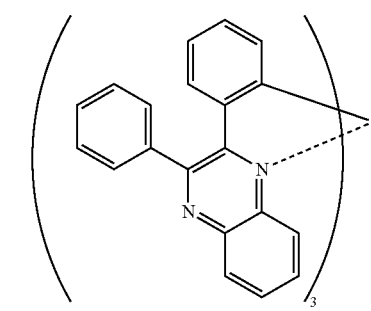
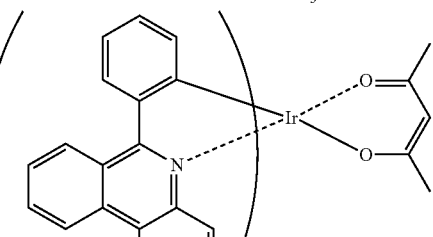
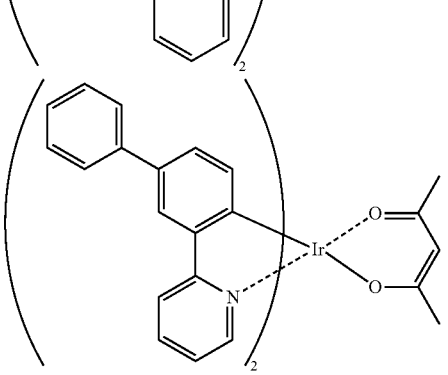
82
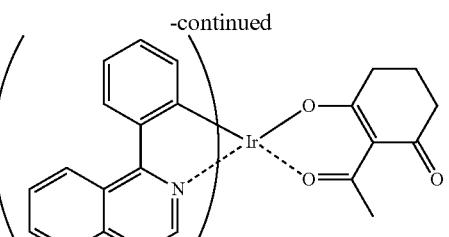
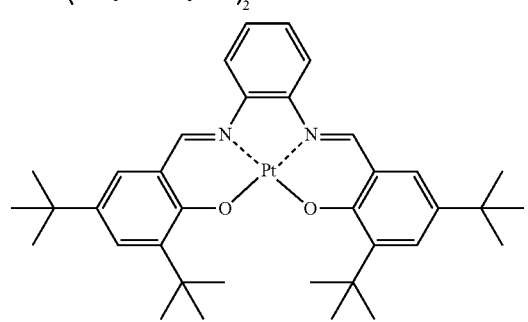
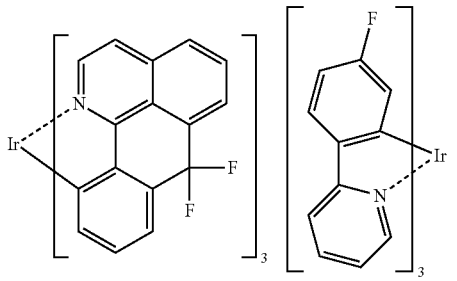
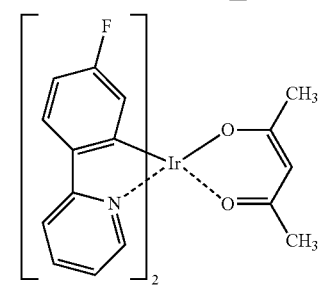
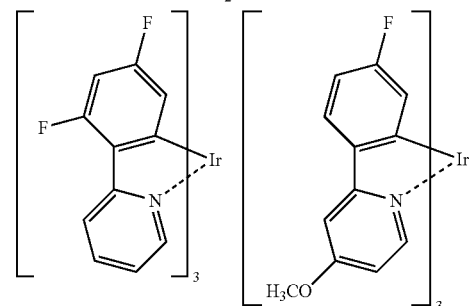
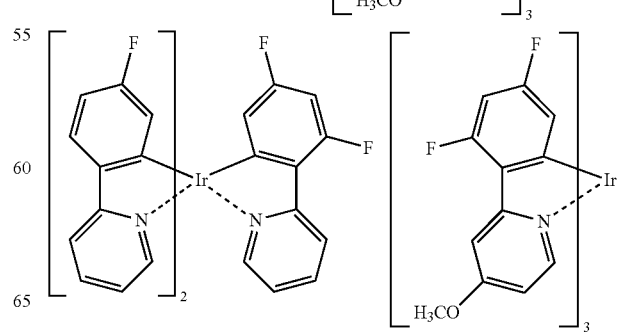

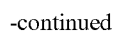
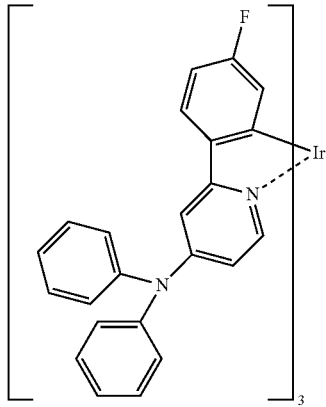
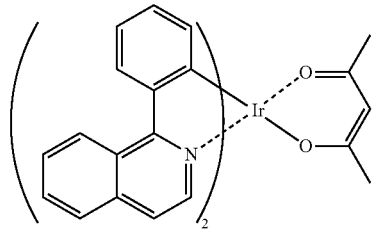
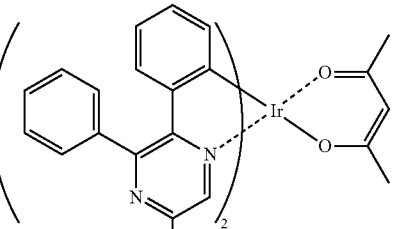
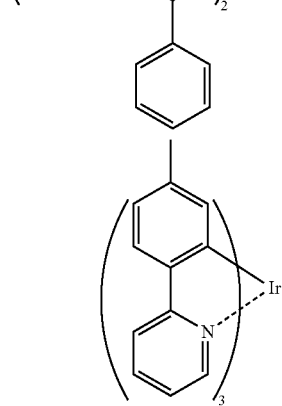
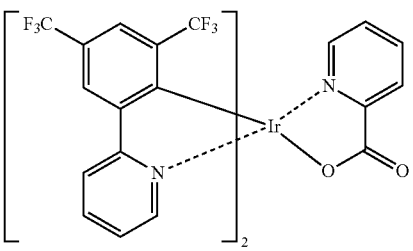
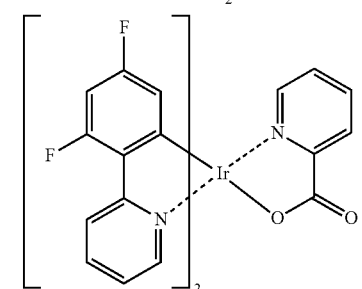
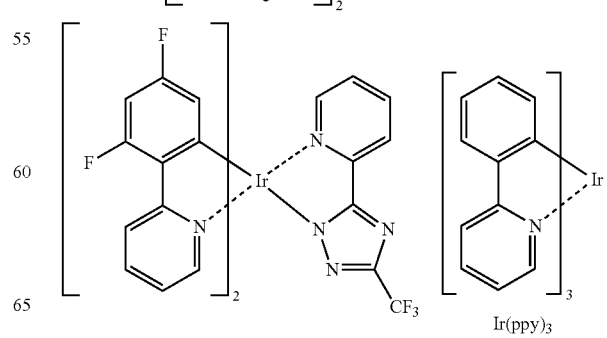

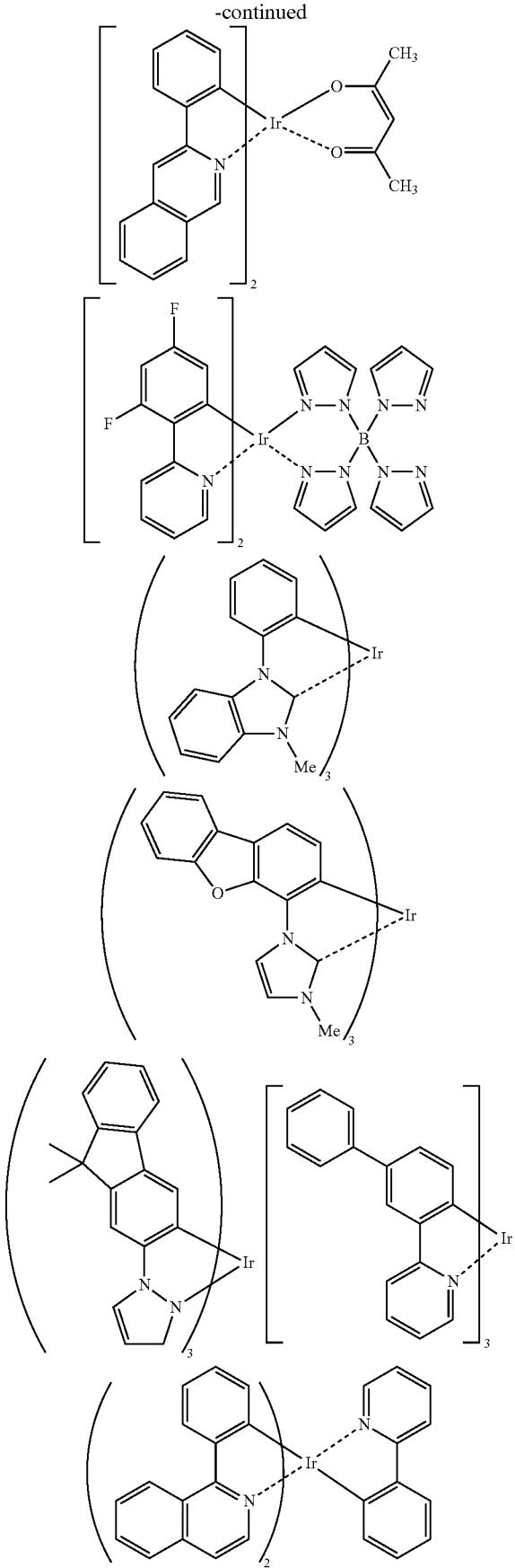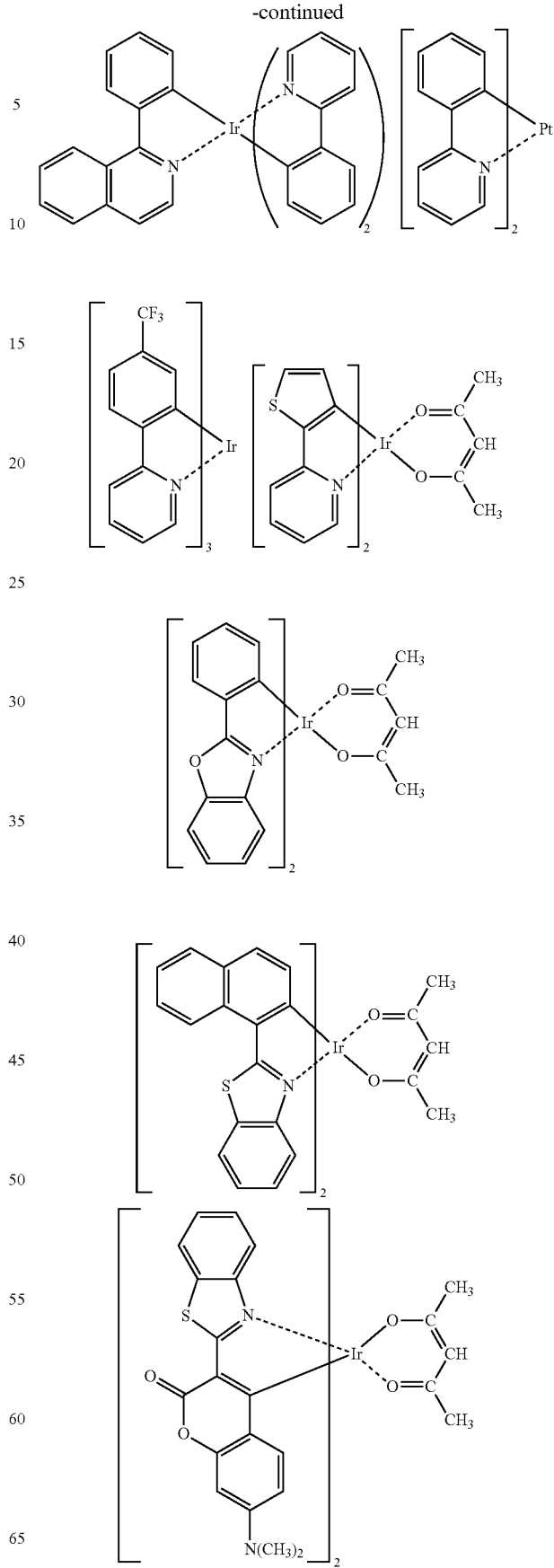

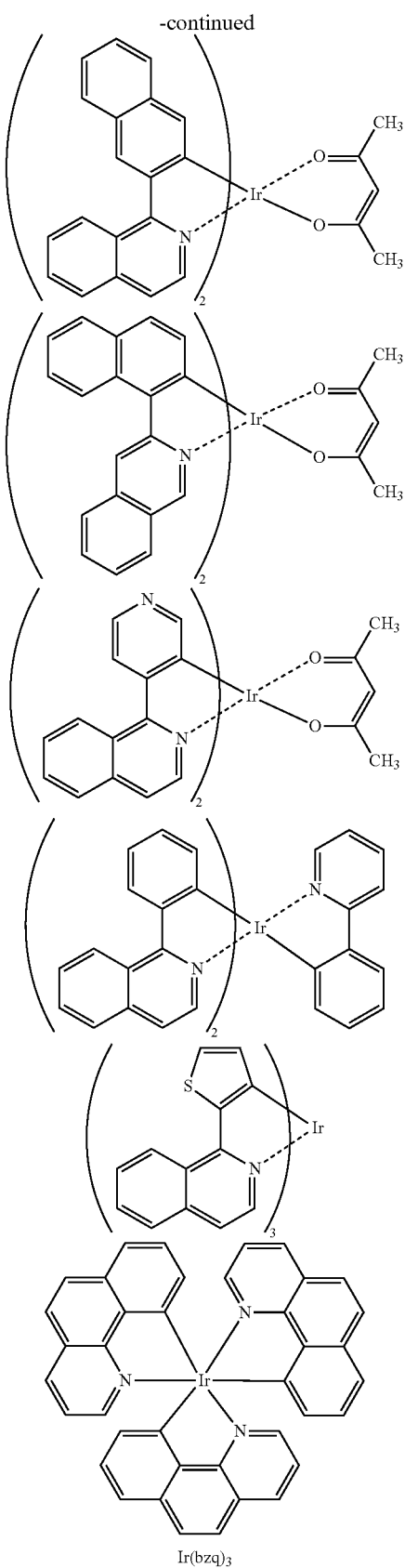

As described above, the biscarbazole derivative of the compound according to the exemplary embodiment has triplet energy suitable for a phosphorescent host material. Accordingly, the biscarbazole derivative of the compound according to the exemplary embodiment is suitable for the phosphorescent host material, which is particularly suitable for a phosphorescent dopant material exhibiting red, yellow and green emissions.

One of the phosphorescent dopant material may be singularly used, or two or more kinds thereof may be used in combination.

An emission wavelength of the phosphorescent dopant material contained in the emitting layer is not particularly limited, but at least one of the phosphorescent dopant material contained in the emitting layer preferably has a peak of the emission wavelength in a range of 490 nm to 700 nm, more preferably in a range of 490 nm to 650 nm. Preferable emission colors of the emitting layer are, for instance, red, yellow and green. Using the compound according to the exemplary embodiment as the host material and doping the phosphorescent dopant material having such an emission wavelength, the organic EL device can exhibit a high efficiency and a long lifetime.

Hole Injecting Layer and Hole Transporting Layer

The hole injecting layer and the hole transporting layer help injection of holes to the emitting layer and transport the holes to an emitting region. A compound having a large hole mobility and a small ionization energy is used as the hole injecting layer and the hole transporting layer.

A material for forming the hole injecting layer and the hole transporting layer is preferably a material for transporting the holes to the emitting layer at a lower electric field intensity. For instance, an aromatic amine compound is preferably used. A material for the hole injecting layer is preferably a porphyrin compound, an aromatic tertiary amine compound or a styryl amine compound, particularly preferably the aromatic tertiary amine compound such as hexacyanohexaazatriphenylene (HAT).

Electron Injecting Layer and Electron Transporting Layer

The electron injecting layer and the electron transporting layer help injection of the electrons into the emitting layer and transport the electrons to an emitting region. A compound having a large electron mobility is used as the electron injecting layer and the electron transporting layer.

A compound used as the electron injecting layer and the electron transporting layer is preferably an aromatic heterocyclic compound having at least one heteroatom in a molecule, particularly preferably a nitrogen-containing cyclic derivative. The nitrogen-containing cyclic derivative is preferably a heterocyclic compound having a nitrogen-containing six-membered or five-membered ring skeleton.

In the organic EL device according to the exemplary embodiment, in addition to the above exemplary compound, any compound selected from compounds known as being used in the typical organic El device is usable as a compound for the organic thin-film layer other than the emitting layer (i.e., the hole injecting layer, hole transporting layer, electron transporting layer, electron injecting layer and blocking layer).

Hole Injecting/Transporting Layer

The hole injecting/transporting layer helps injection of holes to the emitting layer and transports the holes to an emitting region. The hole injecting/transporting layer exhibits a large hole mobility and a small ionization energy.

The hole injecting/transporting layer may be provided by a hole injecting layer or a hole transporting layer, or alternatively, may be provided by a laminate of a hole injecting layer and a hole transporting layer.

A material for forming the hole injection/transport layer is preferably a material for transporting the holes to the emitting layer at a lower electric field intensity. For instance, an aromatic amine compound represented by the following formula (A1) is preferably used.

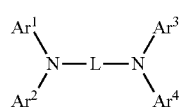

In the formula (A1), $Ar^1$ to $Ar^4$ each independently represent an aromatic hydrocarbon group having 6 to 50 ring carbon atoms, aromatic heterocyclic group having 2 to 40 ring carbon atoms, or a group formed by combining the aromatic hydrocarbon group with the aromatic heterocyclic group, or a group formed by combining the aromatic hydrocarbon group with the aromatic heterocyclic group. Note that the aromatic hydrocarbon group and the aromatic heterocyclic group described herein may have a substituent.

In the formula (A1), L is a linking group and represents a divalent aromatic hydrocarbon group having 6 to 50 ring carbon atoms, a divalent aromatic heterocyclic group having 5 to 50 ring carbon atoms, and a divalent group formed by two or more aromatic hydrocarbon groups or aromatic heterocyclic groups which are bonded through a single bond, ether bond, thioether bond, or through an alkylene group having 1 to 20 carbon atoms, an alkenylene group having 2 to 20 carbon atoms or an amino group. Note that the divalent aromatic hydrocarbon group and the divalent aromatic heterocyclic group described herein may have a substituent.

Examples of the compound represented by the formula (A1) are shown below. However, the compound represented by the formula (A1) is not limited thereto.

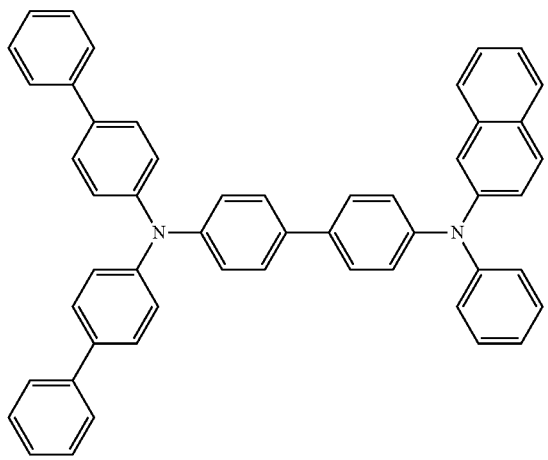

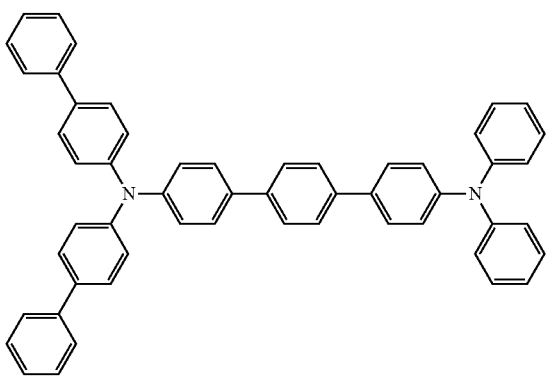

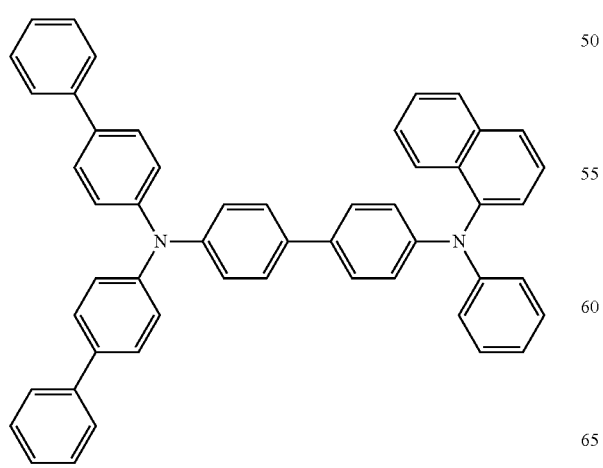

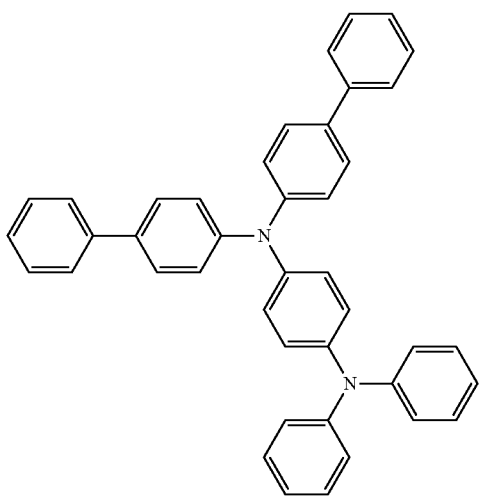

91
-continued
92
-continued
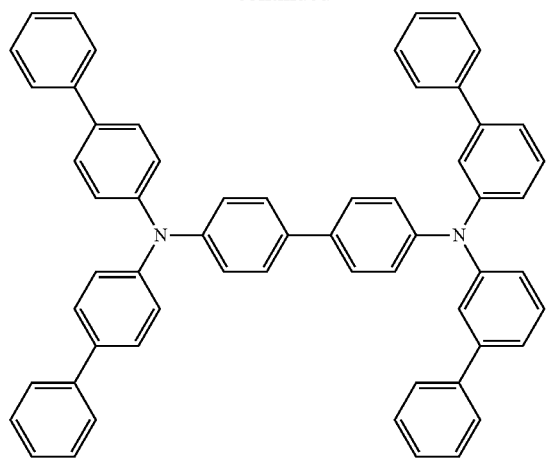
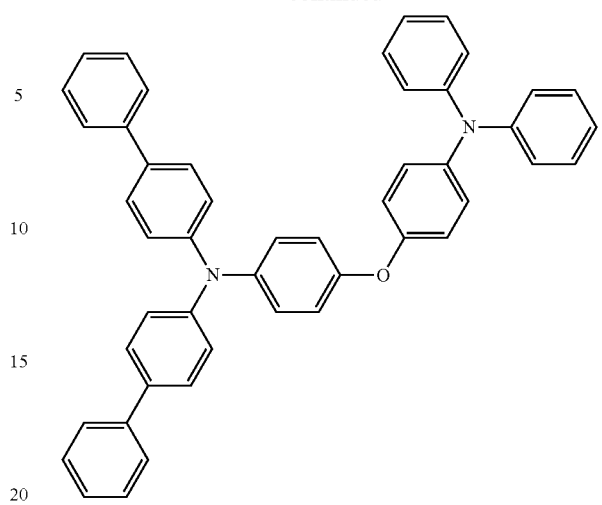
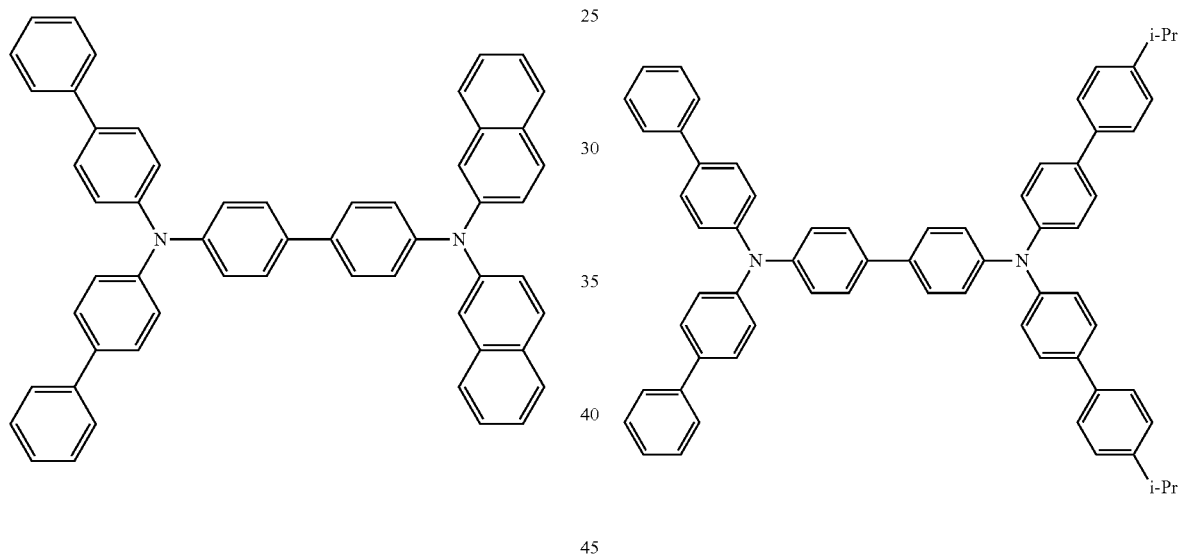
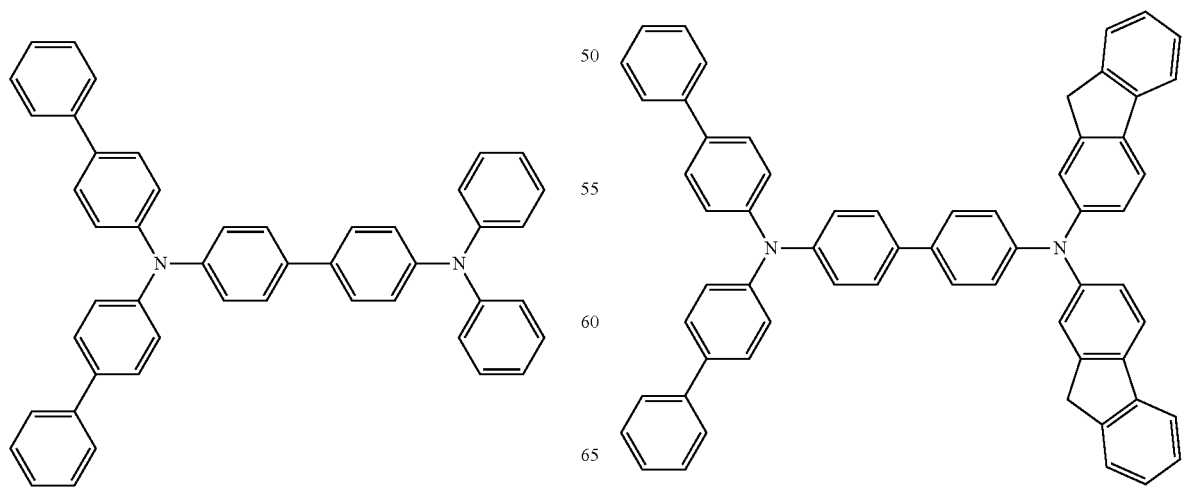

93
-continued
94
-continued
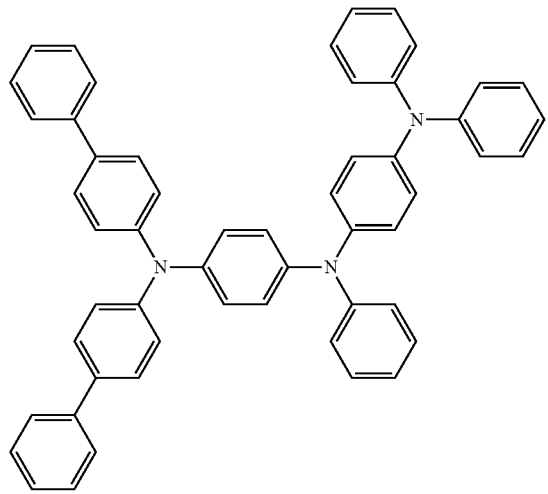
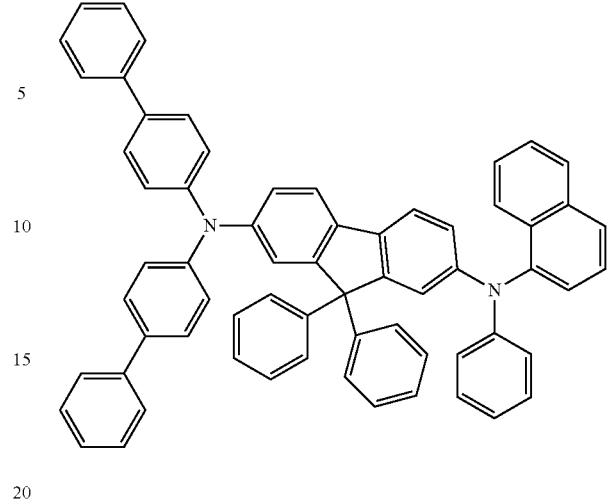
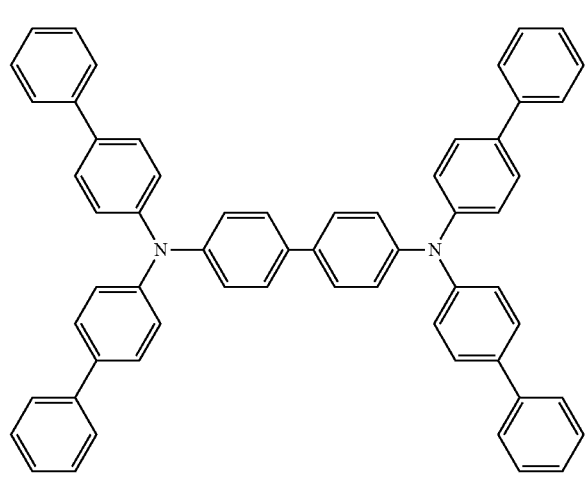
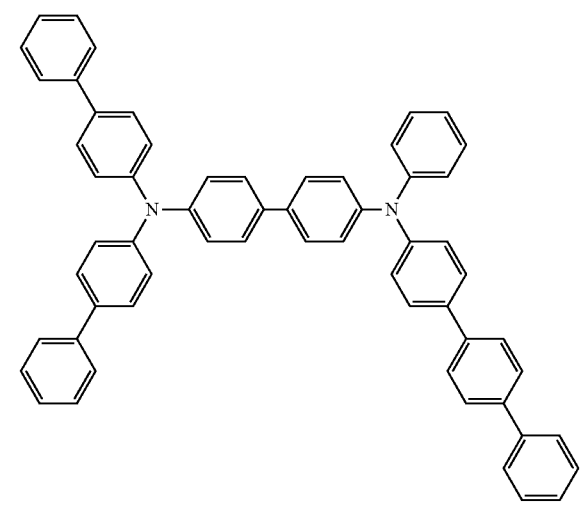
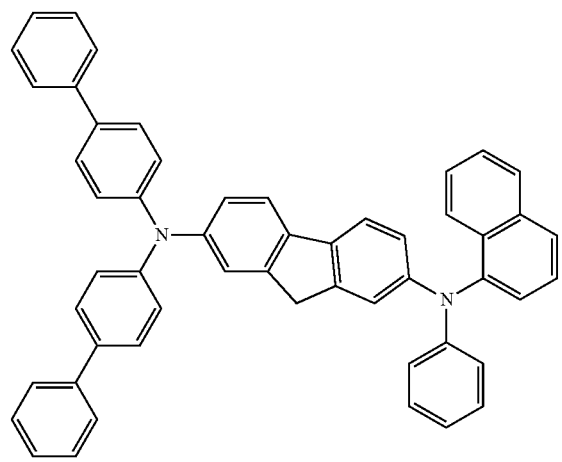
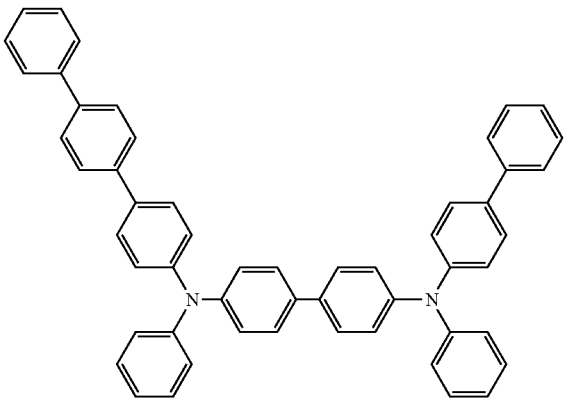

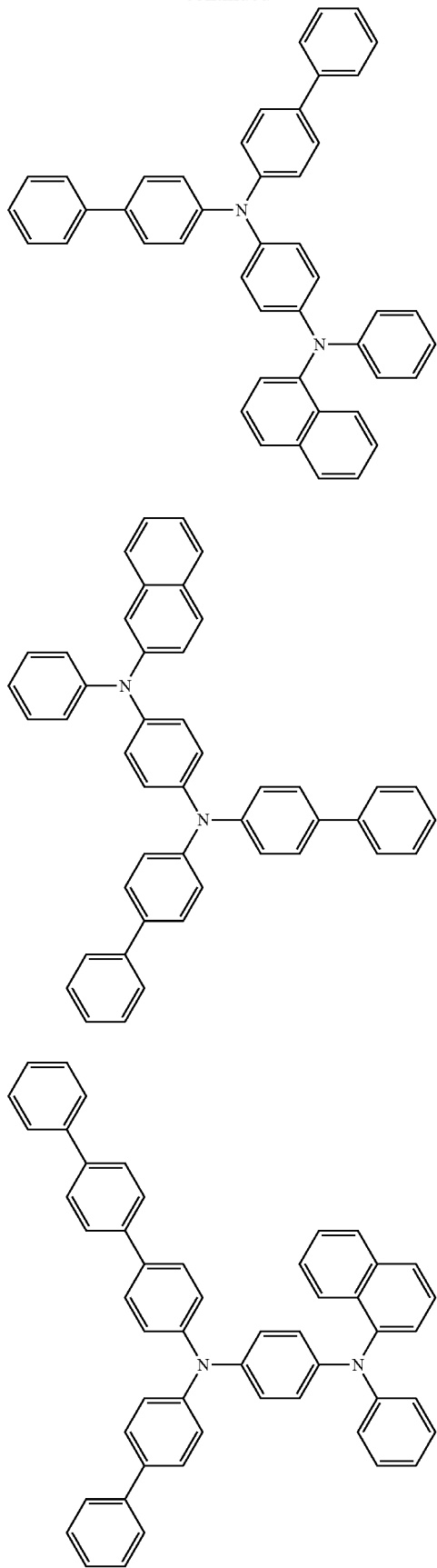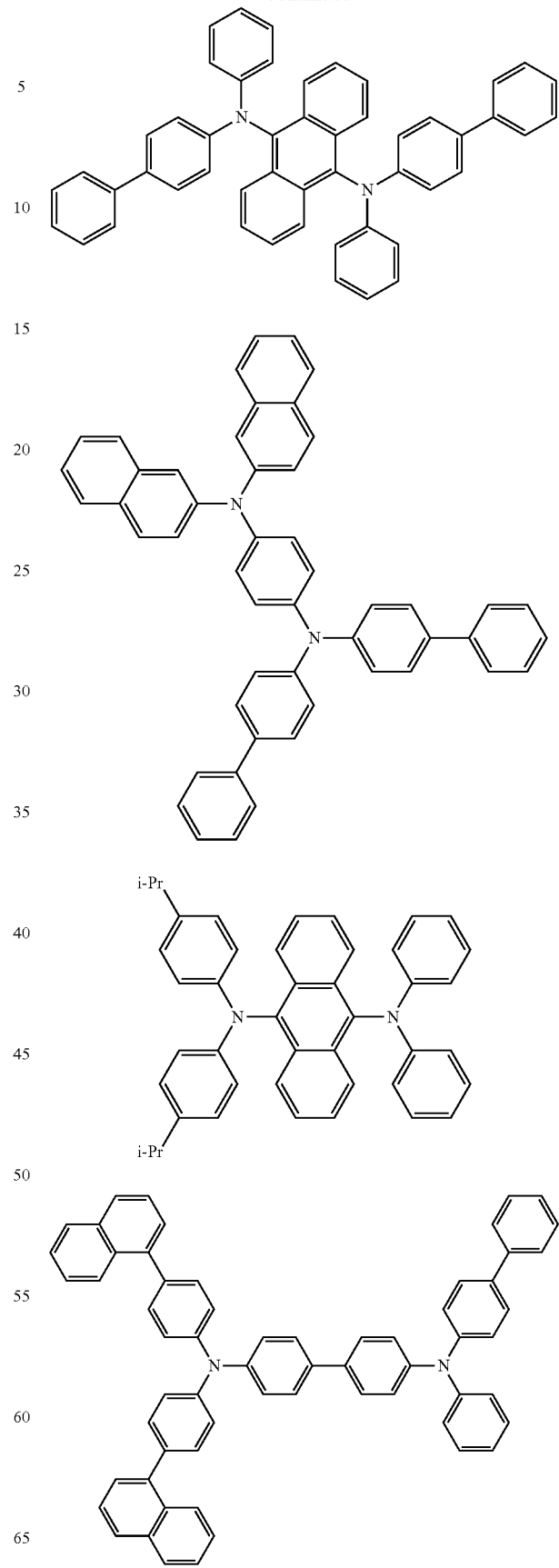

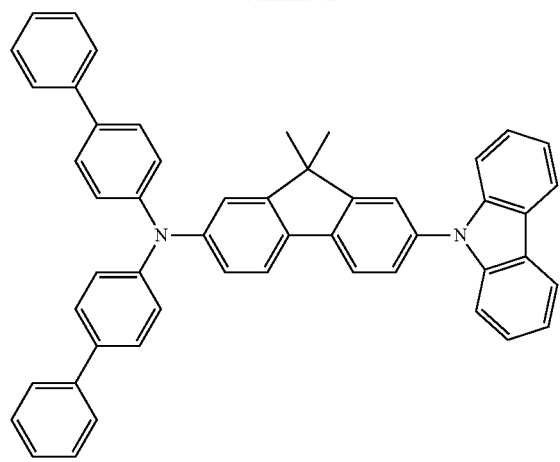
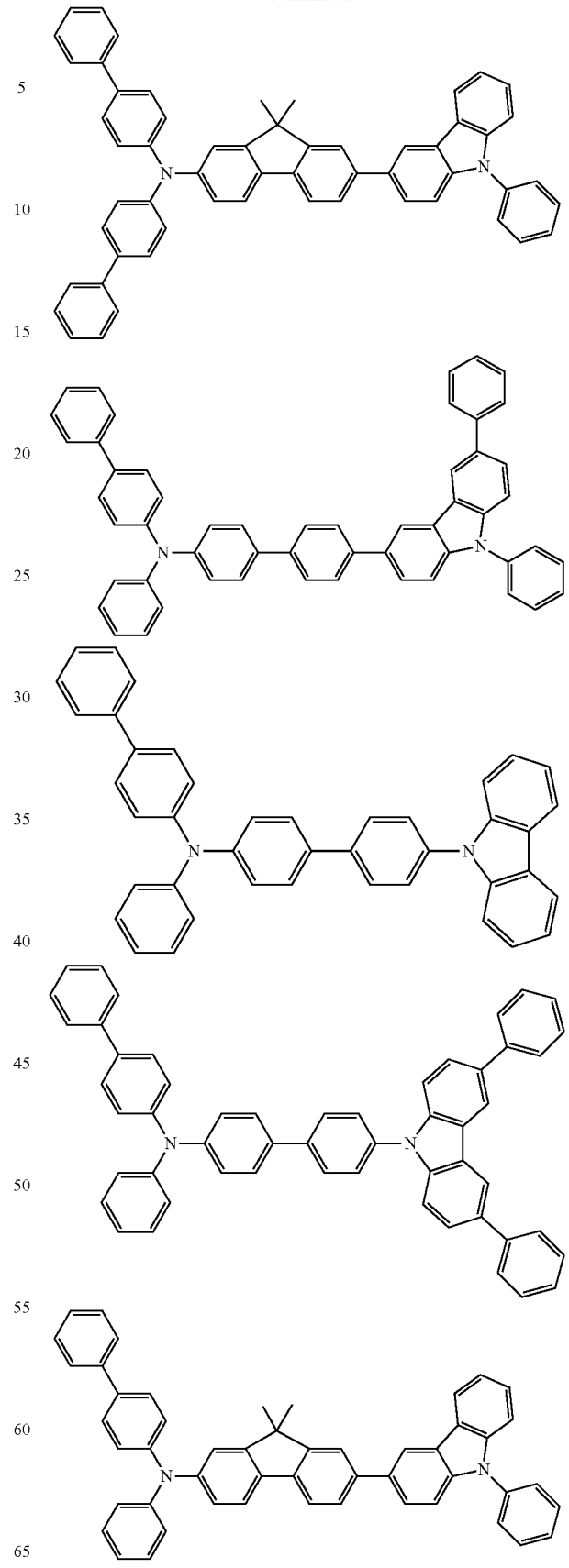

Aromatic amine represented by the following formula (A2) can also be preferably used for forming the hole injecting/transporting layer.

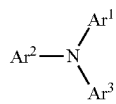
(A2)

In the above formula (A2), $Ar^1$ to $Ar^3$ each represent the same as $Ar^1$ to $Ar^4$ of the above formula (A1). Examples of the compound represented by the formula (A2) are shown below. However, the compound represented by the formula (A2) is not limited thereto.

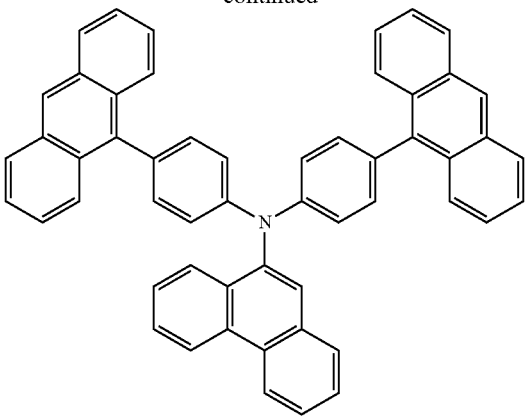

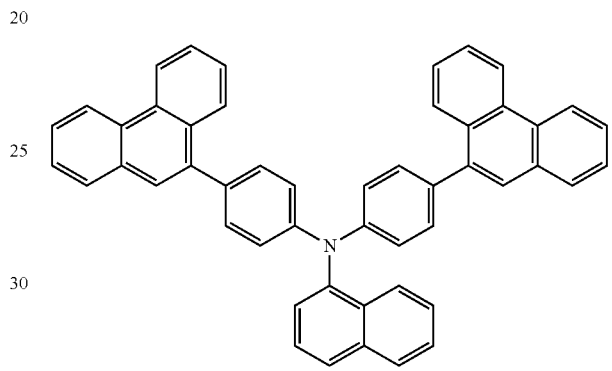

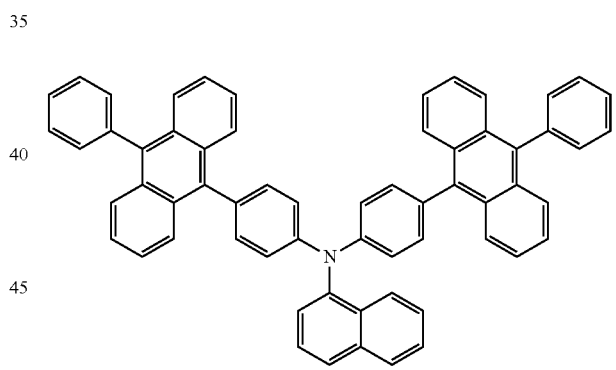

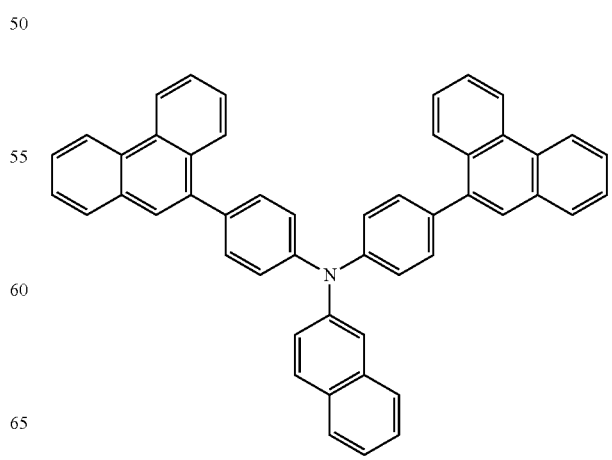

101
-continued
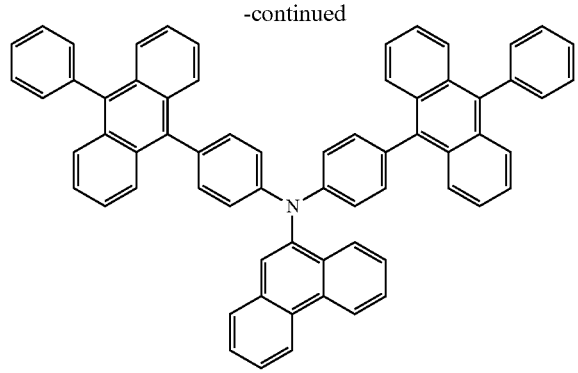
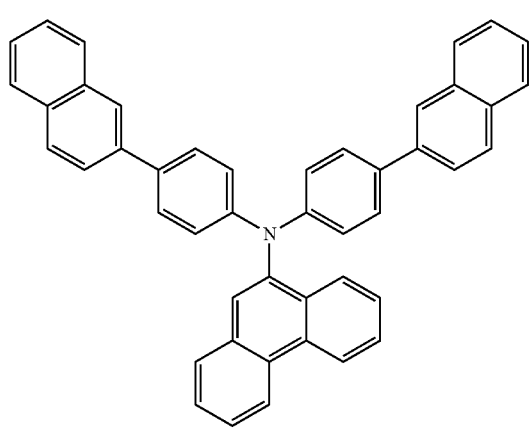
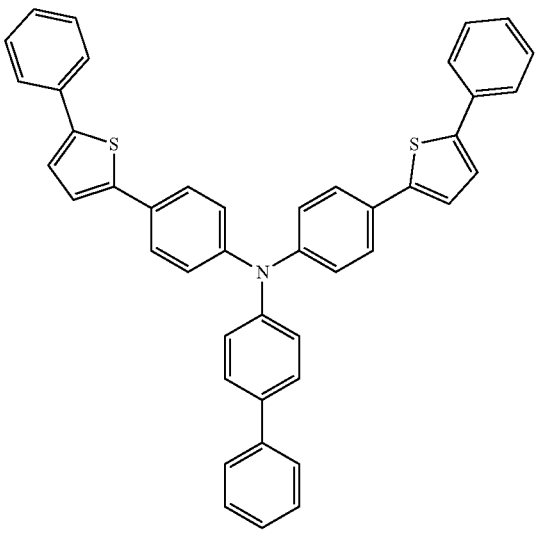
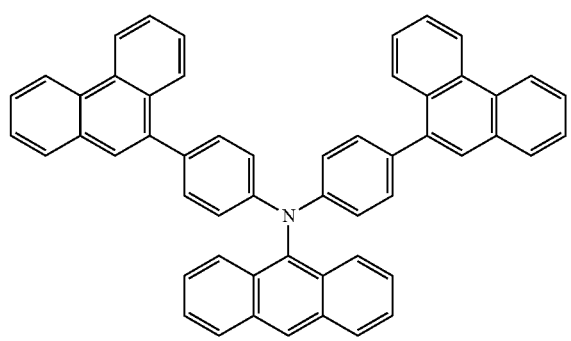
102
-continued
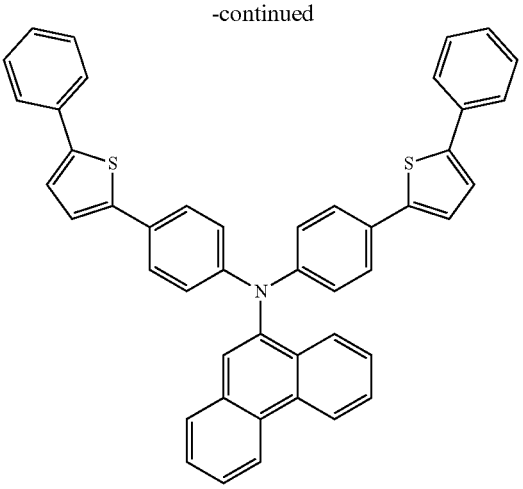
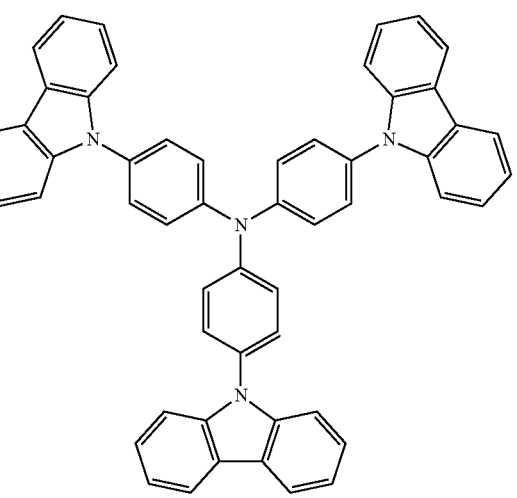
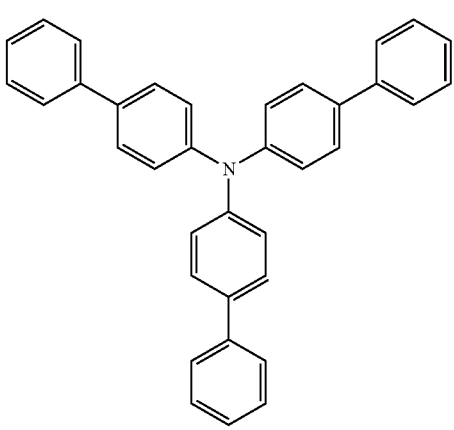

-continued

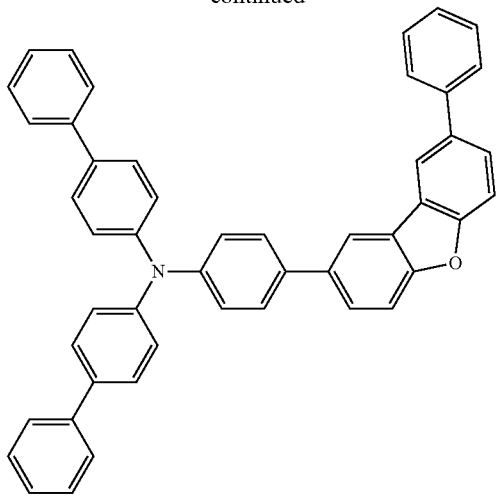

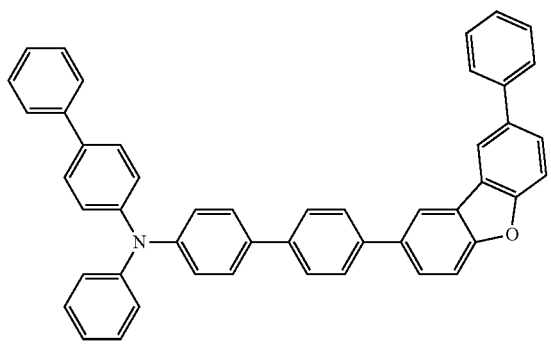

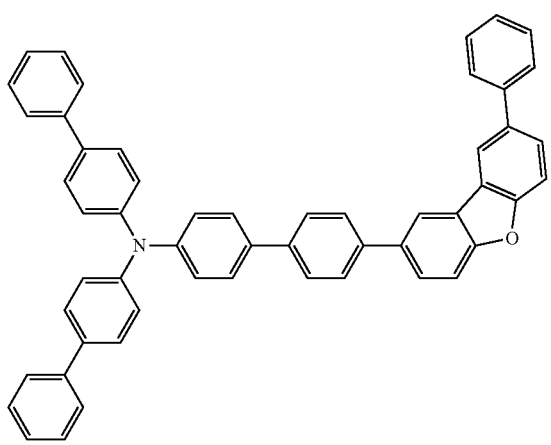

Electron Injecting/Transporting Layer

The electron injection/transport layer helps injection of the electron to the luminescent layer and has a high electron mobility. The electron injecting layer is provided for adjusting energy level, by which, for instance, sudden changes of the energy level can be reduced. The electron injection/transport layer includes at least one of the electron injecting layer and the electron transporting layer.

The organic EL device according to this exemplary embodiment preferably includes the electron injecting layer between the emitting layer and the cathode, and the electron injecting layer preferably contains a nitrogen-containing cyclic derivative as a main component. The electron injecting layer may serve as the electron transporting layer.

Noted that "as a main component" means that the nitrogen-containing cyclic derivative is contained in the electron injecting layer at a content of 50 mass % or more.

The electron transporting material for forming the electron injecting layer is preferably exemplified by an aromatic heterocyclic compound having in the molecule at least one heteroatom (e.g., nitrogen, oxygen, sulfur and phosphorus). Particularly, a nitrogen-containing cyclic derivative is preferable. The nitrogen-containing cyclic derivative is preferably an aromatic cyclic compound having a nitrogen-containing six-membered or five-membered ring skeleton.

The nitrogen-containing cyclic derivative is preferably exemplified by a nitrogen-containing cyclic metal chelate complex represented by the following formula (B1).

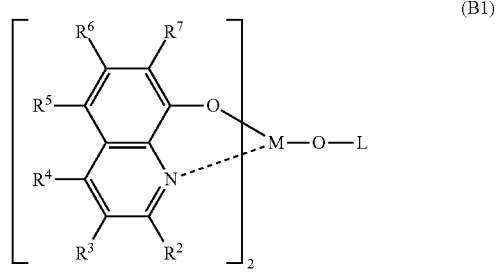

(B1)

$R^2$ to $R^7$ in the formula (B1) each independently represent a hydrogen atom, halogen atom, oxy group, amino group, hydrocarbon group having 1 to 40 carbon atoms, alkoxy group having 1 to 40 carbon atoms, aryloxy group having 1 to 40 carbon atoms, alkoxycarbonyl group having 1 to 40 carbon atoms, or aromatic heterocyclic group having 1 to 40 carbon atoms. These groups may have a substituent.

Examples of the halogen atom are fluorine, chlorine, bromine and iodine. Examples of a substituted or unsubstituted amino group are an alkylamino group, an arylamino group and an aralkylamino group.

The alkoxycarbonyl group is represented by —COOY'. Examples of Y' are the same as the examples of the alkyl group. The alkylamino group and the aralkylamino group are represented by —NQ$^1$Q$^2$. Examples for each of Q$^1$ and Q$^2$ are the same as the examples described in relation to the alkyl group and the aralkyl group (i.e., a group obtained by substituting a hydrogen atom of an alkyl group with an aryl group), and preferable examples for each of Q$^1$ and Q$^2$ are also the same as those described in relation to the alkyl group and the aralkyl group. One of Q$^1$ and Q$^2$ may be a hydrogen atom. Note that the aralkyl group is a group obtained by substituting the hydrogen atom of the alkyl group with the aryl group.

The arylamino group is represented by —NAr$^1$Ar$^2$. Examples for each of Ar$^1$ and Ar$^2$ are the same as the examples described in relation to the non-fused aromatic hydrocarbon group. One of Ar$^1$ and Ar$^2$ may be a hydrogen atom.

M in the formula (B1) represents aluminum (Al), gallium (Ga) or indium (In), among which In is preferable.

L in the formula (B1) represents a group represented by a formula (B2) or (B3) below.

(B2)

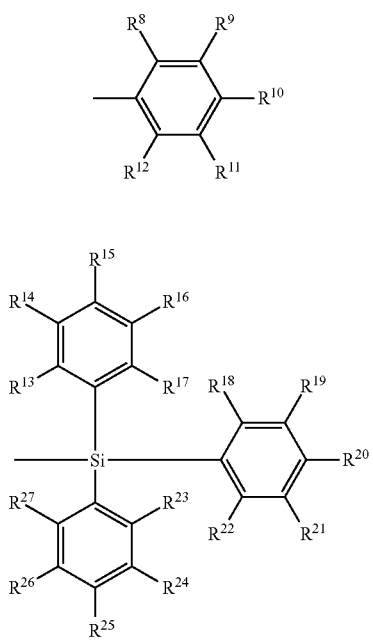

(B3)

(B6)

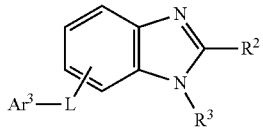

In the formulae (B4) to (B6), R represents a hydrogen atom, aromatic hydrocarbon group having 6 to 60 ring carbon atoms, pyridyl group, quinolyl group, alkyl group having 1 to 20 carbon atoms, or alkoxy group having 1 to 20 carbon atoms.

n is an integer in a range of 0 to 4.

In the formulae (B4) to (B6), $R^1$ represents an aromatic hydrocarbon group having 6 to 60 ring carbon atoms, pyridyl group, quinolyl group, alkyl group having 1 to 20 carbon atoms, or alkoxy group having 1 to 20 carbon atoms.

In the formulae (B4) to (B6), $R^2$ and $R^3$ each independently represent a hydrogen atom, aromatic hydrocarbon group having 6 to 60 ring carbon atoms, pyridyl group, quinolyl group, alkyl group having 1 to 20 carbon atoms, or alkoxy group having 1 to 20 carbon atoms.

In the formulae (B4) to (B6), L represents an aromatic hydrocarbon group having 6 to 60 ring carbon atoms, pyridinylene group, quinolinylene group or fluorenylene group.

In the formulae (B4) to (B6), $Ar^1$ represents an aromatic hydrocarbon group having 6 to 60 ring carbon atoms, pyridinylene group or quinolinylene group.

In the formulae (B4) to (B6), $Ar^2$ represents an aromatic hydrocarbon group having 6 to 60 ring carbon atoms, pyridyl group, quinolyl group, alkyl group having 1 to 20 carbon atoms, or alkoxy group having 1 to 20 carbon atoms.

In the formula (B2), $R^8$ to $R^{12}$ each independently represent a hydrogen atom or a hydrocarbon group having 1 to 40 carbon atoms. Adjacent groups may form a cyclic structure. The hydrocarbon group may have a substituent.

In the formula (B3), $R^{13}$ to $R^{27}$ each independently represent a hydrogen atom or a hydrocarbon group having 1 to 40 carbon atoms. Adjacent groups may form a cyclic structure. The hydrocarbon group may have a substituent.

Examples of the hydrocarbon group having 1 to 40 carbon atoms represented by each of $R^8$ to $R^{12}$ and $R^{13}$ to $R^{27}$ in the formulae (B2) and (B3) are the same as those of $R^2$ to $R^7$ in the formula (B1).

Examples of a divalent group formed when adjacent groups of $R^8$ to $R^{12}$ in the formula (B2) and adjacent groups of $R^{13}$ to $R^{27}$ in the formula (B3) form a cyclic structure are a tetramethylene group, pentamethylene group, hexamethylene group, diphenylmethane-2,2'-diyl group, diphenylethane-3,3'-diyl group and diphenylpropane-4,4'-diyl group.

The electron transporting layer preferably contains at least one of nitrogen-containing heterocyclic derivatives respectively represented by the following formulae (B4) to (B6).

In the formulae (B4) to (B6), $Ar^3$ represents an aromatic hydrocarbon group having 6 to 60 ring carbon atoms, pyridyl group, quinolyl group, alkyl group having 1 to 20 carbon atoms, alkoxy group having 1 to 20 carbon atoms, or a group represented by —$Ar^1$-$Ar^2$ (in which $Ar^1$ and $Ar^2$ are the same as those described above).

The aromatic hydrocarbon group, pyridyl group, quinolyl group, alkyl group, alkoxy group, pyridinylene group, quinolinylene group and fluorenylene group which are described in relation to R, $R^1$, $R^2$, $R^3$, L, $Ar^1$, $Ar^2$ and $Ar^3$ in the formulae (B4) to (B6) may have a substituent.

As an electron transporting compound for the electron injecting layer or the electron transporting layer, 8-hydroxyquinoline or a metal complex of its derivative, an oxadiazole derivative and a nitrogen-containing heterocyclic derivative are preferable. An example of the 8-hydroxyquinoline or the metal complex of its derivative is a metal chelate oxinoid compound containing a chelate of oxine (typically 8-quinolinol or 8-hydroxyquinoline). For instance, tris(8-quinolinol) aluminum can be used. Examples of the oxadiazole derivative are as follows.

(B4)

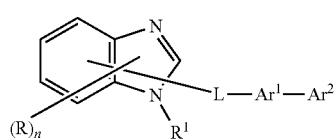

(B5)

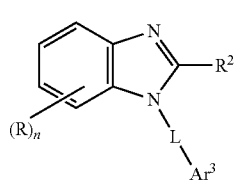

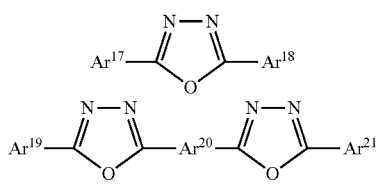

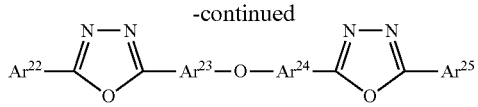

In each of the formulae of the oxadiazole derivatives, $Ar^{17}$, $Ar^{18}$, $Ar^{19}$, $Ar^{21}$, $Ar^{22}$ and $Ar^{25}$ represent an aromatic hydrocarbon group having 6 to 40 ring carbon atoms.

Note that the aromatic hydrocarbon group described herein may have a $A_r21$ substituent. $Ar^{17}$, $Ar^{19}$ and $Ar^{22}$ are respectively the same as or different from $Ar^{18}$, $Ar^{21}$ and $Ar^{25}$.

Examples of the aromatic hydrocarbon group described herein are a phenyl group, naphthyl group, biphenyl group, anthranil group, perylenyl group and pyrenyl group. Examples of the substituent therefor are an alkyl group having 1 to 10 carbon atoms, alkoxy group having 1 to 10 carbon atoms and cyano group.

In each of the formulae of the oxadiazole derivatives, $Ar^{20}$, $Ar^{23}$ and $Ar^{24}$ are a divalent aromatic hydrocarbon group having 6 to 40 ring carbon atoms.

Note that the aromatic hydrocarbon group described herein may have a substituent.

$Ar^{23}$ and $Ar^{24}$ are the same or different.

Examples of the divalent aromatic hydrocarbon group described herein are a phenylene group, naphthylene group, biphenylene group, anthranylene group, perylenylene group and pyrenylene group. Examples of the substituent therefor are an alkyl group having 1 to 10 carbon atoms, alkoxy group having 1 to 10 carbon atoms and cyano group.

Such an electron transport compound is preferably an electron transport compound that can be favorably formed into a thin film(s). Examples of the electron transport compounds are as follows.

represented by the following formula (B7) and a derivative having a structure represented by the following formula (B8).

(B7)

(B8)

In the formula (B8), X represents a carbon atom or a nitrogen atom. $Z_1$ and $Z_2$ each independently represent a group of atoms capable of forming a nitrogen-containing heterocycle.

Preferably, the nitrogen-containing heterocyclic derivative is an organic compound having a nitrogen-containing aromatic polycyclic group having a five-membered ring or six-membered ring. When the nitrogen-containing heterocyclic derivative includes such nitrogen-containing aromatic polycyclic series having plural nitrogen atoms, the nitrogen-containing heterocyclic derivative may be a nitrogen-containing aromatic polycyclic organic compound having a skeleton formed by a combination of the skeletons respectively represented by the formulae (B7) and (B8), or by a combination of the skeletons respectively represented by the formulae (B7) and (B9).

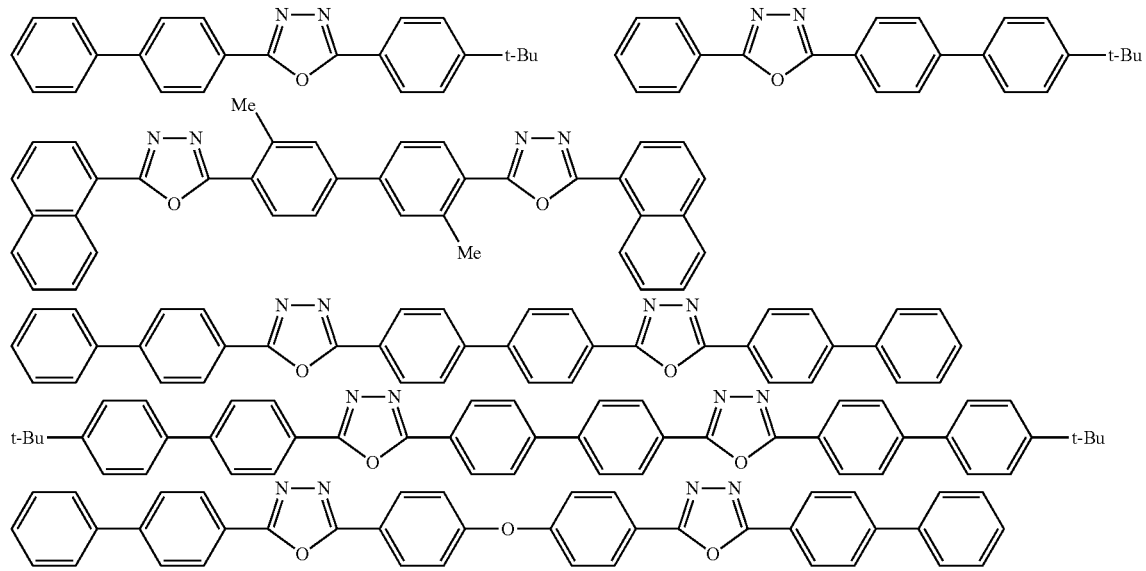

An example of the nitrogen-containing heterocyclic derivative as the electron transporting compound is a nitrogen-containing compound that is not a metal complex, the derivative being formed of an organic compound represented by one of the following general formulae. Examples of the nitrogen-containing heterocyclic derivative are a five-membered ring or six-membered ring derivative having a skeleton

(B9)

A nitrogen-containing group of the nitrogen-containing aromatic polycyclic organic compound is selected from nitrogen-containing heterocyclic groups respectively represented by the following formulae.

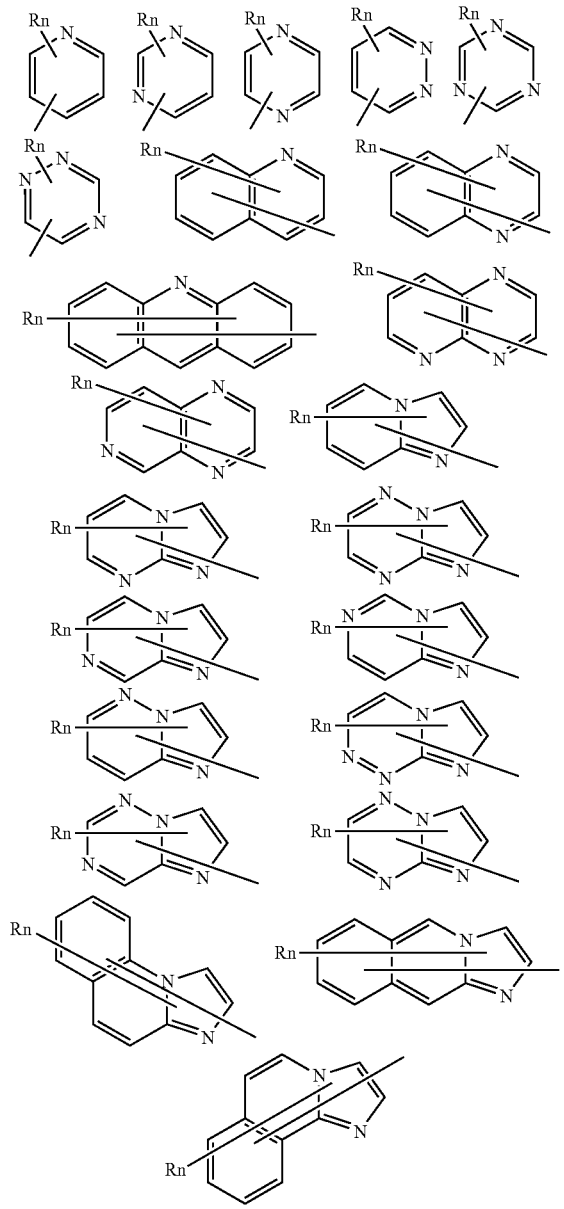

In each of the formulae of the nitrogen-containing heterocyclic groups, R represents an aromatic hydrocarbon group having 6 to 40 ring carbon atoms, aromatic heterocyclic group having 2 to 40 ring carbon atoms, alkyl group having 1 to 20 carbon atoms, or alkoxy group having 1 to 20 carbon atoms.

In each of the formulae of the nitrogen-containing heterocyclic groups, n is an integer of 0 to 5. When n is 2 or more, a plurality of R may be mutually the same or different.

A preferable specific compound is a nitrogen-containing heterocyclic derivative represented by the following formula (B10).

$$HAr-L^1-Ar^1-Ar^2 \quad (B10)$$

In the above formula (B10), HAr is a nitrogen-containing heterocyclic group having 1 to 40 ring carbon atoms.

In the formula (B10), $L^1$ is a single bond, an aromatic hydrocarbon group having 6 to 40 ring carbon atoms or aromatic heterocyclic group having 2 to 40 ring carbon atoms.

In the formula (B10), $Ar^1$ is a divalent aromatic hydrocarbon group having 6 to 40 ring carbon atoms.

In the formula (B10), $Ar^2$ is an aromatic hydrocarbon group having 6 to 40 ring carbon atoms or aromatic heterocyclic group having 2 to 40 ring carbon atoms.

The nitrogen-containing heterocyclic group, aromatic hydrocarbon group and aromatic heterocyclic group described in relation to HAr, $L^1$, $Ar^1$ and $Ar^2$ in the formula (B10) may have a substituent.

HAr in the formula (B10) is exemplarily selected from the following group.

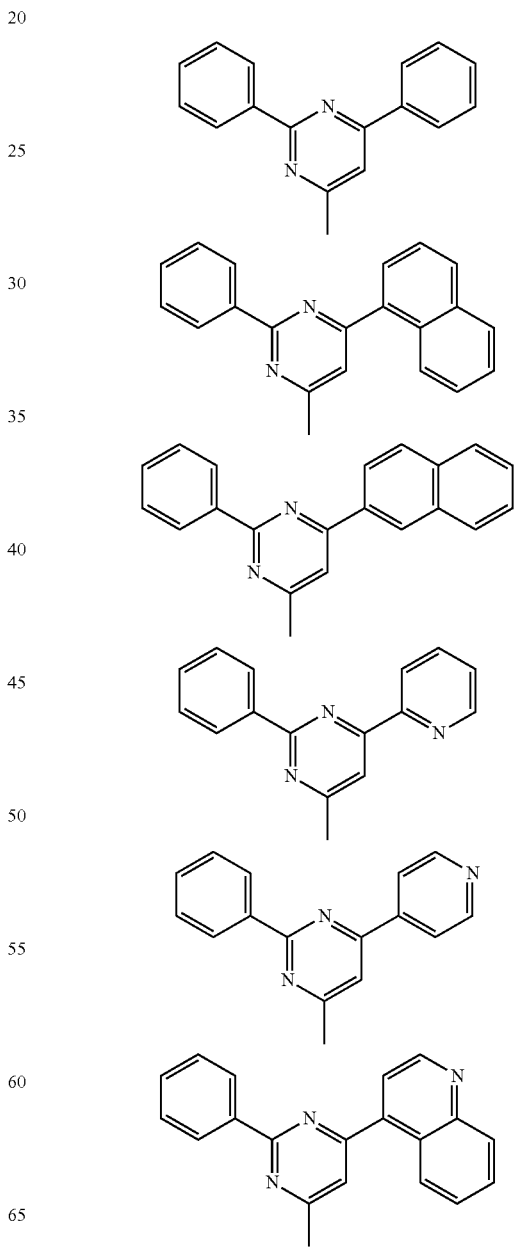

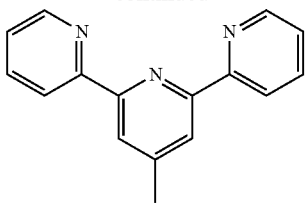
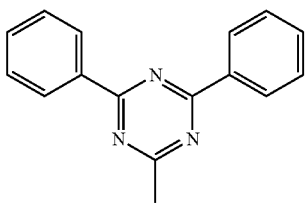
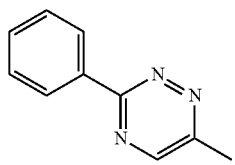
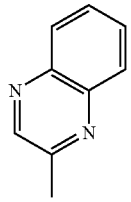
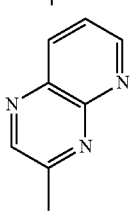
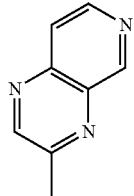
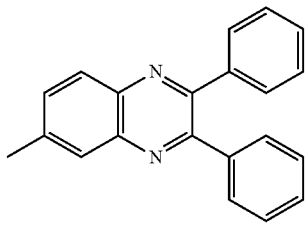
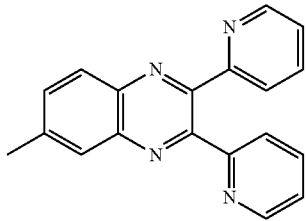
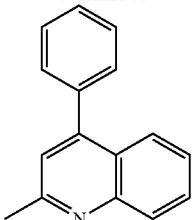
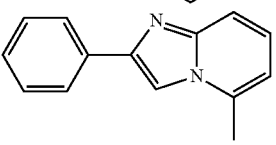
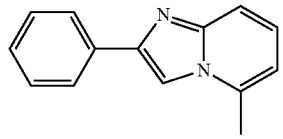
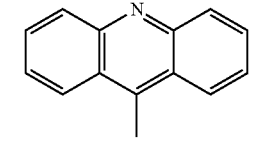
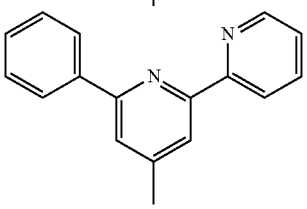
$L^1$ in the formula (B10) is exemplarily selected from the following group.
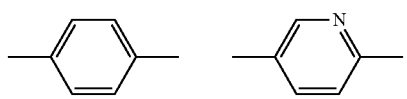
$Ar^1$ in the formula (B10) is exemplarily selected from the following arylanthranil group.
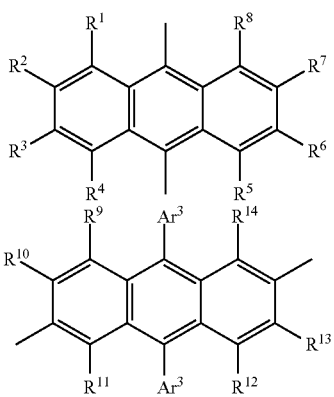

In the formula of the arylanthranil group, $R^1$ to $R^{14}$ each independently represent a hydrogen atom, halogen atom, alkyl group having 1 to 20 carbon atoms, alkoxy group having 1 to 20 carbon atoms, aryloxy group having 6 to 40 ring carbon atoms, aromatic hydrocarbon group having 6 to 40 ring carbon atoms, or aromatic heterocyclic group having 2 to 40 ring carbon atoms.

In the formula of the arylanthranil group, $Ar^3$ is an aromatic hydrocarbon group having 6 to 40 ring carbon atoms or aromatic heterocyclic group having 2 to 40 ring carbon atoms.

The aromatic hydrocarbon group and aromatic heterocyclic group described in relation to $R^1$ to $R^{14}$ and $Ar^3$ in the formula of the arylanthranil may have a substituent.

All of $R^1$ to $R^8$ of a nitrogen-containing heterocyclic derivative may be hydrogen atoms.

In the formula of the arylanthranil group, $Ar^2$ is exemplarily selected from the following group.

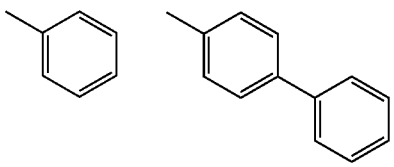

-continued

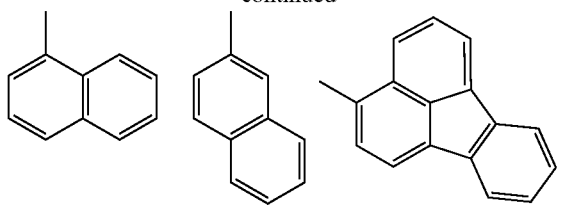

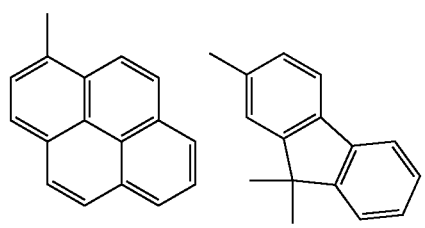

Other than the above, the following compound represented by the following formula (B11) (see JP-A-9-3448) can be favorably used for the nitrogen-containing aromatic polycyclic organic compound as the electron transporting compound.

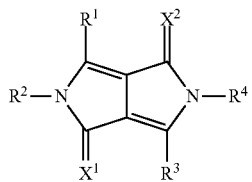

(B11)

In the formula (B11) of the nitrogen-containing aromatic polycyclic organic compound, $R^1$ to $R^4$ each independently represent a hydrogen atom, aliphatic group, alicyclic group, carbocyclic aromatic cyclic group or heterocyclic group. Note that the aliphatic group, alicyclic group, carbocyclic aromatic cyclic group and heterocyclic group may have a substituent.

In the formula (B11) of the nitrogen-containing aromatic polycyclic organic compound, $X^1$ and $X^2$ each independently represent an oxygen atom, sulfur atom or dicyanomethylene group.

The following compound represented by the following formula (B12) (see JP-A-2000-173774) can also be favorably used for the electron transporting compound.

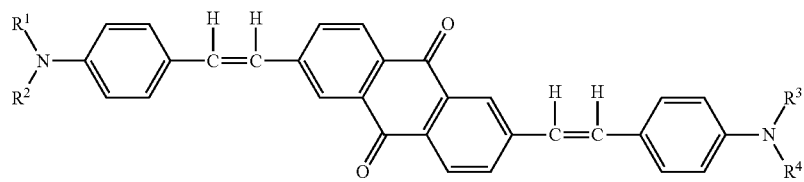

(B12)

In the formula (B12), $R^1$, $R^2$, $R^3$ and $R^4$, which may be mutually the same or different, each represent an aromatic hydrocarbon group or fused aromatic hydrocarbon group represented by the following formula (B12-1).

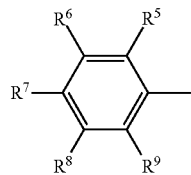

(B12-1)

In the formula (B12-1), $R^5$, $R^6$, $R^7$, $R^8$ and $R^9$, which may be mutually the same or different, each represent a hydrogen atom, a saturated or unsaturated alkoxyl group, alkyl group, amino group or alkylamino group. At least one of $R^5$, $R^6$, $R^7$, $R^8$ and $R^9$ represents a saturated or unsaturated alkoxyl group, alkyl group, amino group or alkylamino group.

A polymer compound containing the nitrogen-containing heterocyclic group or a nitrogen-containing heterocyclic derivative may be used for the electron transporting compound.

Although a thickness of the electron injecting layer or the electron transporting layer is not specifically limited, the thickness is preferably in a range of 1 nm to 100 nm.

The electron injecting layer preferably contains an inorganic compound such as an insulator or a semiconductor in addition to the nitrogen-containing cyclic derivative. Such an insulator or a semiconductor, when contained in the electron injecting layer, can effectively prevent a current leak, thereby enhancing electron injectability of the electron injecting layer.

For such an insulator, at least one metal compound selected from a group of alkali metal chalcogenide, alkaline-earth metal chalcogenide, halogenide of alkali metal, and halogenide of alkaline-earth metal may preferably be utilized. A configuration in which the electron injecting layer is formed by these alkali metal chalcogenide and the like is advantageous in that the electron injecting property is further improved. Specifically, preferable examples of the alkali metal chalcogenide are lithium oxide ($Li_2O$), potassium oxide ($K_2O$), sodium sulfide ($Na_2S$), sodium selenide ($Na_2Se$) and sodium oxide ($Na_2O$). Preferable examples of the alkaline-earth metal chalcogenide are calcium oxide (CaO), barium oxide (BaO), strontium oxide (SrO), beryllium oxide (BeO), barium sulfide (BaS) and calcium selenide (CaSe). Preferable examples of the halogenide of the alkali metal are lithium fluoride (LiF), sodium fluoride (NaF), potassium fluoride (KF), lithium chloride (LiCl), potassium chloride (KCl) and sodium chloride (NaCl). Preferable examples of the halogenide of the alkaline-earth metal are fluorides such as calcium fluoride ($CaF_2$), barium fluoride ($BaF_2$), strontium fluoride ($SrF_2$), magnesium fluoride ($MgF_2$) and beryllium fluoride ($BeF_2$), and halogenides other than the fluorides.

Examples of the semiconductor are one of or a combination of two or more of an oxide, a nitride or an oxidized nitride containing at least one element selected from barium (Ba), calcium (Ca), strontium (Sr), ytterbium (Yb), aluminum (Al), gallium (Ga), indium (In), lithium (Li), sodium (Na), cadmium (Cd), magnesium (Mg), silicon (Si), tantalum (Ta), antimony (Sb) and zinc (Zn). An inorganic compound for forming the electron injecting layer is preferably a microcrystalline or amorphous insulative thin-film. When the electron injecting layer is formed of such an insulative thin-film, more uniform thin-film can be formed, thereby reducing pixel defects such as a dark spot. Examples of such an inorganic compound are the above-described alkali metal chalcogenide, alkaline-earth metal chalcogenide, halogenide of the alkali metal and halogenide of the alkaline-earth metal.

When the electron injecting layer contains such an insulator or a semiconductor, a thickness thereof is preferably in a range of approximately 0.1 nm to 15 nm. The electron injecting layer according to the invention may preferably contain the above-described reduction-causing dopant.

Electron-Donating Dopant and Organic Metal Complex

In the organic EL device according to this exemplary embodiment, at least one of an electron-donating dopant and an organic metal complex is preferably contained in an interfacial region between the cathode and the organic thin-film layer.

With this arrangement, the organic EL device can emit light with enhanced luminance intensity and have a longer lifetime.

The electron-donating dopant may be at least one selected from an alkali metal, an alkali metal compound, an alkaline-earth metal, an alkaline-earth metal compound, a rare-earth metal, a rare-earth metal compound and the like.

The organic metal complex may be at least one selected from an organic metal complex including an alkali metal, an organic metal complex including an alkaline-earth metal, an organic metal complex including a rare-earth metal and the like.

Examples of the alkali metal are lithium (Li) (work function: 2.93 eV), sodium (Na) (work function: 2.36 eV), potassium (K) (work function: 2.28 eV), rubidium (Rb) (work function: 2.16 eV) and cesium (Cs) (work function: 1.95 eV), which particularly preferably has a work function of 2.9 eV or less. Among the above, the alkali metal is preferably K, $R^b$ or Cs, more preferably $R^b$ or Cs, the most preferably Cs.

Examples of the alkaline-earth metal are calcium (Ca) (work function: 2.9 eV), strontium (Sr) (work function: 2.0 to 2.5 eV), and barium (Ba) (work function: 2.52 eV), among which a substance having a work function of 2.9 eV or less is particularly preferable.

Examples of the rare-earth metal are scandium (Sc), yttrium (Y), cerium (Ce), terbium (Tb), and ytterbium (Yb), among which a substance having a work function of 2.9 eV or less is particularly preferable.

Since the above preferable metals have particularly high reducibility, addition of a relatively small amount of the metals to an electron injecting zone can enhance luminance intensity and lifetime of the organic EL device.

Examples of the alkali metal compound are an alkali oxide such as lithium oxide ($Li_2O$), cesium oxide ($Cs_2O$) and potassium oxide ($K_2O$), and an alkali halogenide such as sodium fluoride (NaF), cesium fluoride (CsF) and potassium fluoride (KF), among which lithium fluoride (LiF), lithium oxide ($Li_2O$) and sodium fluoride (NaF) are preferable.

Examples of the alkaline-earth metal compound are barium oxide (BaO), strontium oxide (SrO), calcium oxide (CaO) and a mixture thereof, i.e., barium strontium oxide ($Ba_xSr_{1-x}O$) ($0<x<1$), barium calcium oxide ($Ba_xCa_{1-x}O$) ($0<x<1$), among which BaO, SrO and CaO are preferable.

Examples of the rare earth metal compound are ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$) and terbium fluoride ($TbF_3$), among which $YbF_3$, $ScF_3$, and $TbF_3$ are preferable.

The organic metal complex is not specifically limited as long as containing at least one metal ion of an alkali metal ion, an alkaline-earth metal ion and a rare earth metal ion. A ligand for each of the complexes is preferably quinolinol, benzoquinolinol, acridinol, phenanthridinol, hydroxyphenyl oxazole, hydroxyphenyl thiazole, hydroxydiaryl oxadiazole, hydroxydiaryl thiadiazole, hydroxyphenyl pyridine, hydroxyphenyl benzoimidazole, hydroxybenzo triazole, hydroxy fluborane, bipyridyl, phenanthroline, phthalocyanine, porphyrin, cyclopentadiene, β-diketones, azomethines, or a derivative thereof, but the ligand is not limited thereto.

The electron-donating dopant and the organic metal complex are added to preferably form a layer or an island pattern in the interfacial region. The layer of the electron-donating dopant or the island pattern of the organic metal complex is preferably formed by evaporating at least one of the electron-donating dopant and the organic metal complex by resistance heating evaporation while an emitting material for forming the interfacial region or an organic substance as an electron-injecting material are simultaneously evaporated, so that at least one of the electron-donating dopant and an organic metal complex reduction-causing dopant is dispersed in the organic substance. Dispersion concentration at which the electron-donating dopant is dispersed in the organic substance is a mole ratio (the organic substance to the electron-donating dopant or the organic metal complex) of 100:1 to 1:100, preferably 5:1 to 1:5.

When at least one of the electron-donating dopant and the organic metal complex forms a layer, the emitting material or the electron injecting material for forming the organic layer of the interfacial region is initially layered, and then, at least one of the electron-donating dopant and the organic metal complex is singularly evaporated thereon by resistance heating evaporation to preferably form a 0.1 nm- to 15 nm-thick layer.

When at least one of the electron-donating dopant and the organic metal complex forms an island pattern, the emitting material or the electron injecting material for forming the organic layer of the interfacial region is initially layered, and then, at least one of the electron-donating dopant is singularly evaporated thereon by resistance heating evaporation to preferably form a 0.05 nm- to 1 nm-thick island pattern.

A ratio of the main component to at least one of the electron-donating dopant and the organic metal complex in the organic EL device according to the exemplary embodiment is preferably a mole ratio (the main component to the electron-donating dopant or the organic metal complex) of 5:1 to 1:5, more preferably 2:1 to 1:2.

Formation Method of Each Layer of Organic EL Device

A method of forming each of the layers in the organic EL device according to the exemplary embodiment is not particularly limited. Conventionally-known methods such as vacuum deposition and spin coating may be employed for forming the layers. The organic thin-film layer containing the compound used in the organic EL device according to this exemplary embodiment can be formed by a conventional coating method such as vacuum deposition, molecular beam epitaxy (MBE method) and coating methods using a solution such as a dipping, spin coating, casting, bar coating, and roll coating.

Thickness of Each Layer of Organic EL Device

A thickness of the emitting layer is preferably in the range of 5 nm to 50 nm, more preferably in the range of 7 nm to 50 nm and most preferably in the range of 10 nm to 50 nm. By forming the emitting layer at the thickness of 5 nm or more, the emitting layer is easily formable and chromaticity is easily adjustable. By forming the emitting layer at the thickness of 50 nm or less, increase in the drive voltage is suppressible.

A thickness of the organic thin-film layer other than the emitting layer is not particularly limited, but is preferably in a typical range of several nm to 1 μm. When the thickness is provided in the above range, defects such as pin holes caused by an excessively thinned film can be avoided while increase in the drive voltage caused by an excessively thickened film can be suppressed to prevent deterioration of the efficiency.

Modifications Of Embodiment(S)

It should be noted that the invention is not limited to the above exemplary embodiment but may include any modification and improvement as long as such modification and improvement are compatible with the invention.

An arrangement of the organic EL device is not particularly limited to the arrangement of the organic EL device 1 shown in FIG. 1. For instance, an electron blocking layer may be provided to the emitting layer adjacent to the anode while a hole blocking layer may be provided to the emitting layer adjacent to the cathode. With this arrangement, the electrons and the holes can be trapped in the emitting layer, thereby enhancing probability of exciton generation in the emitting layer.

The emitting layer is not limited to a single layer, but may be provided as laminate by a plurality of emitting layers. When the organic EL device has the plurality of emitting layers, at least one of the emitting layers preferably contains a biscarbazole derivative of the invention.

Moreover, when the organic EL device includes the plurality of emitting layers, the plurality of emitting layers may be adjacent to each other, or may be laminated on each other via a layer other than the emitting layers (e.g., a charge generating layer).

EXAMPLES

Next, the invention will be described in more detail by exemplifying Example(s) and Comparative(s). However, the invention is not limited by the description of Example(s).

Synthesis of Compound(s)

Synthesis Example 1(Synthesis of Compound H1)

A synthesis method of a compound H1 will be described including a synthesis method of an intermediate body.

Synthesis Example (1-1)

Synthesis of Intermediate Body 1

Firstly, a synthesis method of an intermediate body 1 will be described below. Next, a synthesis scheme of the intermediate body 1 is shown below.

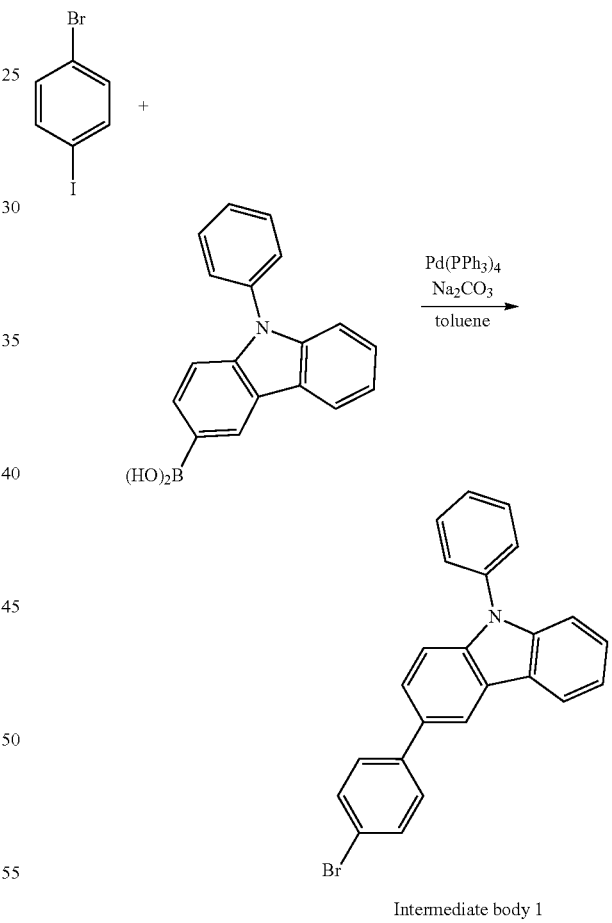

Intermediate body 1

Under argon gas, 4-bromo-1-iodobenzene (11.3 g, 40 mmol), 9-phenylcarbazolyl-3-boronic acid (11.5 g, 40 mmol), tetrakis(triphenylphosphine)palladium (1.39 g, 1.2 mmol), toluene (120 mL) and an aqueous solution of 2M sodium carbonate (60 mL) were sequentially mixed, and heated to reflux for eight hours.

After the reaction solution was cooled down to the room temperature, an organic layer was removed and an organic solvent was distilled away under reduced pressure. The obtained residue was refined by silica-gel column chromatography, so that the intermediate body 1 (11.0 g, a yield of 69%) was obtained. As a result of FD-MS (Field Desorption Mass Spectrometry: hereinafter abbreviated to FD-MS) analysis, the reactant was identified as the intermediate body 1.

Synthesis Example (1-2)

Synthesis of Intermediate Body 2

Next, a synthesis method of an intermediate body 2 will be described. Next, a synthesis scheme of the intermediate body 2 is shown below.

After the reaction solution was cooled down to the room temperature, an organic layer was removed and an organic solvent was distilled away under reduced pressure. The obtained residue was refined by silica-gel column chromatography, so that the intermediate body 2 (10 g, a yield of 91%) was obtained. As a result of FD-MS analysis, the reactant was identified as the intermediate body 2.

Synthesis Example (1-3)

Synthesis of Intermediate Body 3

Next, a synthesis method of an intermediate body 3 will be described. Next, a synthesis scheme of the intermediate body 3 is shown below.

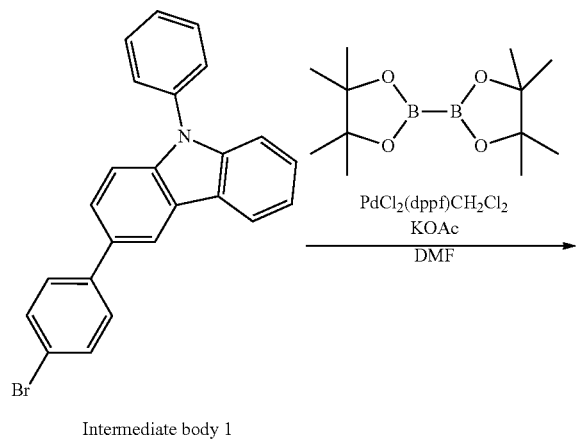

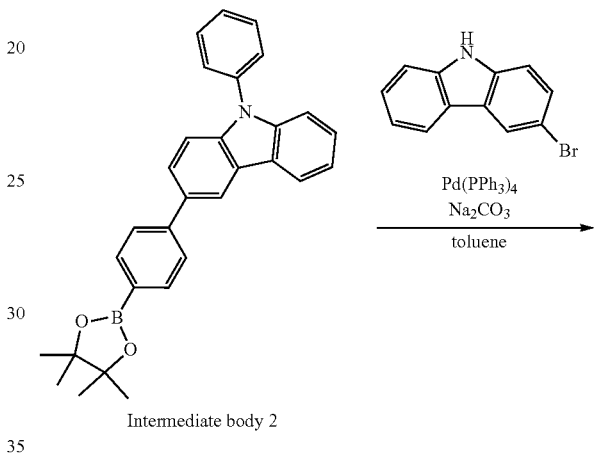

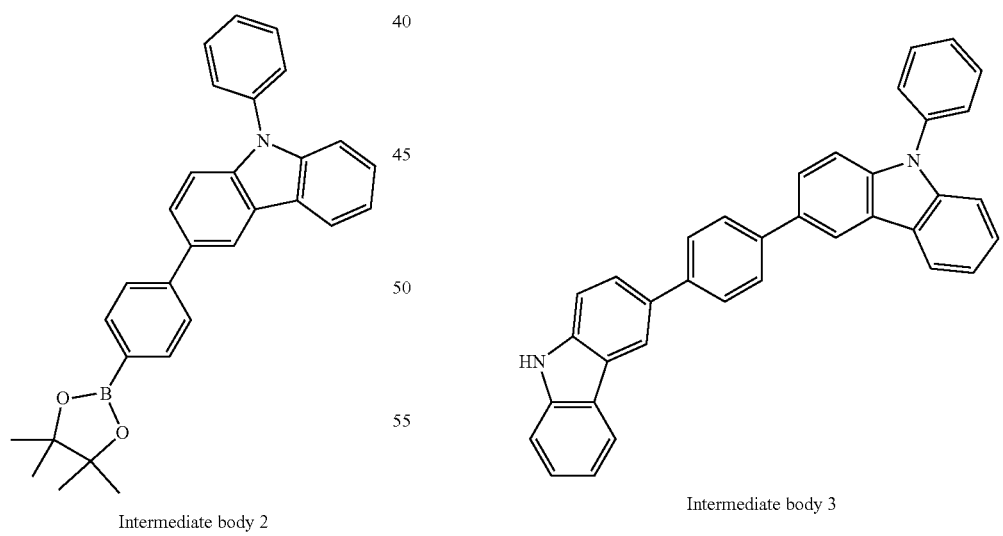

Under argon gas, the intermediate body 1 (10 g, 25 mmol), bis(pinacolato)diboron (8.3 g, 33 mmol), [1,1'-bis(diphenylphosphino)ferrocene]palladium (II) dichloride dichloromethane adduct (0.62 g, 0.75 mmol), potassium acetate (7.4 g, 75 mmol) and N,N-dimethylformamide (170 mL) were sequentially mixed, and heated to reflux for eight hours.

The intermediate body 3 was synthesized according to the same method as that for the synthesis of the intermediate body 1 in the Synthesis Example (1-1), except for using 3-bromocarbazole in place of 4-bromo-1-iodobenzene and the intermediate body 2 in place of 9-phenylcarbazolyl-3-boronic acid. As a result of FD-MS analysis, the reactant was identified as the intermediate body 3.

Synthesis Example (1-4) Synthesis of Compound H1

A synthesis scheme of the compound H1 is shown below.

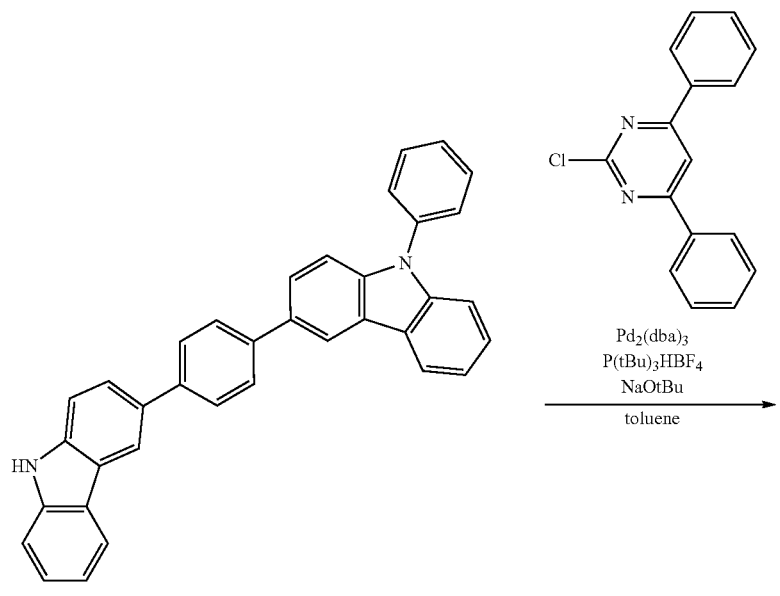

Intermediate body 3

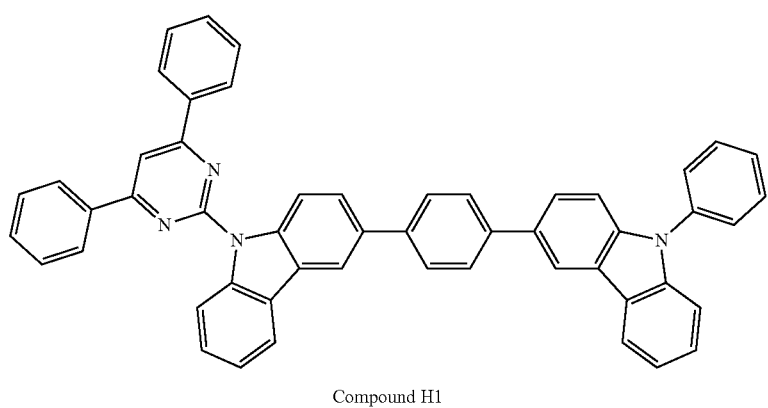

Compound H1

Under argon gas, the intermediate body 3 (1.6 g, 3.9 mmol), 2,6-diphenylpyrimidine-4-chloride (1.0 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for eight hours.

After the reaction solution was cooled down to the room temperature, an organic layer was removed and an organic solvent was distilled away under reduced pressure. The obtained residue was refined by silica-gel column chromatography, whereby a white solid (0.88 g) was obtained. As a result of FD-MS, the obtained compound was identified as the compound H1.

FD-MS: calcd for $C_{52}H_{34}N_4$=714, found m/z=714(M+, 100)

Synthesis Example 2(Synthesis of Compound H2)

A synthesis method of a compound H2 will be described. A synthesis scheme of the compound H2 is shown below.

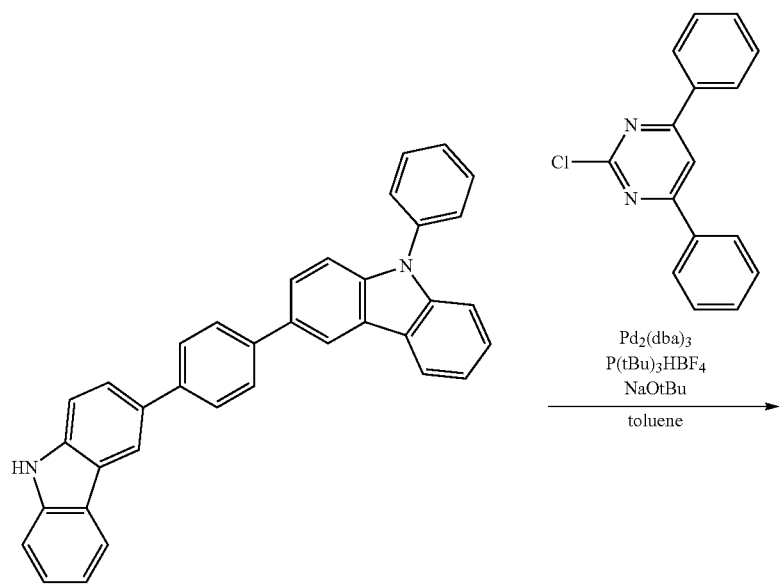

Intermediate body 3

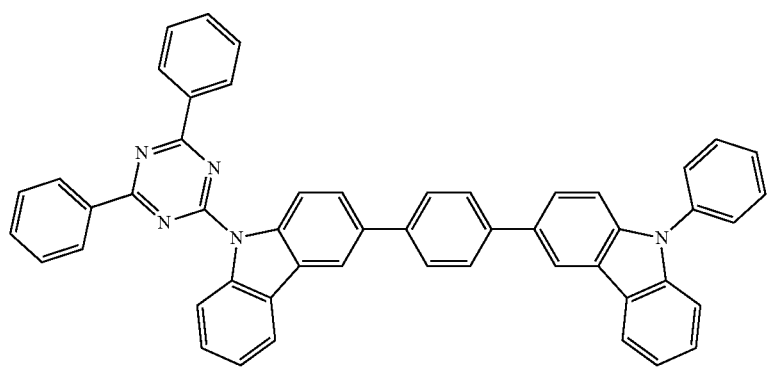

Compound H2

Under argon gas, the intermediate body 3 (1.6 g, 3.9 mmol), 2,6-diphenyltriazine-4-chloride (1.0 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for eight hours.

After the reaction solution was cooled down to the room temperature, an organic layer was removed and an organic solvent was distilled away under reduced pressure. The obtained residue was refined by silica-gel column chromatography, whereby a white solid (0.78 g) was obtained. As a result of FD-MS, the obtained compound was identified as the compound H2.

FD-MS: calcd for $C_{51}H_{33}N_5$=715, found m/z=715(M+, 100)

Synthesis Example 3(Synthesis of Compound H3)

A synthesis method of a compound H3 will be described. A synthesis scheme of the compound H3 is shown below.

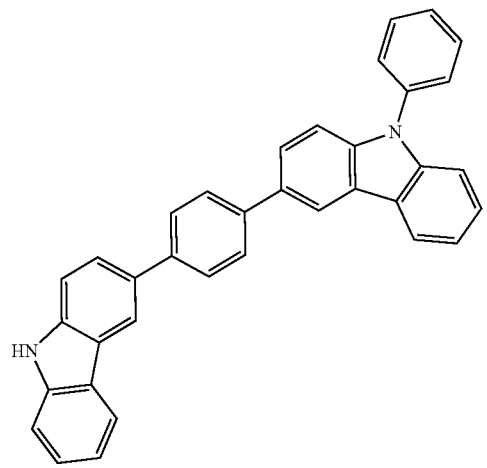

Intermediate body 3

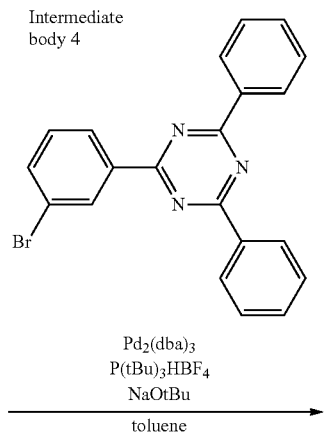

Intermediate body 4

Pd₂(dba)₃
P(tBu)₃HBF₄
NaOtBu
toluene

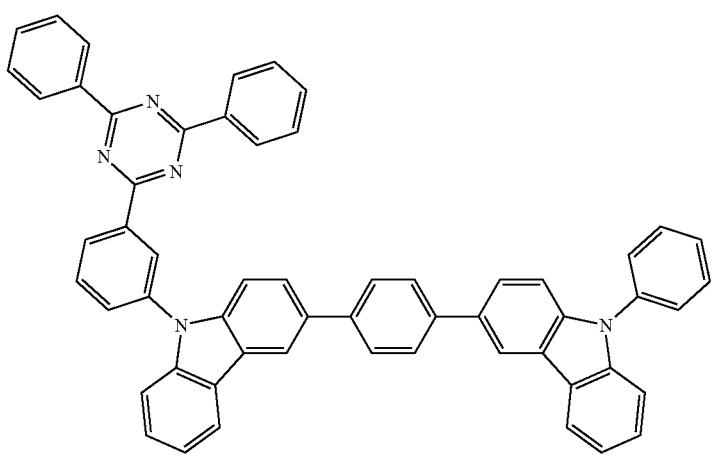

Compound H3

Under argon gas, the intermediate body 3 (1.6 g, 3.9 mmol), an intermediate body 4 (1.5 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for eight hours.

After the reaction solution was cooled down to the room temperature, an organic layer was removed and an organic solvent was distilled away under reduced pressure. The obtained residue was refined by silica-gel column chromatography, whereby a solid (1.1 g) was obtained. As a result of FD-MS, the obtained compound was identified as the compound H3.

FD-MS: calcd for $C_{57}H_{37}N_5$=791, found m/z=791(M+, 100)

Synthesis Example 4(Synthesis of Compound H4)

A synthesis method of a compound H4 will be described including a synthesis method of an intermediate body.

Synthesis Example (4-1)

Synthesis of Intermediate Body 5

Firstly, a synthesis method of an intermediate body 5 will be described. Next, a synthesis scheme of the intermediate body 5 is shown below.

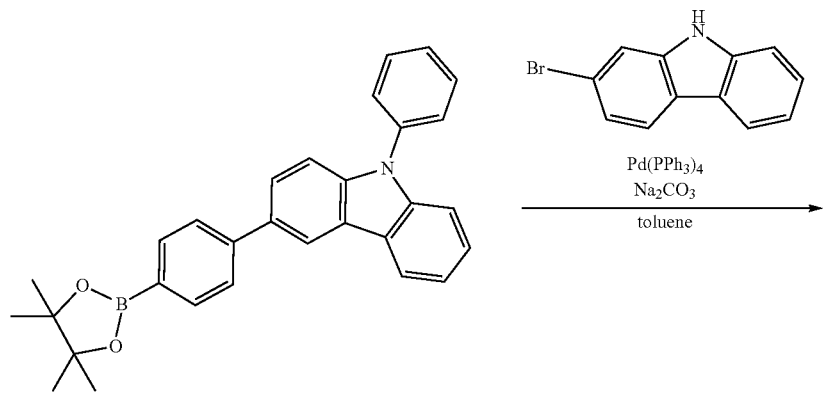

Intermediate body 2

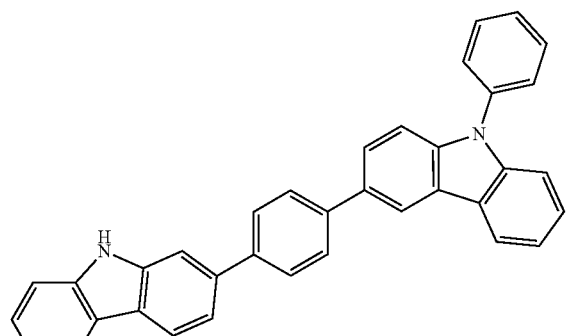

Intermediate body 5

The intermediate body 5 was synthesized according to the same method as that for the synthesis of the intermediate body 1, except for using 2-bromocarbazole in place of 4-bromo-1-iodobenzene and the intermediate body 2 in place of 9-phenylcarbazolyl-3-boronic acid. As a result of FD-MS analysis, the reactant was identified as the intermediate body 5.

Synthesis Example (4-2) (Synthesis of Compound H4)

A synthesis scheme of the compound H4 is shown below.

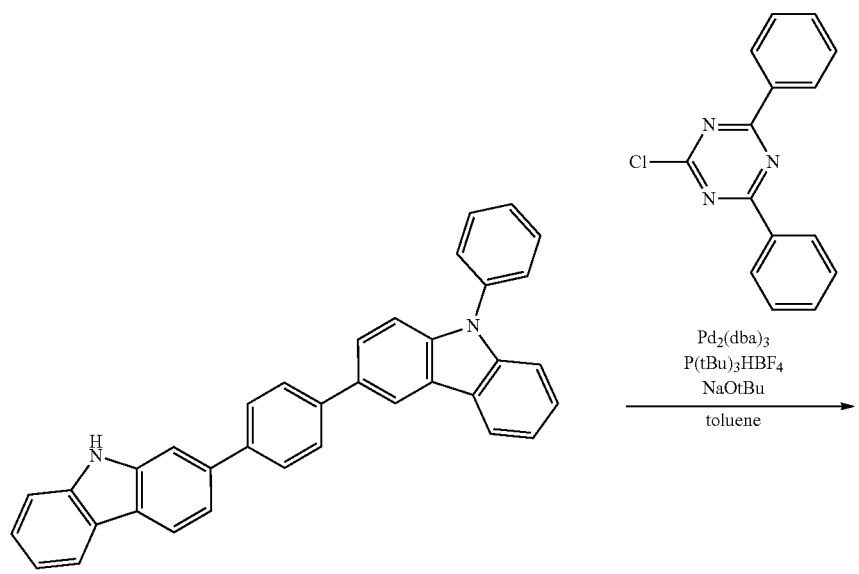

Intermediate body 5

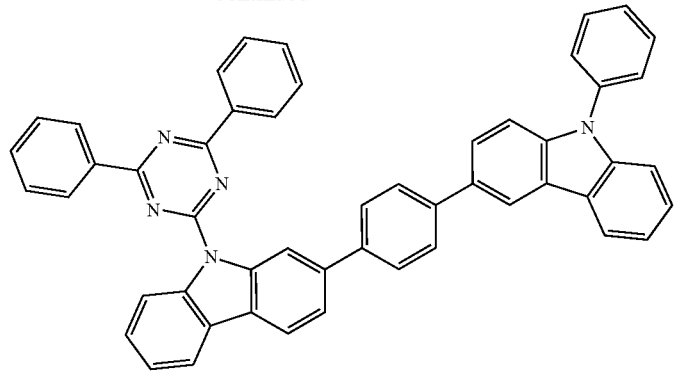

Compound H4

Under argon gas, the intermediate body 5 (1.6 g, 3.9 mmol), 2,6-diphenyltriazine-4-chloride (1.0 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for eight hours.

After the reaction solution was cooled down to the room temperature, an organic layer was removed and an organic solvent was distilled away under reduced pressure. The obtained residue was refined by silica-gel column chromatography, whereby a white solid (0.80 g) was obtained. As a result of FD-MS, the obtained compound was identified as the compound H4.

FD-MS: calcd for $C_{51}H_{33}N_5$=715, found m/z=715(M+, 100)

Manufacture and Evaluation on Luminescent Performance of Organic EL Device

Compounds used in Examples and Comparatives are shown below.

Compound C-1

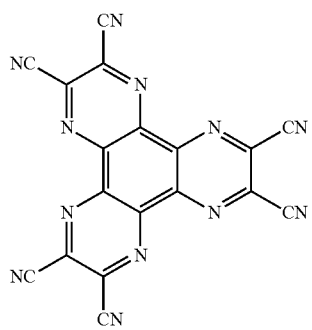

Compound X1

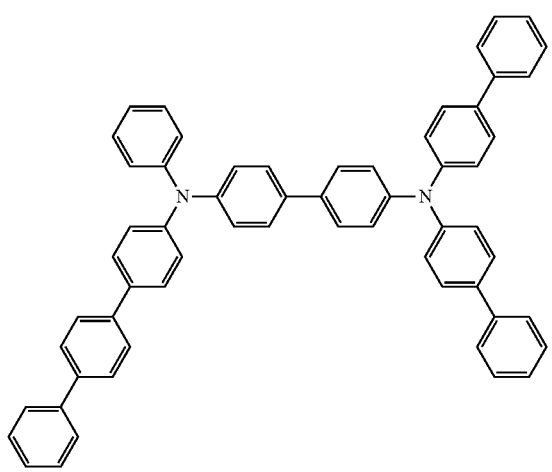

Compound X2

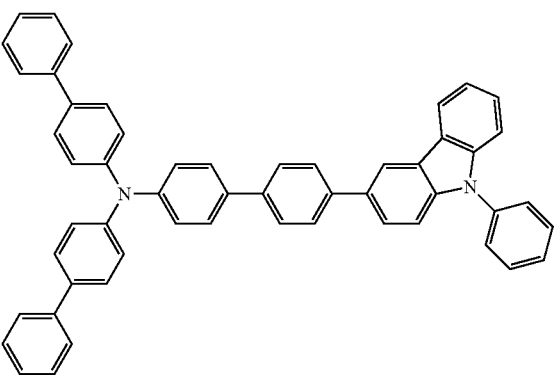

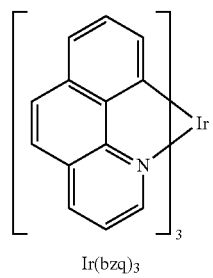

Ir(bzq)$_3$

Compound ET
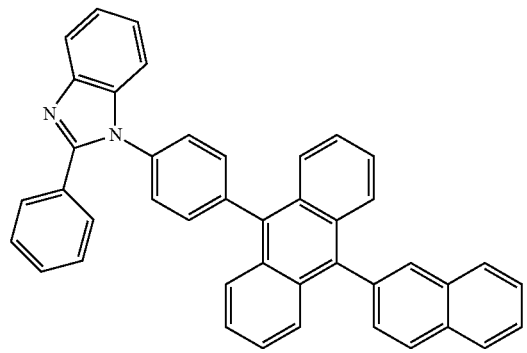
Compound H1
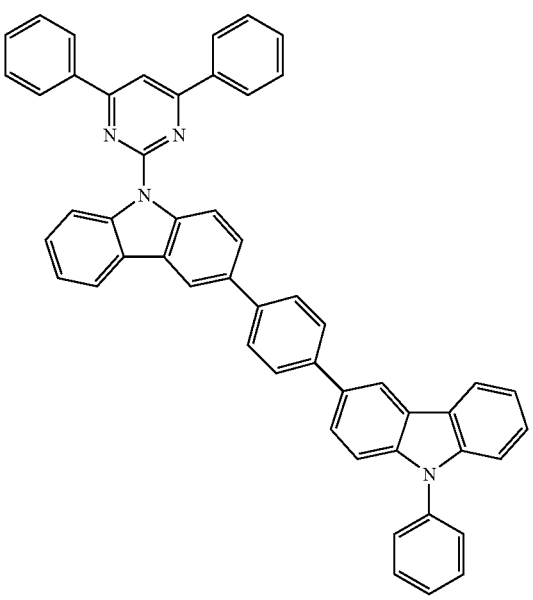
Compound H2
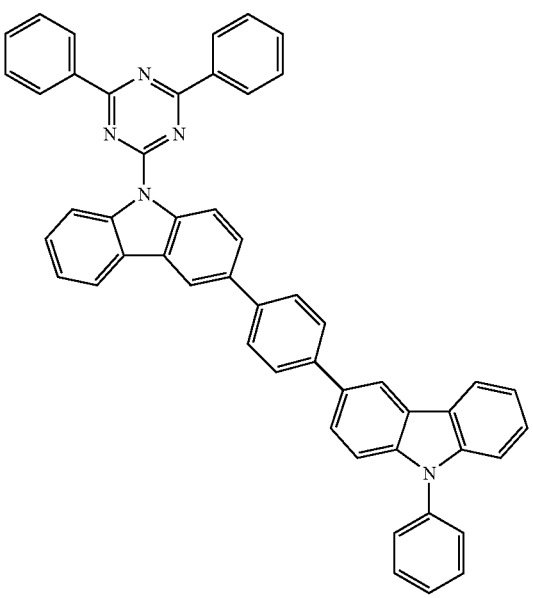
Compound H3
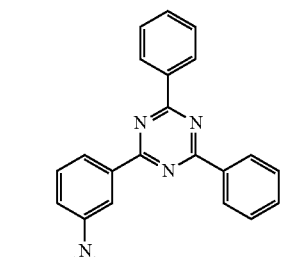
Compound H4
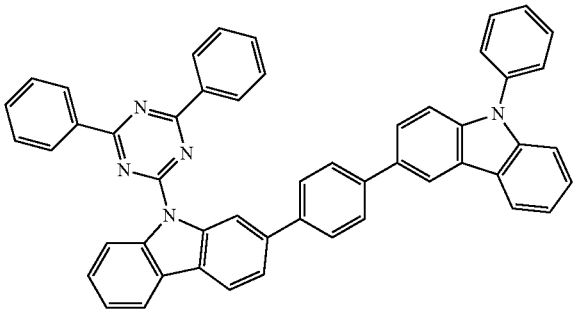
Compound PH1
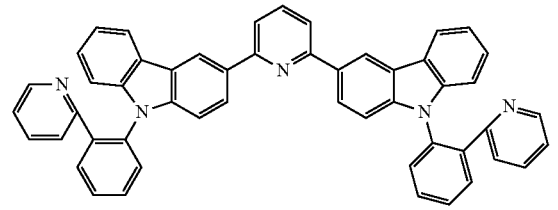
Compound PH2
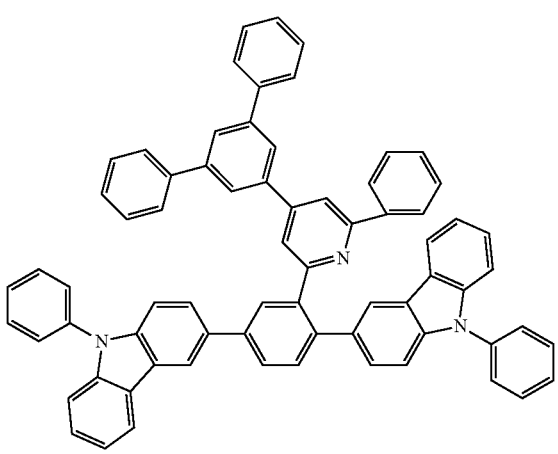

Compound PH3

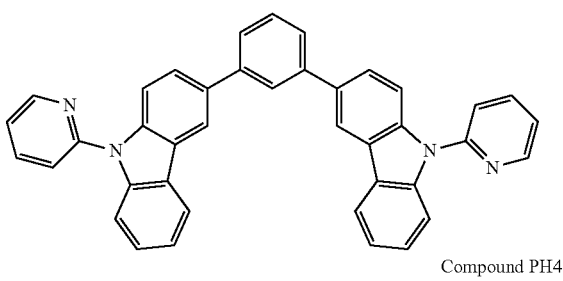

Compound PH4

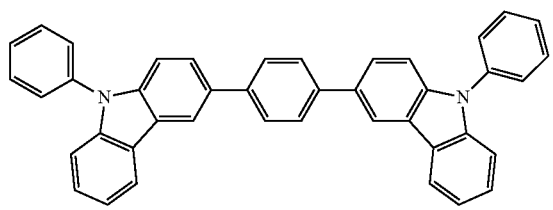

Manufacture of Organic EL Device

Example 1

A glass substrate (size: 25 mm×75 mm×1.1 mm thick) having an ITO transparent electrode (manufactured by GEO-MATEC Co., Ltd.) was ultrasonic-cleaned in isopropyl alcohol for five minutes, and then UV/ozone-cleaned for 30 minutes.

After the glass substrate having the transparent electrode line was cleaned, the glass substrate was mounted on a substrate holder of a vacuum deposition apparatus, so that the above-described electron accepting (acceptor) compound (C-1) was evaporated to form a 5-nm thick film of the compound C-1 on a surface of the glass substrate where the transparent electrode line was provided so as to cover the transparent electrode.

On the film of the compound C-1, the above aromatic amine derivative (compound X1) was evaporated as a first hole transporting material to form a 65-nm thick first hole transporting layer.

On the first hole transporting layer, the above aromatic amine derivative (compound X2) was evaporated as a second hole transporting material to form a 10-nm thick second hole transporting layer.

Further, on the second hole transporting layer, the compound H1 obtained in the Synthesis Example 1 was co-evaporated as the host material with the above compound $Ir(bzq)_3$ as the phosphorescent dopant material to form a 25-nm thick emitting layer. A concentration of the compound $Ir(bzq)_3$ in the emitting layer was 10.0 mass %. The compound $Ir(bzq)_3$ is a phosphorescent material exhibiting yellow emission.

The compound ET was evaporated on the emitting layer to form a 35-nm thick film of the compound ET. The film of the compound ET serves as the electron transporting layer.

Next, LiF was evaporated on the film of the compound ET at a film formation speed of 0.1 angstrom/min to form a 1-nm thick LiF film as an electron-injecting electrode (cathode).

A metal Al was evaporated on the LiF film to form an 80-nm thick metal cathode.

Thus, the organic EL device of Example 1 was manufactured.

Examples 2 to 4 and Comparatives 1 to 4

The organic EL devices of Examples 2 to 4 and Comparatives 1 to 4 were manufactured in the same manner as in Example 1 except that the emitting layer was formed of compounds shown in Table 1 in place of the compound H1 as the host material for the emitting layer.

Evaluation on Luminescent Performance of Organic EL Device

A voltage was applied to the manufactured organic EL device so that a current density became 1 $mA/cm^2$ at a room temperature, and EL emission spectrum at that time was measured by a spectro radiance meter (CS-1000: manufactured by Konica Minolta Holdings, Inc.). A current efficiency (cd/A) was calculated from the obtained spectral-radiance spectra.

TABLE 1

|  | Emitting Layer Host Material | Luminous Efficiency (cd/A) |
| --- | --- | --- |
| Example 1 | Compound H1 | 60 |
| Example 2 | Compound H2 | 57 |
| Example 3 | Compound H3 | 62 |
| Example 4 | Compound H4 | 64 |
| Comparative 1 | Compound PH1 | 22 |
| Comparative 2 | Compound PH2 | 20 |
| Comparative 3 | Compound PH3 | 25 |
| Comparative 4 | Compound PH4 | 15 |

As shown in Table 1, the organic EL devices of Examples 1 to 4 exhibited emission at a higher luminous efficiency as compared with the organic EL devices of Comparatives 1 to 4. It is speculated that the luminous efficiency of the organic EL devices of Comparatives 1 to 3 was decreased because the hole transporting capability of each of the compounds PH1 to PH3 used as the host material was lower than that of each of the compounds H1 to H4 in Examples 1 to 4. Moreover, it is speculated that the luminous efficiency of the organic EL device of Comparative 4 was decreased because the compound PH4 had no nitrogen-containing six-membered ring and exhibited an excessively high hole transporting capability to cause unbalance between holes and electrons in the emitting layer.

The hole transporting capability of each of the compounds PH1 to PH4 are specifically considered as follows.

The compound PH1 used in the organic EL device in Comparative 1 has two carbazoles linked to each other through a pyridine ring. In the pyridine ring, one of Cz is bonded to an m-position (meta-position) of the pyridine ring bonded to the other Cz. Accordingly, in the compound PH1, conjugation of the two carbazoles is broken to hamper expansion of π conjugated system and expansion of HOMO. For this reason, it is speculated that the compound PH1 failed to exhibit a sufficient hole transporting capability.

The compound PH2 used in the organic EL device of Comparative 2 has two carbazoles linked to each other through a phenylene ring. One of Cz is bonded to a p-position of the phenylene ring bonded to the other Cz. However, the phenylene group that links the carbazoles of the compound PH2 has a substituent, in which the substituent damages flatness of the carbazoles and breaks conjugation therebetween. For this reason, it is speculated that the compound PH2 also failed to exhibit a sufficient hole transporting capability, similarly to the compound PH1.

The compound PH3 used in the organic EL device in Comparative 3 has carbazoles linked to each other through m-phenylene. Also in the compound, conjugation of the two carbazoles is broken to hamper expansion of n conjugated system and expansion of HOMO in the same manner as described above. For this reason, it is speculated that the compound PH3 failed to exhibit a sufficient hole transporting capability.

The compound PH4 used in the organic EL device of Comparative 4 has two carbazoles linked to each other through a p-phenylene ring. The organic EL device of Comparative 4 exhibited a low luminous efficiency. Since the compound PH4 has no nitrogen-containing aromatic heterocyclic group at N position of Cz and exhibits a high hole transporting capability, it is estimated that excessive holes exist in the emitting layer of the organic EL device of Comparative 4.

What is claimed is:

1. A compound represented by a formula (1) below,

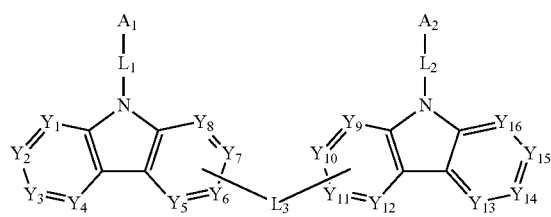

wherein: one of $A_1$ and $A_2$ is a substituted or unsubstituted nitrogen-containing aromatic heterocyclic group having 1 to 30 ring carbon atoms, and the other of $A_1$ and $A_2$ is a substituted or unsubstituted aromatic hydrocarbon group having 6 to 30 ring carbon atoms;

$Y_1$ to $Y_{16}$ each independently represent CR or a nitrogen atom; among $Y_5$ to $Y_{12}$, ones bonded to $L_3$ represent a carbon atom; in CR, R each independently represents a hydrogen atom, a substituted or unsubstituted aromatic hydrocarbon group having 6 to 30 ring carbon atoms, a substituted or unsubstituted aromatic heterocyclic group having 1 to 30 ring carbon atoms, a substituted or unsubstituted linear, branched or cyclic alkyl group having 1 to 30 carbon atoms, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a substituted or unsubstituted haloalkyl group having 1 to 30 carbon atoms, a substituted or unsubstituted haloalkoxy group having 1 to 30 carbon atoms, a substituted or unsubstituted alkylsilyl group having 3 to 30 carbon atoms, a substituted or unsubstituted dialkylarylsilyl group having 8 to 40 carbon atoms, a substituted or unsubstituted alkyldiarylsilyl group having 13 to 50 carbon atoms, a substituted or unsubstituted triarylsilyl group having 18 to 60 carbon atoms, a substituted or unsubstituted alkenyl group having 2 to 30 carbon atoms, a substituted or unsubstituted alkynyl group having 2 to 30 carbon atoms, a halogen atom, a cyano group, a hydroxyl group, a nitro group or a carboxy group; when a plurality of R are present, the plurality of R are the same or different; when adjacent two of $Y_1$ to $Y_{16}$ are CR, in the adjacent CR, a part of R is optionally bonded to a part of R to form a cyclic structure;

$L_1$ to $L_2$ each independently represent a single bond or a linking group; and $L_3$ represents a linking group represented by any one of the following formulae (2) to (4) or a composite linking group in which the linking groups represented by the formulae (2) to (4) are combined,

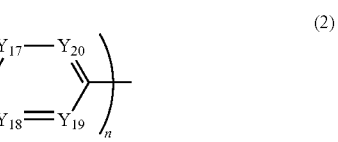

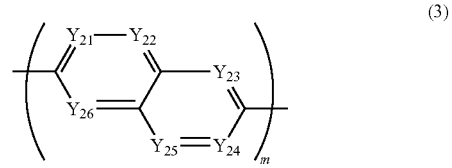

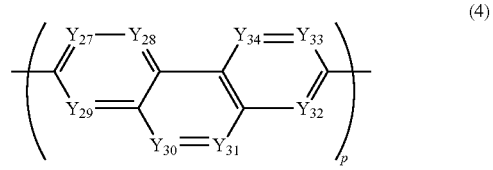

wherein: $Y_{17}$ to $Y_{34}$ each independently represent CH or a nitrogen atom;

n, m and p each independently represent an integer of 1 to 5; and when $L_3$ is a composite linking group in which the linking groups represented by the formulae (2) to (4) are combined, n+m+p is an inter of 1 to 5.

2. The compound according to claim 1, wherein at least one of $A_1$ and $A_2$ in the formula (1) is represented by a formula (5) below,

wherein: $X_1$ to $X_5$ each independently represent $CR^b$ or a nitrogen atom; at least one of $X_1$ to $X_5$ is a nitrogen atom and $X_1$ to $X_5$ bonded to $L_1$ or $L_2$ is a carbon atom;

in $CR^b$, $R^b$ represents a hydrogen atom or a substituent;

when adjacent two of $X_1$ to $X_5$ are $CR^b$, in the adjacent $CR^b$, a part of $R^b$ is optionally bonded to a part of $R^b$ to form a cyclic structure; and when a plurality of $R^b$ are present, the plurality of $R^b$ are the same or different.

3. The compound according to claim 1, wherein $Y_{17}$ to $Y_{34}$ in the formulae (2) to (4) are CH.

4. The compound according to claim 1, wherein one of $A_1$ and $A_2$ in the formula (1) is a substituted or unsubstituted pyrimidinyl group or a substituted or unsubstituted triazinyl group.

5. The compound according to claim 1, wherein n in the formula (2), m in the formula (3) and p in the formula (4) each independently represent an integer of 1 to 3.

6. The compound according to claim 1, wherein $L_3$ in the formula (1) is a linking group represented by the formula (2).

7. The compound according to claim 1, wherein the compound represented by the formula (1) is represented by any one of the following formulae (6) to (8),

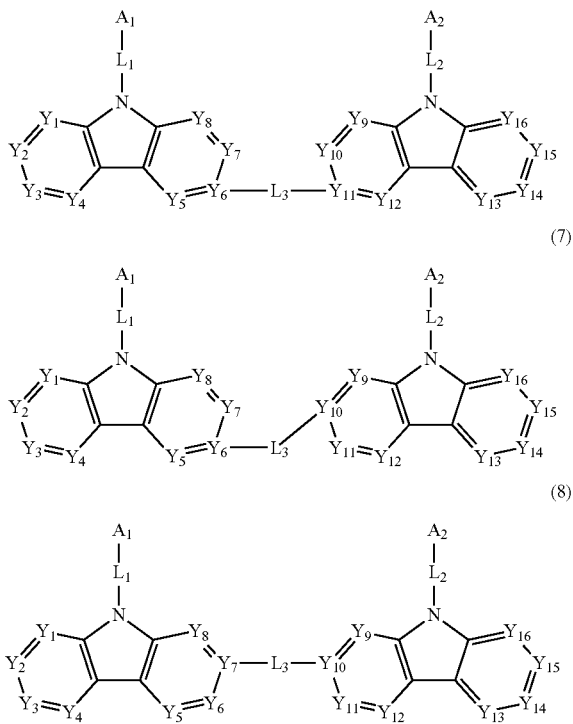

(6)
(7)
(8)

wherein: in the formula (6), $A_1, A_2, Y_1$ to $Y_5, Y_7$ to $Y_{10}, Y_{12}$ to $Y_{16}, L_1, L_2$ and $L_3$ represent the same as those in the formula (1) and $Y_6$ and $Y_{11}$ represent a carbon atom;

in the formula (7), $A_1, A_2, Y_1$ to $Y_5, Y_7$ to $Y_9, Y_{11}$ to $Y_{16}, L_1, L_2$ and $L_3$ represent the same as those in the formula (1), and $Y_6$ and $Y_{10}$ represent a carbon atom; and in the formula (8), $A_1, A_2, Y_1$ to $Y_6, Y_8$ to $Y_9, Y_{11}$ to $Y_{16}, L_1, L_2$ and $L_3$ represent the same as those in the formula (1), and $Y_7$ and $Y_{10}$ represent a carbon atom.

8. The compound according to claim 1, wherein
among $Y_5$ to $Y_{12}$, ones bonded to $L_3$ in the formula (1) are a carbon atom and the rest of $Y_5$ to $Y_{12}$ are CH.

9. A material for an organic electroluminescence device comprising the compound according to claim 1.

10. An organic electroluminescence device comprising:
a cathode;
an anode; and
an organic thin-film layer disposed between the cathode and the anode, the organic thin-film layer having one or more layers comprising an emitting layer, wherein
at least one of the organic thin-film layer comprises the compound according to claim 1.

11. The organic electroluminescence device according to claim 10, wherein the emitting layer comprises the compound.

12. The organic electroluminescence device according to claim 10, wherein the emitting layer comprises a phosphorescent material.

13. The organic electroluminescence device according to claim 12, wherein the phosphorescent material is an ortho-metalated complex of a metal atom selected from iridium (Ir), osmium (Os) and platinum (Pt).

14. The compound according to claim 1, wherein $L_1$ and $L_2$ in formula (1) each independently represent a single bond, a divalent group derived from a substituted or unsubstituted aromatic hydrocarbon compound having 6 to 30 ring carbon atoms, or a divalent group derived from a substituted or unsubstituted aromatic heterocyclic compound having 1 to 30 ring carbon atoms.

15. The compound according to claim 7, wherein $L_1$ and $L_2$ in formulae (6) to (8) each independently represent a single bond, a divalent group derived from a substituted or unsubstituted aromatic hydrocarbon compound having 6 to 30 ring carbon atoms, or a divalent group derived from a substituted or unsubstituted aromatic heterocyclic compound having 1 to 30 ring carbon atoms.

16. The compound according to claim 15, wherein $L_3$ in formulae (6) to (8) is a linking group represented by the formula (2).

17. The compound according to claim 15, wherein one of $A_1$ and $A_2$ in formulae (6) to (8) represents a substituted or unsubstituted pyrimidinyl group or a substituted or unsubstituted triazinyl group.

18. The compound according to claim 15, wherein among $Y_5$ to $Y_{12}$, ones bonded to $L_3$ in formula (6) to (8) are each a carbon atom and the rest of $Y_5$ to $Y_{12}$ are each CH.

19. The compound according to claim 16, wherein one of $A_1$ and $A_2$ in formulae (6) to (8) represents a substituted or unsubstituted pyrimidinyl group or a substituted or unsubstituted triazinyl group.

20. The compound according to claim 16, wherein among $Y_5$ to $Y_{12}$, ones bonded to $L_3$ in formula (6) to (8) are each a carbon atom and the rest of $Y_5$ to $Y_{12}$ are each CH.

* * * * *